(12) United States Patent
Blanpain et al.

(10) Patent No.: US 12,123,877 B2
(45) Date of Patent: Oct. 22, 2024

(54) DETECTION, QUANTIFICATION AND/OR ISOLATION OF CIRCULATING TUMOR CELLS BASED ON THE EXPRESSION OF CD321 MARKER

(71) Applicant: UNIVERSITÉ LIBRE DE BRUXELLES, Brussels (BE)

(72) Inventors: Cédric Blanpain, Ohain (BE); Panagiota Sotiropoulou, Kraainem (BE); Ievgenia Pastushenko, Brussels (BE)

(73) Assignee: UNIVERSITÉ LIBRE DE BRUXELLES, Brussels (BE)

( * ) Notice: Subject to any disclaimer, the term of this patent is extended or adjusted under 35 U.S.C. 154(b) by 693 days.

(21) Appl. No.: 16/494,223

(22) PCT Filed: Mar. 16, 2018

(86) PCT No.: PCT/EP2018/056760
§ 371 (c)(1),
(2) Date: Sep. 13, 2019

(87) PCT Pub. No.: WO2018/167312
PCT Pub. Date: Sep. 20, 2018

(65) Prior Publication Data
US 2021/0190787 A1      Jun. 24, 2021

(30) Foreign Application Priority Data

Mar. 16, 2017   (EP) ..................... 17161411

(51) Int. Cl.
*G01N 33/574*        (2006.01)
(52) U.S. Cl.
CPC .................. *G01N 33/57492* (2013.01); *G01N 2333/70589* (2013.01)
(58) Field of Classification Search
CPC ... G01N 33/57492; G01N 2333/70589; G01N 33/574; G01N 33/6872; G01N 2333/70596; G01N 2800/50; G01N 2800/52; G01N 2800/54
See application file for complete search history.

(56) References Cited

U.S. PATENT DOCUMENTS

| | | | |
|---|---|---|---|
| 2006/0252054 A1* | 11/2006 | Lin ................. | A61B 5/150755 435/7.23 |
| 2010/0162416 A1 | 6/2010 | Krtolica et al. | |
| 2011/0059475 A1 | 3/2011 | May et al. | |

FOREIGN PATENT DOCUMENTS

| | | | |
|---|---|---|---|
| EP | 1813945 A1 | 8/2007 | |
| EP | 2199798 A1 | 6/2010 | |
| EP | 2455403 A1 | 5/2012 | |
| WO | WO 2005/043121 A2 | 5/2005 | |
| WO | WO 2006/130737 A1 | 12/2006 | |
| WO | WO 2007/056049 A2 | 5/2007 | |
| WO | WO 2013/148450 A1 | 10/2013 | |
| WO | WO 2014/120265 A1 | 8/2014 | |
| WO | WO 2015/095527 A1 | 6/2015 | |
| WO | WO 2016/118086 A1 | 7/2016 | |

OTHER PUBLICATIONS

Lathia et al. High-Throughput Flow Cytometry Screening Reveals a Role for Junctional Adhesion Molecule A as a Cancer Stem Cell Maintenance Factor. Cell Reports 6: 117-129, published Dec. 26, 2013.*
Current Protocols in Immunology: Supplement 53: A.4A.1-A.4A.49 (2003).*
Riches et al. (Blood 123(26): 4101-4110 and supplemental data 12 pages, Jun. 26, 2014).*
Lathia et al., "High-Throughput Flow Cytometry Screening Reveals a Role for Junctional Adhesion Molecule A as a Cancer Stem Cell Maintenance Factor", Cell Reports, 2014, 6(1): 117-129.
McSherry et al., "JAM-A expression positively correlates with poor prognosis in breast cancer patients", International Journal of Cancer, 2009, 125(6): 1343-1351.
Kantara et al., "Methods for detecting circulating cancer stem cells (CCSCs) as a novel approach for diagnosis of colon cancer relapse/metastasis", Laboratory Investigation, 2015, 95: 100-112.
Duffy, "Tumor Markers in Clinical Practice: A Review Focusing on Common Solid Cancers", Medical Principles and Practice, 2013, 22: 4-11.
Kaushal et al., "Current Update on Biomarkers for Detection of Cancer: Comprehensive Analysis", Vaccines, Oct. 2022, 2138, 16 pages.
Marofi et al., "CAR T cells in solid tumors: challenges and opportunities", Stem Cell Research & Therapy, 2021, 12:81, 16 pages.
Painter et al., "Useful Immunohistochemical Markers of Tumor Differentiation", Toxicol Pathol., 2010, 38(1): 131-141.
Townsend et al., "The expansion of targetable biomarkers for CAR T cell therapy", Journal of Experimental & Clinical Cancer Research, 2018, 37:163, 23 pages.
Wang et al., "CD19: a biomarker for B cell development, lymphoma diagnosis and therapy", Experimental Hematology & Oncology, 2012, 1:36, 7 pages.
Van Velzen et al., "Multicolor flow cytometry for evaluation of platelet surface antigens and activation markers", Thrombosis Research, 2012, 130: 92-98.
Lau et al., "An integrated flow cytometry analysis of 286 mature B cell neoplasms identifies CD13 as a useful marker for diagnostic subtyping", Int J Lab Hem., 2018, 40: 715-720.

\* cited by examiner

*Primary Examiner* — Alana Harris Dent
(74) *Attorney, Agent, or Firm* — James S. Keddie; Bozicevic, Field & Francis LLP

(57) ABSTRACT

The application discloses CD321 as a useful global marker of circulating tumor cells (CTCs) and provides related methods and kits of parts relying on detection of CD321.5.

17 Claims, 19 Drawing Sheets

Specification includes a Sequence Listing.

A

B

C

DETECTION, QUANTIFICATION AND/OR ISOLATION OF CIRCULATING TUMOR CELLS BASED ON THE EXPRESSION OF CD321 MARKER

CROSS-REFERENCE TO RELATED APPLICATIONS

This application is a § 371 national phase of International Application No. PCT/EP2018/056760, filed on Mar. 16, 2018, which claims the benefit of European Patent Application No. 17161411.8, filed on Mar. 16, 2017, which applications are incorporated by reference herein.

FIELD

The invention relates to methods for detecting, quantifying or isolating tumor cells, more particularly circulating tumor cells (CTCs) in subjects, to related methods for diagnosis, prognosis or monitoring of neoplastic diseases, and to kits of parts useful for performing such methods.

BACKGROUND

Detection, quantification or isolation of tumor cells can aid the characterization, diagnosis, prognosis or monitoring of neoplastic diseases in subjects. Isolated tumor cells also provide valuable tools for the study of neoplastic disease and for preparation of tumor vaccines.

Tumor cells which leave the primary tumor and enter the circulation are known as circulating tumor cells (CTCs). A fraction of CTCs are capable of entering distant sites and persisting in secondary organs, such as liver, bone or lungs, as disseminated tumor cells (DTCs), and a fraction of DTCs are capable of progressing toward metastases. Detection, quantification or isolation of tumor cells in circulation has high significance for cancer disease management, providing a minimally-invasive means to follow the progress of cancer, response to therapy and metastatic potential.

Epithelial cell adhesion molecule (EpCAM) is currently the standard marker used to identify CTCs. For example, the commercially available Veridex CellSearch® CTC assay uses magnetic particles conjugated to an anti-EpCAM antibody to capture CTCs from blood. The enriched cells are stained with DAPI, a nucleic acid dye, to identify nucleated cells, anti-cytokeratin antibodies conjugated to phycoerythrin (PE) to identify cells of epithelial origin, and anti-leukocyte antibodies conjugated to allophycocyanin (APC) to identify all leukocytes. The samples are analyzed on a CellTracks Analyzer II® for enumeration of CTCs.

SUMMARY

The present invention addresses the need to devise alternative and/or improved ways to detect, quantify or isolate tumor cells, in particular circulating tumor cells (CTCs), allowing inter alia for alternative and/or improved methods for characterization, diagnosis, prognosis or monitoring neoplastic diseases in subjects.

As corroborated by the experimental section, which illustrates certain representative embodiments of the invention, the inventors demonstrated that conventional markers used for detection of tumors and CTCs, such as EpCAM, or Keratins, are in fact only expressed by subpopulations of cancer cells. Consequently, tumor cell- and CTC-detection methods based on such conventional markers may fail to detect the presence of tumor cells or CTCs or may at least significantly underestimate the quantity of tumor cells or CTCs in samples. Similarly, in situ-detection methods based on such conventional markers may fail to provide complete and accurate visualization of tumors.

The inventors performed extensive analyses of numerous cancer cell lines, patient-derived xenografts and primary tumors, and identified that CD321 was widely expressed by cancer cells, and was expressed more universally than classical markers, such as EpCAM or Keratin-14. Hence, whereas all EpCAM-positive and Keratin-14-positive cells in illustrative tumors co-expressed CD321, a sizeable proportion of tumor cells expressed CD321 but not EpCAM and Keratin-14. Moreover, the inventors demonstrated that CD321 expression was reliably maintained in CTCs, whereas the expression of EpCAM in CTCs was frequently lost and considerably more variable. Hence, advantageously, CD321 allowed identification of tumor cells and more particularly CTCs independently of their epithelial-mesenchymal transition (EMT) status, which positions CD321 as more reliable and/or sensitive marker of cancer cells and especially CTCs compared to the use of epithelial markers such EpCAM, mesenchymal markers or specific EMT markers alone.

The inventors' data thus identified CD321 as a practically universal or global marker of tumor cells, more particularly solid tumor cells, and particularly as a dependable marker for detection of CTCs and for in situ detection of cancers.

Accordingly, in an aspect, the invention provides a method for detecting or quantifying tumor cells in a biological sample from a subject comprising detecting the expression of CD321 by tumor cells in the biological sample.

A further aspect provides a method for isolating tumor cells from a biological sample from a subject, the method comprising detecting the expression of CD321 by tumor cells in the biological sample and isolating the CD321 expressing tumor cells from the biological sample.

Another aspect provides a method for detecting or quantifying circulating tumor cells (CTCs) in a biological sample from a subject comprising detecting the expression of CD321 by circulating non-hematopoietic cells in the biological sample, wherein the expression of CD321 by a circulating non-hematopoietic cell identifies said cell as a circulating tumor cell.

A further aspect provides a method for isolating circulating tumor cells (CTCs) from a biological sample from a subject comprising detecting the expression of CD321 by circulating non-hematopoietic cells in the biological sample, wherein the expression of CD321 by a circulating non-hematopoietic cell identifies said cell as a circulating tumor cell, and isolating the CD321 expressing CTCs from the biological sample.

Further aspects provide methods comprising the above-stated method for detecting or quantifying tumor cells or CTCs in the subject, in particular:
- a method for the diagnosis, prognosis or monitoring of a neoplastic disease in the subject;
- a method for determining the metastatic potential of a neoplastic disease in the subject, wherein the presence of tumor cells or CTCs in the subject identifies the neoplastic disease as having metastatic potential;
- a method for determining the relapse of a neoplastic disease in the subject, wherein the presence of tumor cells or CTCs in the subject identifies that the neoplastic disease has relapsed;
- a method for determining whether the subject is in need of an anti-cancer therapy, wherein the presence of tumor cells or CTCs in the subject identifies the subject as being in need of an anti-cancer therapy; or a method for determining the efficacy of an anti-cancer therapy in a subject having a neoplastic disease, comprising detecting or quantifying tumor cells or CTCs in the subject before and during or subsequent to the therapy, wherein reduced quantity of tumor cells or CTCs in the subject during or subsequent to the therapy compared to before the therapy identifies said therapy as efficacious.

Also provided are kits of parts useful for performing the methods as taught herein.

Hence, an aspect relates to a kit of parts or an article of manufacture comprising one or more agents capable of specifically binding to CD321, and one or more agents capable of specifically binding to at least one pan-leukocyte marker.

Another aspect relates to a kit of parts or an article of manufacture comprising one or more agents capable of specifically binding to CD321, and one or more agents capable of specifically binding to at least one thrombocyte marker.

A yet further aspect relates to a kit of parts or an article of manufacture comprising one or more agents capable of specifically binding to CD321, one or more agents capable of specifically binding to at least one pan-leukocyte marker, and one or more agents capable of specifically binding to at least one thrombocyte marker.

In another aspect, the invention provides a method for in situ imaging of tumor in a subject, comprising administering to the subject an agent capable of specifically binding to CD321, said agent comprising a label detectable by an imaging modality, allowing said agent to specifically bind to CD321 expressed by the cells of the tumor, and visualizing the tumor in the subject using said imaging modality.

These and further aspects and preferred embodiments of the invention are described in the following sections and in the appended claims. The subject-matter of the appended claims is hereby specifically incorporated in this specification.

DESCRIPTION OF EMBODIMENTS

Figure 1:
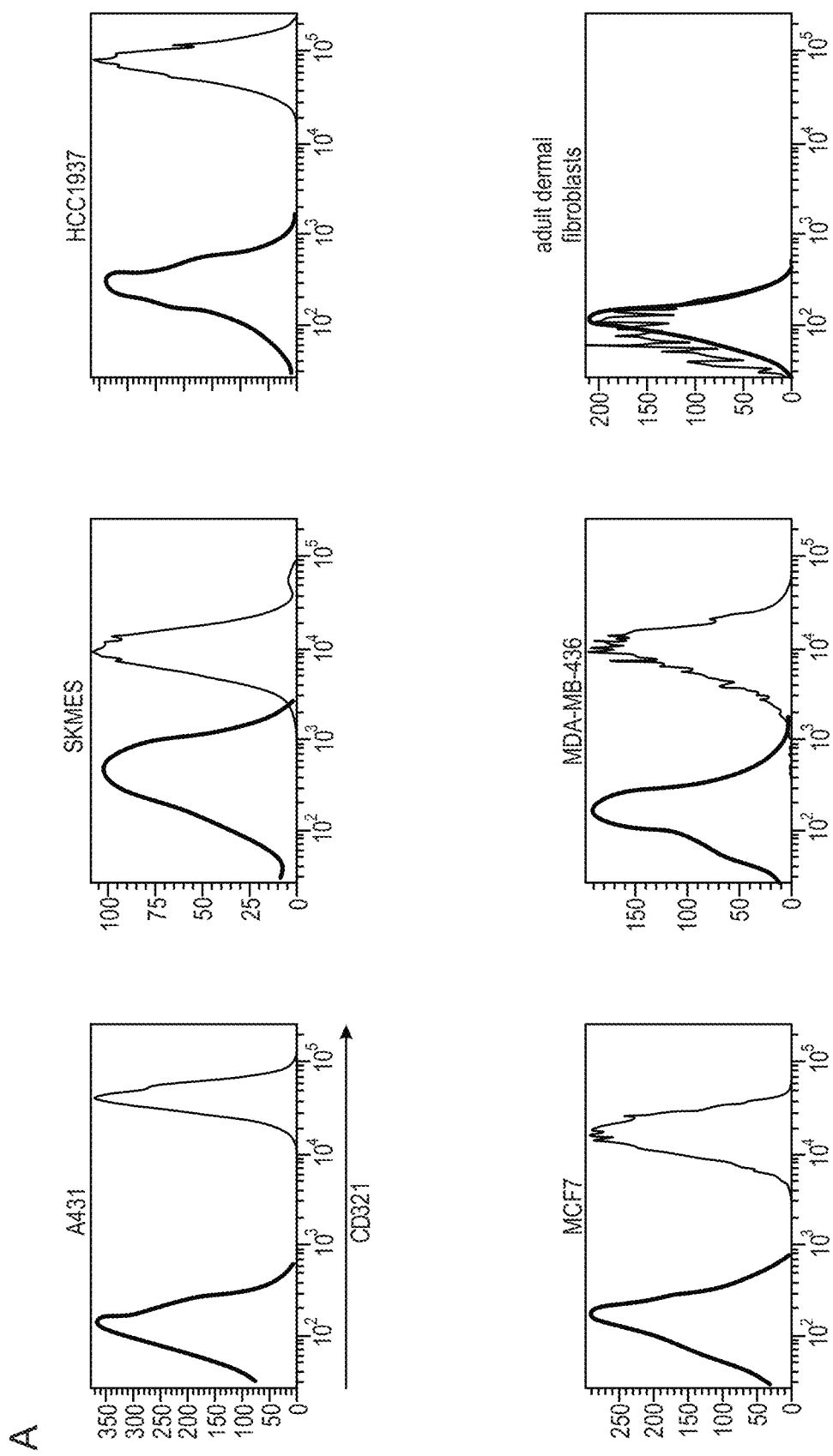
FIG. 1 illustrates that CD321 is homogeneously expressed in cell lines, patient-derived xenografts (PDX) and primary tumors. A. Cell lines from epidermoid carcinoma (A431), lung squamous cell carcinoma (SKMES), and mammary gland cancer (HCC1937, MCF7, MBA-MD-436) homogeneously expressed high levels of CD321 (filled histograms), while adult dermal fibroblasts did not express CD321. The FACS plots were gated in single living cells. The empty histograms indicate the staining with isotype control. B. Patient-derived xenografts at the first passage from skin (SP12 P1), lung (L28 P1), head & neck (HNA7 P1 and HN8 P1) and esophagus cancer (EH2 P1) homogeneously expressed CD321 (filled histograms). The FACS plots were gated in living cells, after exclusion of immune and endothelial cells of mouse and human origin. The empty histograms indicate the staining with isotype control. C. CD321 expression in human primary tumors from lung (L31) and esophagus (EMS4) cancer. The plots were gated in single living cells, after exclusion of immune and endothelial cells and the majority of cancer-associated fibroblasts.
Figure 1:
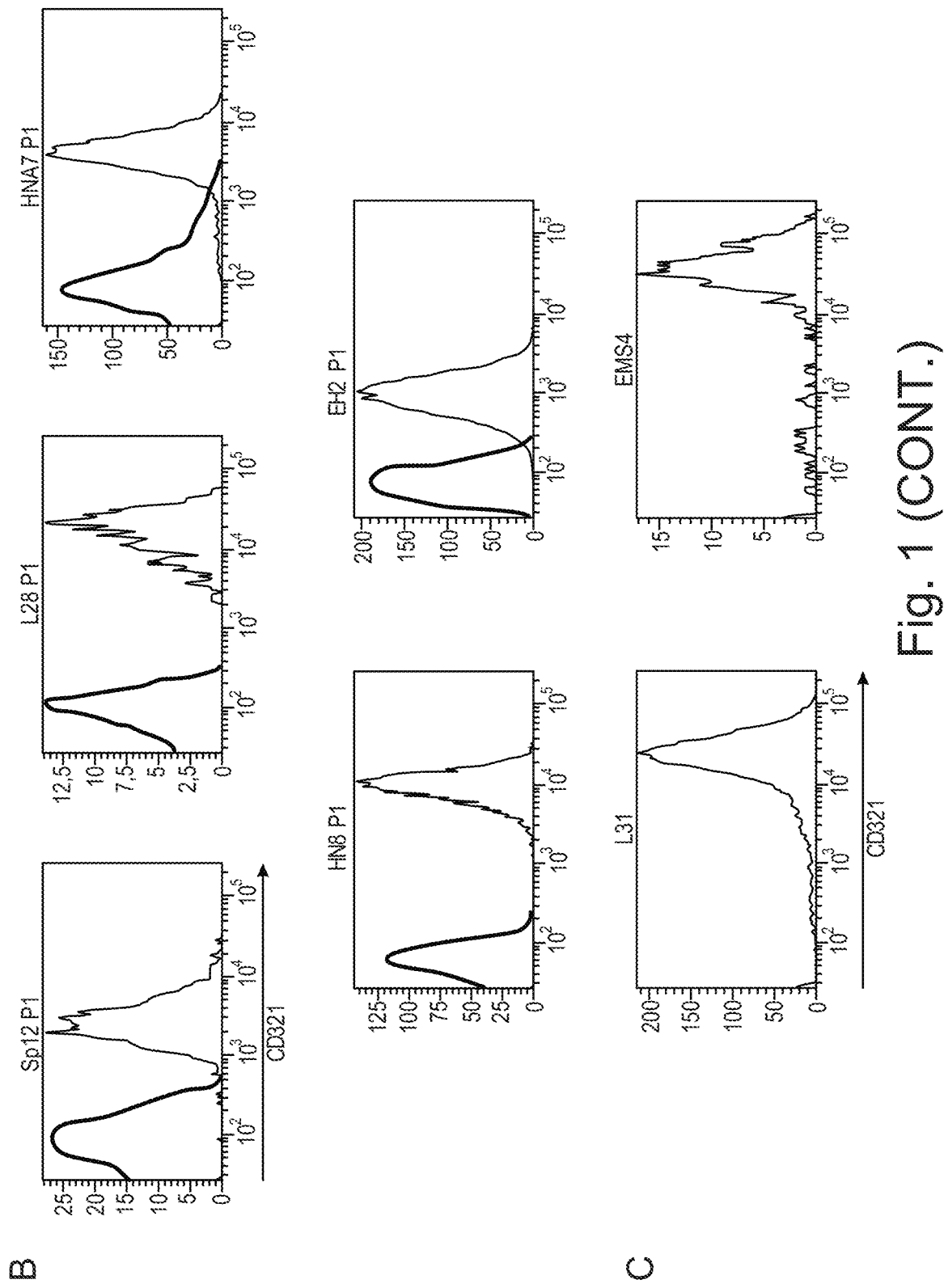

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of", which enjoy well-established meanings in patent terminology.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the terms "one or more" or "at least one", such as one or more members or at least one member of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members. In another example, "one or more" or "at least one" may refer to 1, 2, 3, 4, 5, 6, 7 or more.

The discussion of the background to the invention herein is included to explain the context of the invention. This is not to be taken as an admission that any of the material referred to was published, known, or part of the common general knowledge in any country as of the priority date of any of the claims.

Throughout this disclosure, various publications, patents and published patent specifications are referenced by an identifying citation. All documents cited in the present specification are hereby incorporated by reference in their entirety. In particular, the teachings or sections of such documents herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the invention. When specific terms are defined in connection with a particular aspect of the invention or a particular embodiment of the invention, such connotation is meant to apply throughout this specification, i.e., also in the context of other aspects or embodiments of the invention, unless otherwise defined.

In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous.

Reference throughout this specification to "one embodiment", "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

As corroborated by the experimental section, which illustrates certain representative embodiments of the invention, the inventors identified CD321 as a practically universal or global marker of tumor cells, and particularly as a dependable marker for detection of CTCs and for in situ detection of cancers.

Accordingly, in an aspect, the invention provides a method for detecting or quantifying tumor cells in a biological sample from a subject comprising detecting the expression of CD321 by tumor cells in the biological sample.

A further aspect provides a method for isolating tumor cells from a biological sample from a subject, the method comprising detecting the expression of CD321 by tumor cells in the biological sample and isolating the CD321 expressing tumor cells from the biological sample.

Also provided is thus use of CD321 as a biomarker for tumor cells, particularly as a biomarker useful for detecting or quantifying tumor cells in a biological sample from a subject or for isolating tumor cells from a biological sample from a subject.

Another aspect provides a method for detecting or quantifying circulating tumor cells (CTCs) in a biological sample from a subject comprising detecting the expression of CD321 by circulating non-hematopoietic cells in the biological sample, wherein the expression of CD321 by a circulating non-hematopoietic cell identifies said cell as a circulating tumor cell.

A further aspect provides a method for isolating CTCs from a biological sample from a subject comprising detecting the expression of CD321 by circulating non-hematopoietic cells in the biological sample, wherein the expression of CD321 by a circulating non-hematopoietic cell identifies said cell as a circulating tumor cell, and isolating the CD321 expressing CTCs from the biological sample.

Also provided is thus use of CD321 as a biomarker for CTCs, particularly as a biomarker useful for detecting or quantifying CTCs in a biological sample from a subject or for isolating CTCs from a biological sample from a subject.

A further aspect provides a method for the diagnosis, prognosis or monitoring of a neoplastic disease in a subject, comprising detecting or quantifying tumor cells or CTCs in the subject by any one of the aforementioned methods for detecting or quantifying tumor cells or CTCs in biological samples.

A further aspect provides a method for determining the metastatic potential of a neoplastic disease in a subject comprising detecting or quantifying tumor cells or CTCs in the subject by any one of the aforementioned methods for detecting or quantifying tumor cells or CTCs in biological samples, wherein the presence of tumor cells or CTCs in the subject identifies the neoplastic disease as having metastatic potential.

A further aspect provides a method for determining the relapse of a neoplastic disease in a subject comprising detecting or quantifying tumor cells or CTCs in the subject by any one of the aforementioned methods for detecting or quantifying tumor cells or CTCs in biological samples, wherein the presence of tumor cells or CTCs in the subject identifies that the neoplastic disease has relapsed.

A further aspect provides a method for determining whether a subject is in need of an anti-cancer therapy, comprising detecting or quantifying tumor cells or CTCs in the subject by any one of the aforementioned methods for detecting or quantifying tumor cells or CTCs in biological samples, wherein the presence of tumor cells or CTCs in the subject identifies the subject as being in need of an anti-cancer therapy.

A further aspect provides a method for determining the efficacy of an anti-cancer therapy in a subject having a neoplastic disease, comprising detecting or quantifying tumor cells or CTCs in the subject by any one of the aforementioned methods for detecting or quantifying tumor cells or CTCs in biological samples before and during or subsequent to the therapy, wherein reduced quantity of tumor cells or CTCs (e.g., as measured per given weight or volume of a sample) in the subject during or subsequent to the therapy compared to before the therapy identifies said therapy as efficacious.

The present methods for detecting or quantifying tumor cells or CTCs allow to determine, measure, demonstrate, conclude or confirm the presence or absence of said tumor cells or CTCs in biological samples. The methods may provide for a qualitative outcome—for example, the conclusion that tumor cells or CTCs are 'present' vs. 'absent' or 'detected' vs. 'not detected' in a sample. The methods may also provide for a quantitative outcome—for example, the total number of tumor cells or CTCs detected in a sample, the number of tumor cells or CTCs detected per given weight or volume of a sample, or the fraction of tumor cells or CTCs vs. all (nucleated) cells comprised by a sample.

The present methods may also allow to isolate tumor cells or CTCs from biological samples. The term "isolating" as used throughout this specification with reference to a particular component (e.g., tumor cells or CTCs) of a composition or mixture (e.g., a biological sample) encompasses processes or techniques whereby such component is separated from one or more or (substantially) all other components of the composition or mixture. The term does not require absolute purity. Instead, isolating the component will produce a discrete environment in which the abundance of the component relative to one or more or all other components is greater than in the starting composition or mixture. A discrete environment may denote a single medium, such as for example a single solution, dispersion, gel, precipitate, etc. Isolating tumor cells or CTCs from a biological sample may thus particularly increase the abundance of the tumor cells or CTCs relative to all other cells comprised in the biological sample. By means of an example, isolating the tumor cells or CTCs from the biological sample may yield a cell population, in which the tumor cells or CTCs constitute at least 50% (by number) of all cells of said cell population, for example, at least 55%, preferably at least 60% or at least 65%, more preferably at least 70% or at least 75%, more preferably at least 80% or at least 85%, and more preferably at least 90% or at least 95%, and even more preferably at least 96%, at least 97%, at least 98%, at least 99%, or even 100% of all cells of said cell population.

The acts of detecting, quantifying or isolating tumor cells or CTCs may be performed separately or in any combination (sequentially or simultaneously) or may be inseparable. By means of an example, a method configured to quantify tumor cells or CTCs in a sample also necessarily detects the presence or absence of said tumor cells or CTCs in the sample. In another example, a method configured to isolate tumor cells or CTCs from a sample also necessarily detects the presence or absence of said tumor cells or CTCs in the sample and may optionally allow to quantify the isolated tumor cells or CTCs.

The term "neoplastic disease" generally refers to any disease or disorder characterized by neoplastic cell growth and proliferation, whether benign (not invading surrounding normal tissues, not forming metastases), pre-malignant (precancerous), or malignant (invading adjacent tissues and capable of producing metastases). The term neoplastic disease generally includes all transformed cells and tissues and all cancerous cells and tissues. Neoplastic diseases or disorders include, but are not limited to abnormal cell growth, benign tumors, premalignant or precancerous lesions, malignant tumors, and cancer. Examples of neoplastic diseases or disorders are benign, pre-malignant, or malignant neoplasms located in any tissue or organ, such as in the prostate, colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, or urogenital tract.

As used herein, the terms "tumor" or "tumor tissue" refer to an abnormal mass of tissue that results from excessive cell division. A tumor or tumor tissue comprises tumor cells which are neoplastic cells with abnormal growth properties and no useful bodily function. Tumors, tumor tissue and tumor cells may be benign, pre-malignant or malignant, or may represent a lesion without any cancerous potential. A tumor or tumor tissue may also comprise tumor-associated non-tumor cells, e.g., vascular cells which form blood vessels to supply the tumor or tumor tissue. Non-tumor cells may be induced to replicate and develop by tumor cells, for example, the induction of angiogenesis in a tumor or tumor tissue.

As used herein, the term "cancer" refers to a malignant neoplasm characterized by deregulated or unregulated cell growth. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor). The term "metastatic" or "metastasis" generally refers to the spread of a cancer from one organ or tissue to another non-adjacent organ or tissue. The occurrence of the neoplastic disease in the other non-adjacent organ or tissue is referred to as metastasis.

Examples of cancer include but are not limited to carcinoma, lymphoma, blastoma, sarcoma, and leukemia or lymphoid malignancies. More particular examples of such cancers include without limitation: squamous cell cancer (e.g., epithelial squamous cell cancer), lung cancer including small-cell lung cancer, non-small cell lung cancer, adenocarcinoma of the lung, squamous carcinoma of the lung and large cell carcinoma of the lung, cancer of the peritoneum, hepatocellular cancer, gastric or stomach cancer including gastrointestinal cancer, pancreatic cancer, glioma, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulvar cancer, thyroid cancer, hepatic carcinoma, anal carcinoma, penile carcinoma, as well as CNS cancer, melanoma, head and neck cancer, bone cancer, bone marrow cancer, duodenum cancer, esophageal cancer, thyroid cancer, or hematological cancer.

Other non-limiting examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Urethra, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Glioblastoma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Non-melanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumour, Ovarian Low Malignant Potential Tumor, Pancreatic Cancer, Paraproteinemias, Purpura, Parathyroid Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Urethra Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Urethra, Transitional Renal Pelvis and Urethra Cancer, Trophoblastic Tumours, Urethra and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, or Wilms' Tumour.

In certain preferred embodiments, the tumor is a solid tumor. Solid tumors encompass any tumors forming a neoplastic mass that usually does not contain cysts or liquid areas. Solid tumors may be benign, pre-malignant or malignant. Examples of solid tumors are carcinomas, sarcomas, melanomas and lymphomas. Leukemias generally do not form solid tumors. Hence, in certain embodiments, the tumor may be a tumor other than leukemia. Solid tumors also encompass metastases originated from solid tumors.

In certain preferred embodiments, the tumor, such as a solid tumor, including any metastases of the tumor, such as any metastases of a solid tumor, is of epithelial, mesenchymal or melanocyte origin.

Tumors of epithelial origin include any tumors originated from epithelial tissue in any of several sites, such as without limitation skin, lung, intestine, colon, breast, bladder, head and neck (including lips, oral cavity, salivary glands, nasal cavity, nasopharynx, paranasal sinuses, pharynx, throat, larynx, and associated structures), esophagus, thyroid, kidney, liver, pancreas, bladder, penis, testes, prostate, vagina, cervix, or anus.

In certain preferred embodiments, the tumor may be a carcinoma, including any malignant neoplasm originated from epithelial tissue in any of several sites, such as without limitation skin, lung, intestine, colon, breast, bladder, head and neck (including lips, oral cavity, salivary glands, nasal cavity, nasopharynx, paranasal sinuses, pharynx, throat, larynx, and associated structures), esophagus, thyroid, kidney, liver, pancreas, bladder, penis, testes, prostate, vagina, cervix, or anus.

In certain preferred embodiments, the tumor may be a squamous cell carcinoma (SCC). SCC may include without limitation SCC originated from skin, head and neck (including lips, oral cavity, salivary glands, nasal cavity, nasopharynx, paranasal sinuses, pharynx, throat, larynx, and associated structures), thyroid, esophagus, lung, penis, prostate, vagina, cervix, anus, or bladder.

Tumors of mesenchymal origin include any tumors originated from mesenchymal tissue in any of several sites, such as without limitation bone, cartilage, fat, muscle, blood vessels, fibrous tissue, or other connective or supportive tissue.

In certain preferred embodiments, the tumor may be a sarcoma, including any malignant neoplasm originated from mesenchymal tissue in any of several sites, such as without limitation bone, cartilage, fat, muscle, blood vessels, fibrous tissue, or other connective or supportive tissue.

Tumors of melanocyte origin include any tumors originated from melanocytes in any of several sites, such as without limitation skin, mouth, eyes, or small intestine.

In certain preferred embodiments, the tumor may be a melanoma, including any malignant neoplasm originated from melanocytes in any of several sites, such as without limitation skin, mouth, eyes, or small intestine.

In certain preferred embodiments, the tumor may be selected from the group comprising or consisting of skin cancer, preferably cutaneous squamous cell carcinoma; lung cancer, preferably lung squamous cell carcinoma or lung pleomorphic carcinoma; head and neck cancer; mammary gland cancer; and esophagus cancer.

The term "tumor cell" as used throughout this specification thus broadly encompasses any neoplastic cell, whether benign, pre-malignant (pre-cancerous) or malignant. The term encompasses inter alia cancer cells, including primary and secondary malignant cells, circulating tumor cells (CTCs), disseminated tumor cells (DTCs), and metastatic tumor cells.

The term "circulating tumor cell" or "CTC" denotes any tumor cell that has shed from a tumor, such as from a primary tumor, into the circulatory system or into an exudate or a secretory fluid. In certain embodiments, CTCs may shed from a tumor into the circulatory system, such as into vasculature or lymphatic system. Circulatory fluids such as blood or lymph may carry CTCs around the body as single cells or as clusters of cells. Hence, CTCs may be present in blood or lymph or may be present in urine, feces or other exudates or secretory fluids. CTCs or a fraction of CTCs can be capable of entering distant sites and persisting in secondary organs as disseminated tumor cells (DTCs). DTCs or a fraction of DTCs can be capable of progressing toward metastases in the secondary organs.

The terms "sample" or "biological sample" as used throughout this specification include any biological specimen obtained (isolated, removed) from a subject. Samples may include without limitation organ tissue (e.g., primary or metastatic tumor tissue), whole blood, plasma, serum, whole blood cells, red blood cells, white blood cells (e.g., peripheral blood mononuclear cells), saliva, urine, stool (feces), tears, sweat, sebum, nipple aspirate, ductal lavage, tumor exudates, synovial fluid, cerebrospinal fluid, pleural fluid such as pleural effusion fluid, peritoneal cavity fluid such as ascites fluid, lymph, fine needle aspirate, amniotic fluid, any other bodily fluid, exudate or secretory fluid, cell lysates, cellular secretion products, inflammation fluid, semen and vaginal secretions. Preferably, a sample may be readily obtainable by non-invasive or minimally invasive methods, such as blood collection ('liquid biopsy'), urine collection, feces collection, tissue (e.g., tumor tissue) biopsy or fine-needle aspiration, such as pleural fluid sampling or peritoneal fluid sampling, allowing the provision/removal/isolation of the sample from a subject. The term "tissue" as used herein encompasses all types of cells of the human body including cells of organs but also including blood and other body fluids recited above. The tissue may be healthy or affected by pathological alterations, e.g., tumor tissue. The tissue may be from a living subject or may be cadaveric tissue.

Particularly useful samples are those known to comprise, or expected or predicted to comprise, or known to potentially comprise, or expected or predicted to potentially comprise tumor cells. Further particularly useful samples are those known to comprise, or expected or predicted to comprise, or known to potentially comprise, or expected or predicted to potentially comprise circulating cells. Further particularly useful samples are those known to comprise, or expected or predicted to comprise, or known to potentially comprise, or expected or predicted to potentially comprise circulating tumor cells.

In further useful embodiments, tumor cells, particularly solid tumor cells, outside of a primary tumor site may be detected or quantified. For example, a sample may be obtained from tissues other than the primary (solid) tumor site. By means of example and not limitation, tumor cells, particularly solid tumor cells, may be detected or quantified in cerebrospinal fluid, in pleural fluid such as pleural effusion fluid, or in peritoneal cavity fluid such as ascites fluid. In certain embodiments, the presence of tumor cells outside of a primary tumor site, such as in the aforementioned fluid samples, may identify the neoplastic disease in the subject as having metastatic potential.

Any suitable weight or volume of a sample may be removed from a subject for analysis. Without limitation, a liquid sample may have a volume between 1 mL and 20 mL, e.g., 5 mL, 7.5 mL, 10 mL, 15 mL or 20 mL. A solid sample may have a weight of between 1 g and 20 g, e.g., 5 g, 7.5 g, 10 g, 15 g or 20 g.

In certain preferred embodiments, the biological sample is a tissue biopsy or tissue fine-needle aspirate. In other preferred embodiments, the biological sample is resected tissue.

In certain preferred embodiments, the biological sample is tumor biopsy or tumor fine-needle aspirate, for example biopsy or fine-needle aspirate from primary or metastatic tumor tissue. In other preferred embodiments, the biological sample is resected tumor tissue, e.g., resected primary or metastatic tumor tissue.

In further preferred embodiments, the biological sample comprises circulating cells. In certain preferred embodiments, the biological sample comprises circulating cells from blood, urine, feces, lymph, or from another exudate or secretory fluid. In particularly preferred embodiments, the biological sample comprises circulating cells from peripheral blood.

In certain preferred embodiments, the biological sample comprises circulating tumor cells. In certain preferred embodiments, the biological sample comprises circulating tumor cells from blood, urine, feces, lymph, or from another exudate or secretory fluid. In particularly preferred embodiments, the biological sample comprises circulating tumor cells from peripheral blood.

The terms "subject", "individual" or "patient" are used interchangeably throughout this specification, and typically and preferably denote humans, but may also encompass reference to non-human animals, preferably warm-blooded animals, even more preferably mammals, such as, e.g., non-human primates, rodents, canines, felines, equines, ovines, porcines, and the like. The term "non-human animals" includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In certain embodiments, the subject is a non-human mammal. In certain preferred embodiments, the subject is human. In other embodiments, the subject is an experimental animal or animal substitute as a disease model. The term does not denote a particular age or sex. Thus, adult and newborn subjects, as well as fetuses, whether male or female, are intended to be covered. Examples of subjects include humans, dogs, cats, cows, goats, and mice. The term subject is further intended to include transgenic species.

Suitable subjects may include without limitation subjects presenting to a physician for a screening for a neoplastic disease, subjects presenting to a physician with symptoms and signs indicative of a neoplastic disease, subjects diagnosed with a neoplastic disease, subjects who have received anti-cancer therapy, subjects undergoing anti-cancer treatment, and subjects having a neoplastic disease is in remission.

Hence, a tumor cell as intended herein may be an animal cell, preferably a warm-blooded animal cell, more preferably a vertebrate cell, yet more preferably a mammalian cell, including humans and non-human mammals, and in certain particularly preferred embodiments a human cell.

Cells such as tumor cells or circulating tumor cells as disclosed herein may in the context of the present specification be said to "comprise the expression" or conversely to "not express" one or more markers, such as one or more genes, polypeptides or proteins, such as CD321, or be described as "positive" (+) or conversely as "negative" (−) for one or more markers, such as one or more genes, polypeptides or proteins, such as CD321.

Such terms are commonplace and well-understood by the skilled person when characterizing cell phenotypes. By means of additional guidance, when a cell is said to be positive for or to express or comprise expression of a given marker, such as a given gene, polypeptide or protein, such as CD321, a skilled person would conclude the presence or evidence of a distinct signal for the marker when carrying out a measurement capable of detecting or quantifying the marker in or on the cell. Suitably, the presence or evidence of the distinct signal for the marker would be concluded based on a comparison of the measurement result obtained for the cell to a result of the same measurement carried out for a negative control (for example, a cell known to not express the marker) and/or a positive control (for example, a cell known to express the marker). Where the measurement method allows for a quantitative assessment of the marker, a positive cell may generate a signal for the marker that is at least 1.5-fold higher than a signal generated for the marker by a negative control cell or than an average signal generated for the marker by a population of negative control cells, e.g., at least 2-fold, at least 4-fold, at least 10-fold, at least 20-fold, at least 30-fold, at least 40-fold, at least 50-fold higher or even higher. Further, a positive cell may generate a signal for the marker that is 3.0 or more standard deviations, e.g., 3.5 or more, 4.0 or more, 4.5 or more, or 5.0 or more standard deviations, higher than an average signal generated for the marker by a population of negative control cells.

The term "marker" is widespread in the art and commonly broadly denotes a biological molecule, more particularly an endogenous biological molecule, and/or a detectable portion thereof, whose qualitative and/or quantitative evaluation in a tested object (e.g., in or on a cell, cell population, tissue, organ, or organism, e.g., in a biological sample of a subject) is predictive or informative with respect to one or more aspects of the tested object's phenotype and/or genotype. The terms "marker" and "biomarker" may be used interchangeably throughout this specification.

Preferably, markers as intended herein may be peptide-, polypeptide- and/or protein-based, or may be nucleic acid-based. For example, a marker may be comprised of peptide(s), polypeptide(s) and/or protein(s) encoded by a given gene, or of detectable portions thereof. Further, whereas the term "nucleic acid" generally encompasses DNA, RNA and DNA/RNA hybrid molecules, in the context of markers the term may typically refer to heterogeneous nuclear RNA (hnRNA), pre-mRNA, messenger RNA (mRNA), or copy DNA (cDNA), or detectable portions thereof. Such nucleic acid species are particularly useful as markers, since they contain qualitative and/or quantitative information about the expression of the gene. Particularly preferably, a nucleic acid-based marker may encompass mRNA of a given gene, or cDNA made of the mRNA, or detectable portions thereof.

The term "protein" as used throughout this specification generally encompasses macromolecules comprising one or more polypeptide chains, i.e., polymeric chains of amino acid residues linked by peptide bonds. The term may encompass naturally, recombinantly, semi-synthetically or synthetically produced proteins. The term also encompasses proteins that carry one or more co- or post-expression-type modifications of the polypeptide chain(s), such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes protein variants or mutants which carry amino acid sequence variations vis-à-vis a corresponding native proteins, such as, e.g., amino acid deletions, additions and/or substitutions. The term contemplates both full-length proteins and protein parts or fragments, e.g., naturally-occurring protein parts that ensue from processing of such full-length proteins.

The term "polypeptide" as used throughout this specification generally encompasses polymeric chains of amino acid residues linked by peptide bonds. Hence, insofar a protein is only composed of a single polypeptide chain, the terms "protein" and "polypeptide" may be used interchangeably herein to denote such a protein. The term is not limited to any minimum length of the polypeptide chain. The term may encompass naturally, recombinantly, semi-synthetically or synthetically produced polypeptides. The term also encompasses polypeptides that carry one or more co- or post-expression-type modifications of the polypeptide chain, such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes polypeptide variants or mutants which carry amino acid sequence variations vis-à-vis a corresponding native polypeptide, such as, e.g., amino acid deletions, additions and/or substitutions. The term contemplates both full-length polypeptides and polypeptide parts or fragments, e.g., naturally-occurring polypeptide parts that ensue from processing of such full-length polypeptides.

The term "peptide" as used throughout this specification preferably refers to a polypeptide as used herein consisting essentially of 50 amino acids or less, e.g., 45 amino acids or less, preferably 40 amino acids or less, e.g., 35 amino acids or less, more preferably 30 amino acids or less, e.g., 25 or less, 20 or less, 15 or less, 10 or less or 5 or less amino acids.

The term "nucleic acid" as used throughout this specification typically refers to a polymer (preferably a linear polymer) of any length composed essentially of nucleoside units. A nucleoside unit commonly includes a heterocyclic base and a sugar group. Heterocyclic bases may include inter alia purine and pyrimidine bases such as adenine (A), guanine (G), cytosine (C), thymine (T) and uracil (U) which are widespread in naturally-occurring nucleic acids, other naturally-occurring bases (e.g., xanthine, inosine, hypoxanthine) as well as chemically or biochemically modified (e.g., methylated), non-natural or derivatised bases. Exemplary modified nucleobases include without limitation 5-substituted pyrimidines, 6-azapyrimidines and N-2, N-6 and O-6 substituted purines, including 2-aminopropyladenine, 5-propynyluracil and 5-propynylcytosine. In particular, 5-methylcytosine substitutions have been shown to increase nucleic acid duplex stability and may be preferred base substitutions in for example antisense agents, even more particularly when combined with 2'-O-methoxyethyl sugar modifications. Sugar groups may include inter alia pentose (pentofuranose) groups such as preferably ribose and/or 2-deoxyribose common in naturally-occurring nucleic acids, or arabinose, 2-deoxyarabinose, threose or hexose sugar groups, as well as modified or substituted sugar groups (such as without limitation 2'-O-alkylated, e.g., 2'-O-methylated or 2'-O-ethylated sugars such as ribose; 2'-O-alkyloxyalkylated, e.g., 2'-O-methoxyethylated sugars such as ribose; or 2'-O,4'-C-alkylene-linked, e.g., 2'-O,4'-C-methylene-linked or 2'-O,4'-C-ethylene-linked sugars such as ribose; 2'-fluoroarabinose, etc.). Nucleoside units may be linked to one another by any one of numerous known inter-nucleoside linkages, including inter alia phosphodiester linkages common in naturally-occurring nucleic acids, and further modified phosphate- or phosphonate-based linkages such as phosphorothioate, alkyl phosphorothioate such as methyl phosphorothioate, phosphorodithioate, alkylphosphonate such as methylphosphonate, alkylphosphonothioate, phosphotriester such as alkylphosphotriester, phosphoramidate, phosphoropiperazidate, phosphoromorpholidate, bridged phosphoramidate, bridged methylene phosphonate, bridged phosphorothioate; and further siloxane, carbonate, sulfamate, carboalkoxy, acetamidate, carbamate such as 3'-N-carbamate, morpholino, borano, thioether, 3'-thioacetal, and sulfone internucleoside linkages. Preferably, internucleoside linkages may be phosphate-based linkages including modified phosphate-based linkages, such as more preferably phosphodiester, phosphorothioate or phosphorodithioate linkages or combinations thereof. The term "nucleic acid" also encompasses any other nucleobase containing polymers such as nucleic acid mimetics, including, without limitation, peptide nucleic acids (PNA), peptide nucleic acids with phosphate groups (PHONA), locked nucleic acids (LNA), morpholino phosphorodiamidate-backbone nucleic acids (PMO), cyclohexene nucleic acids (CeNA), tricyclo-DNA (tcDNA), and nucleic acids having backbone sections with alkyl linkers or amino linkers (see, e.g., Kurreck 2003 (Eur J Biochem 270: 1628-1644)). "Alkyl" as used herein particularly encompasses lower hydrocarbon moieties, e.g., C1-C4 linear or branched, saturated or unsaturated hydrocarbon, such as methyl, ethyl, ethenyl, propyl, 1-propenyl, 2-propenyl, and isopropyl. Nucleic acids as intended herein may include naturally occurring nucleosides, modified nucleosides or mixtures thereof. A modified nucleoside may include a modified heterocyclic base, a modified sugar moiety, a modified inter-nucleoside linkage or a combination thereof. The term "nucleic acid" further preferably encompasses DNA, RNA and DNA/RNA hybrid molecules, specifically including hnRNA, pre-mRNA, mRNA, cDNA, genomic DNA, amplification products, oligonucleotides, and synthetic (e.g., chemically synthesised) DNA, RNA or DNA/RNA hybrids. A nucleic acid can be naturally occurring, e.g., present in or isolated from nature, can be recombinant, i.e., produced by recombinant DNA technology, and/or can be, partly or entirely, chemically or biochemically synthesised. A "nucleic acid" can be double-stranded, partly double stranded, or single-stranded. Where single-stranded, the nucleic acid can be the sense strand or the antisense strand. In addition, nucleic acid can be circular or linear.

The reference to any marker, including any peptide, polypeptide, protein, or nucleic acid, corresponds to the marker commonly known under the respective designations in the art. The terms encompass such markers of any organism where found, and particularly of animals, preferably warm-blooded animals, more preferably vertebrates, yet more preferably mammals, including humans and non-human mammals, still more preferably of humans.

The terms particularly encompass such markers, including any peptides, polypeptides, proteins, or nucleic acids, with a native sequence, i.e., ones of which the primary sequence is the same as that of the markers found in or derived from nature. A skilled person understands that native sequences may differ between different species due to genetic divergence between such species. Moreover, native sequences may differ between or within different individuals of the same species due to normal genetic diversity (variation) within a given species. Also, native sequences may differ between or even within different individuals of the same species due to somatic mutations, or post-transcriptional or post-translational modifications. Any such variants or isoforms of markers are intended herein. Accordingly, all sequences of markers found in or derived from nature are considered "native". The terms encompass the markers when forming a part of a living organism, organ, tissue or cell, when forming a part of a biological sample, as well as when at least partly isolated from such sources. The terms also encompass markers when produced by recombinant or synthetic means.

In certain embodiments, markers, including any peptides, polypeptides, proteins, or nucleic acids, may be human, i.e., their primary sequence may be the same as a corresponding primary sequence of or present in a naturally occurring human markers. Hence, the qualifier "human" in this connection relates to the primary sequence of the respective markers, rather than to their origin or source. For example, such markers may be present in or isolated from samples of human subjects or may be obtained by other means (e.g., by recombinant expression, cell-free transcription or translation, or non-biological nucleic acid or peptide synthesis).

Unless otherwise apparent from the context, reference herein to any marker, peptide, polypeptide, protein, or nucleic acid, or fragment thereof may generally also encompass modified forms of said marker, peptide, polypeptide, protein, or nucleic acid, or fragment thereof, such as bearing post-expression modifications including, for example, phosphorylation, glycosylation, lipidation, methylation, cysteinylation, sulphonation, glutathionylation, acetylation, oxidation of methionine to methionine sulphoxide or methionine sulphone, and the like.

The reference herein to any marker, including any peptide, polypeptide, protein, or nucleic acid, also encompasses fragments thereof. Hence, the reference herein to measuring (or measuring the quantity of) any one marker may encompass measuring the marker and/or measuring one or more fragments thereof.

For example, any marker and/or one or more fragments thereof may be measured collectively, such that the measured quantity corresponds to the sum amounts of the collectively measured species. In another example, any marker and/or one or more fragments thereof may be measured each individually.

The term "fragment" as used throughout this specification with reference to a peptide, polypeptide, or protein generally denotes a portion of the peptide, polypeptide, or protein, such as typically an N- and/or C-terminally truncated form of the peptide, polypeptide, or protein. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the amino acid sequence length of said peptide, polypeptide, or protein. For example, insofar not exceeding the length of the full-length peptide, polypeptide, or protein, a fragment may include a sequence of ≥5 consecutive amino acids, or ≥10 consecutive amino acids, or ≥20 consecutive amino acids, or ≥30 consecutive amino acids, e.g., ≥40 consecutive amino acids, such as for example ≥50 consecutive amino acids, e.g., ≥60, ≥70, ≥80, ≥90, ≥100, ≥200, ≥300, ≥400, ≥500 or ≥600 consecutive amino acids of the corresponding full-length peptide, polypeptide, or protein.

The term "fragment" with reference to a nucleic acid (polynucleotide) generally denotes a 5'- and/or 3'-truncated form of a nucleic acid. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the nucleic acid sequence length of said nucleic acid. For example, insofar not exceeding the length of the full-length nucleic acid, a fragment may include a sequence of ≥5 consecutive nucleotides, or ≥10 consecutive nucleotides, or ≥20 consecutive nucleotides, or ≥30 consecutive nucleotides, e.g., ≥40 consecutive nucleotides, such as for example ≥50 consecutive nucleotides, e.g., ≥60, ≥70, ≥80, ≥90, ≥100, ≥200, ≥300, ≥400, ≥500 or ≥600 consecutive nucleotides of the corresponding full-length nucleic acid.

The terms encompass fragments arising by any mechanism, in vivo and/or in vitro, such as, without limitation, by alternative transcription or translation, exo- and/or endo-proteolysis, exo- and/or endo-nucleolysis, or degradation of the peptide, polypeptide, protein, or nucleic acid, such as, for example, by physical, chemical and/or enzymatic proteolysis or nucleolysis.

The present specification teaches CD321 as a useful marker of cancer cells. As mentioned, CD321 marker may preferably be peptide-, polypeptide- and/or protein-based, or nucleic acid-based. In certain preferred embodiments, detecting the expression of CD321 as taught herein comprises detecting CD321 protein or CD321 mRNA or both.

The reference to "CD321" denotes the CD321 marker, peptide, polypeptide, protein, or nucleic acid, as commonly known under said designation in the art. By means of additional guidance, CD321 is also known as junctional adhesion molecule A, JAM-A, junctional adhesion molecule 1, JAM-1, platelet F11 receptor, F11R, platelet adhesion molecule 1, and PAM-1. The CD321-encoding gene is also known under designations F11R, JAM1, and JCAM.

By means of an example, human F11R mRNA sequence is annotated under NCBI Genbank accession number NM_016946.4. Nucleotides 271 (start codon) to 1170 (stop codon) of NM_016946.4 constitute the CD321 coding sequence and are reproduced here below (SEQ ID NO: 1):

ATGGGGACAAAGGCGCAAGTCGAGAGGAAACTGTTGTGCCTCTTCATATT

GGCGATCCTGTTGTGCTCCCTGGCATTGGGCAGTGTTACAGTGCACTCTT

CTGAACCTGAAGTCAGAATTCCTGAGAATAATCCTGTGAAGTTGTCCTGT

GCCTACTCGGGCTTTTCTTCTCCCCGTGTGGAGTGGAAGTTTGACCAAGG

AGACACCACCAGACTCGTTTGCTATAATAACAAGATCACAGCTTCCTATG

AGGACCGGGTGACCTTCTTGCCAACTGGTATCACCTTCAAGTCCGTGACA

CGGGAAGACACTGGGACATACACTTGTATGGTCTCTGAGGAAGGCGGCAA

CAGCTATGGGGAGGTCAAGGTCAAGCTCATCGTGCTTGTGCCTCCATCCA

AGCCTACAGTTAACATCCCCTCCTCTGCCACCATTGGGAACCGGGCAGTG

CTGACATGCTCAGAACAAGATGGTTCCCCACCTTCTGAATACACCTGGTT

CAAAGATGGGATAGTGATGCCTACGAATCCCAAAAGCACCCGTGCCTTCA

GCAACTCTTCCTATGTCCTGAATCCCACAACAGGAGAGCTGGTCTTTGAT

CCCCTGTCAGCCTCTGATACTGGAGAATACAGCTGTGAGGCACGGAATGG

GTATGGGACACCCATGACTTCAAATGCTGTGCGCATGGAAGCTGTGGAGC

GGAATGTGGGGGTCATCGTGGCAGCCGTCCTTGTAACCCTGATTCTCCTG

GGAATCTTGGTTTTTGGCATCTGGTTTGCCTATAGCCGAGGCCACTTTGA

CAGAACAAAGAAAGGGACTTCGAGTAAGAAGGTGATTTACAGCCAGCCTA

GTGCCCGAAGTGAAGGAGAATTCAAACAGACCTCGTCATTCCTGGTGTGA

By means of an example, human CD321 precursor protein sequence is annotated under NCBI Genbank accession number NP_058642.1 and is reproduced below (SEQ ID NO: 2):

MGTKAQVERKLLCLFILAILLCSLALGSVTVHSSEPEVRIPENNPVKLSC

AYSGFSSPRVEWKFDQGDTTRLVCYNNKITASYEDRVTFLPTGITFKSVT

-continued

```
REDTGTYTCMVSEEGGNSYGEVKVKLIVLVPPSKPTVNIPSSATIGNRAV

LTCSEQDGSPPSEYTWFKDGIVMPTNPKSTRAFSNSSYVLNPTTGELVFD

PLSASDTGEYSCEARNGYGTPMTSNAVRMEAVERNVGVIVAAVLVTLILL

GILVFGIWFAYSRGHFDRTKKGTSSKKVIYSQPSARSEGEFKQTSSFLV
```

A skilled person can appreciate that sequences represented in sequence databases or in the present specification may be of precursors of markers, peptides, polypeptides, proteins, or nucleic acids and may include parts which are processed away from mature molecules. By means of an example, amino acids 1 to 27 of SEQ ID NO: 2 have been shown or predicted to constitute a signal peptide processed away from mature CD321.

A skilled person can appreciate that all CD321 isoforms are included. By means of an example, an alternative splicing isoform of CD321 is known lacking amino acids 81-129 of SEQ ID NO: 3, as represented here below (SEQ ID NO: 3):

```
MGTKAQVERKLLCLFILAILLCSLALGSVTVHSSEPEVRIPENNPVKLSC

AYSGFSSPRVEWKFDQGDTTRLVCYNNKITVPPSKPTVNIPSSATIGNRA

VLTCSEQDGSPPSEYTWFKDGIVMPTNPKSTRAFSNSSYVLNPTTGELVF

DPLSASDTGEYSCEARNGYGTPMTSNAVRMEAVERNVGVIVAAVLVTLIL

LGILVFGIWFAYSRGHFDRTKKGTSSKKVIYSQPSARSEGEFKQTSSFLV
```

By means of an example, mRNA and protein sequences of human CD45, LSP1, CD48, CD36, CD41, CD42a, CD42b, and CD61 are annotated under the following NCBI Genbank accession numbers: CD45 protein (NP_002829.3, NP_563578.2), CD45 mRNA (NM_002838.4, NM_080921.3); LSP1 protein (NP_001013271.1, NP_001013272.1, NP_001013273.1, NP_001229861.1 NP_001275934.1, NP_002330.1); LSP1 mRNA (NM_001013253.1, NM_001013254.1, NM_001013255.1, NM_001242932.1, NM_001289005.1, NM_002339.2); CD48 protein (NP_001769.2); CD48 mRNA (NM_001778.3); CD36 protein (NP_000063.2, NP_001001547.1, NP_001001548.1, NP_001120915.1, NP_001120916.1, NP_001276837.1, NP_001276838.1, NP_001276840.1, XP_005250770.1, XP_005250771.1, XP_005250772.1); CD36 mRNA (NM_000072.3, NM_001001547.2, NM_001001548.2, NM_001127443.1, NM_001127444.1, NM_001289908.1, NM_001289909.1, NM_001289911.1, XM_005250713.1, XM_005250714.1, XM_005250715.4); CD41 protein (NP_000410.2, XP_011523051.1); CD41 mRNA (NM_000419.4, XM_011524749.1); CD42a protein (NP_000165.1, XP_005247431.1, XP_011511003.1, XP_011511004.1); CD42a mRNA (NM_000174.4, XM_005247374.3, XM_011512701.1, XM_011512702.1); CD42b protein (NP_000164.5); CD42b mRNA (NM_000173.6); CD61 protein (NP_000203.2); CD61 mRNA (NM_000212.2).

Certain aspects and embodiments disclosed in the present specification rely on identifying circulating tumor cells (CTCs) in a biological sample, comprising detecting the expression of CD321 by circulating non-hematopoietic cells in the biological sample, wherein the expression of CD321 by a circulating non-hematopoietic cell identifies said cell as a CTC.

The term "circulating cell" denotes any cell present or found in a circulatory fluid or in an exudate or a secretory fluid of a subject. The term may particularly denote cells present or found in a circulatory fluid of a subject, preferably in blood or lymph of a subject, more preferably in blood of a subject, even more preferably in peripheral blood of a subject.

Circulating cells include hematopoietic cells and non-hematopoietic cells. The term "hematopoietic cell" denotes a cell that forms a blood cellular component, more particularly a cell originated from a hematopoietic stem cell or a hematopoietic progenitor cell and/or originated from an erythroid, lymphoid or myeloid lineage. Examples of hematopoietic cells include erythrocytes, leukocytes and thrombocytes.

Conversely, the term "non-hematopoietic cell" broadly encompasses any cell that has not originated from a hematopoietic stem cell or a hematopoietic progenitor cell or has originated from a cell lineage other than the erythroid lineage, lymphoid lineage and myeloid lineage. Examples of non-hematopoietic cells include cells other than erythrocytes, leukocytes and thrombocytes. By means of an example, circulating non-hematopoietic cells may be shed into the circulatory system, such as into blood or lymph, or into an exudate or a secretory fluid from tissues or organs other than blood, hematopoietic tissues and lymphoid tissues.

Circulating cells can be identified or classified as either hematopoietic or non-hematopoietic by any suitable criteria, such as based on evaluation of cell morphology, behavior and/or marker expression. By means of an example, morphologically, erythrocytes (red blood cells) can be identified by their biconcave shape, diameter of about 6-8 µm and lack of cell nucleus; and thrombocytes (platelets) can be identified by their lens shape, greatest diameter of about 2-3 µm, and lack of cell nucleus. By means of an example, erythrocytes can be identified by their comparatively greater susceptibility to lysis in hypotonic solutions, such as in 1×ACK (Ammonium Chloride Potassium) buffer (155 mM $NH_4Cl$, 10 mM $KHCO_3$, 0.1 mM EDTA, pH 7.3), or preferably using classical hypotonic shock to lyse red blood cells (adding a suitable volume of 0.2% w/v NaCl solution in water, allowing about 10-20 seconds until the red blood cells are lysed, and restoring isotonicity by adding the same volume of 1.6% w/v NaCl solution in water), or also preferably using a commercially available BD FACS™M Lysing solution (cat. no 349202;). By means of an example, erythrocytes, leukocytes and platelets can be separated and hence identified by sedimentation of anticoagulated blood, whereby erythrocytes collect in the bottom layer, and leukocytes and platelets collect in buffy coat interposed between the bottom layer and the top plasma layer.

In certain embodiments, leukocytes can be identified by the presence of expression (positivity for) at least one pan-leukocyte marker, such as for example CD45 (protein tyrosine phosphatase, receptor type, C; PTPRC), leukocyte-specific phosphoprotein-1 (LSP1), and/or CD48 (B-lymphocyte activation marker; BLAST-1; signaling lymphocytic activation molecule 2; SLAMF2).

In certain embodiments, thrombocytes can be identified by the presence of expression (positivity for) at least one thrombocyte marker, such as for example CD36 (platelet glycoprotein 4; fatty acid translocase; FAT), CD41 (integrin alpha-IIb; ITGA2B), CD42a (glycoprotein IX (platelet); GP9), CD42b (platelet glycoprotein Ib alpha chain; GP1BA), and/or CD61 (integrin beta-3; ITGB3).

In certain embodiments, a circulating cell which is not an erythrocyte can be identified as a non-hematopoietic cell by the absence of expression of (negativity for) at least one pan-leukocyte marker and at least one thrombocyte marker by said cell.

In certain embodiments, a circulating cell which is not an erythrocyte and not a thrombocyte can be identified as a non-hematopoietic cell by the absence of expression of (negativity for) at least one pan-leukocyte marker by said cell.

In certain embodiments, a circulating cell which is not an erythrocyte and not a leukocyte can be identified as a non-hematopoietic cell by the absence of expression of (negativity for) at least one thrombocyte marker by said cell.

Hence, in certain embodiments, a circulating CD321 positive cell, particularly a circulating CD321 positive tumor cell, is identified as non-hematopoietic by the absence of expression of at least one pan-leukocyte marker by said cell.

In certain embodiments, a circulating CD321 positive cell, particularly a circulating CD321 positive tumor cell, is identified as non-hematopoietic by the absence of expression of at least one pan-leukocyte marker and of at least one thrombocyte marker by said cell.

In certain embodiments, the methods as taught herein may comprise the following steps:
a) providing a biological sample from the subject, said biological sample comprising circulating cells from the subject;
b) detecting in said biological sample non-hematopoietic cells negative for at least one pan-leukocyte marker and negative for at least one thrombocyte marker; and
c) detecting the expression of CD321 by the cells as detected in b), wherein the expression of CD321 by a cell as detected in b) identifies said cell as a circulating tumor cell.

In step a) the biological sample may preferably comprise circulating cells from blood, urine, feces, lymph or another exudate or secretory fluid of the subject, more preferably from peripheral blood of the subject.

In certain embodiments of the methods and uses taught herein, the pan-leukocyte marker is selected from the group consisting of CD45, LSP1, CD48, and combinations thereof.

In certain embodiments of the methods and uses taught herein, the thrombocyte marker is selected from the group consisting of CD36, CD41, CD42a, CD42b, CD61, and combinations thereof.

In certain embodiments of the methods and uses taught herein, the pan-leukocyte marker is selected from the group consisting of CD45, LSP1, CD48, and combinations thereof, and the thrombocyte marker is selected from the group consisting of CD36, CD41, CD42a, CD42b, CD61, and combinations thereof;

In certain preferred embodiments of the methods and uses taught herein, the pan-leukocyte marker is CD45.

In certain preferred embodiments of the methods and uses taught herein, the thrombocyte marker is CD42a.

In certain preferred embodiments of the methods and uses taught herein, the pan-leukocyte marker is CD45 and the thrombocyte marker is CD42a.

A marker, for example a peptide, polypeptide, protein, or nucleic acid, or a group of two or more markers, is "measured" in a tested object (e.g., in or on a cell, cell population, tissue, organ, or organism, e.g., in a biological sample from a subject) when the presence or absence and/or quantity of said marker or said group of markers is detected or determined in the tested object, preferably substantially to the exclusion of other molecules and analytes, e.g., other peptides, polypeptides, proteins, or nucleic acids.

Depending on factors that can be evaluated and decided on by a skilled person, such as inter alia the type of a marker (e.g., peptide, polypeptide, protein, or nucleic acid), the type of the tested object (e.g., a cell, cell population, tissue, organ, or organism, e.g., the type of biological sample of a subject, e.g., whole blood, tissue biopsy), the expected abundance of the marker in the tested object, the type, robustness, sensitivity and/or specificity of the detection method used to detect the marker, etc., the marker may be measured directly in the tested object, or the tested object may be subjected to one or more processing steps aimed at achieving an adequate measurement of the marker.

Any existing, available or conventional separation, detection and/or quantification methods may be used to measure the presence or absence (e.g., readout being present vs. absent; or detectable amount vs. undetectable amount) and/or quantity (e.g., readout being an absolute or relative quantity) of markers in a tested object (e.g., in or on a cell, cell population, tissue, organ, or organism, e.g., in a biological sample from a subject).

In certain examples, such methods may include biochemical assay methods, including inter alia assays of enzymatic activity, membrane channel activity, substance-binding activity, gene regulatory activity, or cell signaling activity of a marker, e.g., peptide, polypeptide, protein, or nucleic acid.

In other examples, such methods may include immunological assay methods, wherein the ability of an assay to separate, detect and/or quantify a marker (such as, preferably, peptide, polypeptide, or protein) is conferred by specific binding between a separable, detectable and/or quantifiable binding agent such as an immunological binding agent (antibody) and the marker Immunological assay methods include without limitation immunohistochemistry, immunocytochemistry, flow cytometry, mass cytometry, fluorescence activated cell sorting (FACS), fluorescence microscopy, fluorescence based cell sorting using microfluidic systems, immunoaffinity adsorption based techniques such as affinity chromatography, magnetic particle separation, magnetic activated cell sorting or bead based cell sorting using microfluidic systems, enzyme-linked immunosorbent assay (ELISA) and ELISPOT based techniques, radioimmunoassay (RIA), Western blot, etc.

In further examples, such methods may include mass spectrometry analysis methods. Generally, any mass spectrometric (MS) techniques that are capable of obtaining precise information on the mass of peptides, and preferably also on fragmentation and/or (partial) amino acid sequence of selected peptides (e.g., in tandem mass spectrometry, MS/MS; or in post source decay, TOF MS), may be useful herein for separation, detection and/or quantification of markers (such as, preferably, peptides, polypeptides, or proteins). Suitable peptide MS and MS/MS techniques and systems are well-known per se (see, e.g., Methods in Molecular Biology, vol. 146: "Mass Spectrometry of Proteins and Peptides", by Chapman, ed., Humana Press 2000, ISBN 089603609x; Biemann 1990. Methods Enzymol 193: 455-79; or Methods in Enzymology, vol. 402: "Biological Mass Spectrometry", by Burlingame, ed., Academic Press 2005, ISBN 9780121828073) and may be used herein. MS arrangements, instruments and systems suitable for biomarker peptide analysis may include, without limitation, matrix-assisted laser desorption/ionisation time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; electrospray ionization mass spectrometry (ESI-MS); ESI-MS/MS; ESI-MS/(MS)$^n$ (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI-(MS)$^n$; atmospheric pressure photoionization mass spectrometry (APPI-MS); APPI-MS/MS; and APPI-(MS)$^n$. Peptide ion fragmentation in tandem MS (MS/MS) arrangements may be achieved using manners established in the art, such as, e.g., collision induced dissociation (CID). Detection and quantification of markers by mass spectrometry may involve multiple reaction monitoring (MRM), such as described among others by Kuhn et al. 2004 (Proteomics 4: 1175-86). MS peptide analysis methods may be advantageously combined with upstream peptide or protein separation or fractionation methods, such as for example with the chromatographic and other methods.

In other examples, such methods may include chromatography methods. The term "chromatography" encompasses methods for separating substances, such as chemical or biological substances, e.g., markers, such as preferably peptides, polypeptides, or proteins, referred to as such and vastly available in the art. In a preferred approach, chromatography refers to a process in which a mixture of substances (analytes) carried by a moving stream of liquid or gas ("mobile phase") is separated into components as a result of differential distribution of the analytes, as they flow around or over a stationary liquid or solid phase ("stationary phase"), between said mobile phase and said stationary phase. The stationary phase may be usually a finely divided solid, a sheet of filter material, or a thin film of a liquid on the surface of a solid, or the like. Chromatography is also widely applicable for the separation of chemical compounds of biological origin, such as, e.g., amino acids, proteins, fragments of proteins or peptides, etc.

Chromatography may be preferably columnar (i.e., wherein the stationary phase is deposited or packed in a column), preferably liquid chromatography, and yet more preferably HPLC. While particulars of chromatography are well known in the art, for further guidance see, e.g., Meyer M., 1998, ISBN: 047198373X, and "Practical HPLC Methodology and Applications", Bidlingmeyer, B. A., John Wiley & Sons Inc., 1993. Exemplary types of chromatography include, without limitation, high-performance liquid chromatography (HPLC), normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immunoaffinity, immobilised metal affinity chromatography, and the like.

Further techniques for separating, detecting and/or quantifying markers, such as preferably peptides, polypeptides, or proteins, may be used, optionally in conjunction with any of the above described analysis methods. Such methods include, without limitation, chemical extraction partitioning, isoelectric focusing (IEF) including capillary isoelectric focusing (CIEF), capillary isotachophoresis (CITP), capillary electrochromatography (CEC), and the like, one-dimensional polyacrylamide gel electrophoresis (PAGE), two-dimensional polyacrylamide gel electrophoresis (2D-PAGE), capillary gel electrophoresis (CGE), capillary zone electrophoresis (CZE), micellar electrokinetic chromatography (MEKC), free flow electrophoresis (FFE), etc.

In certain examples, such methods may include separating, detecting and/or quantifying markers at the nucleic acid level, more particularly RNA level, e.g., at the level of hnRNA, pre-mRNA, mRNA, or cDNA. Standard quantitative RNA or cDNA measurement tools known in the art may be used. Non-limiting examples include hybridisation-based analysis, microarray expression analysis, digital gene expression profiling (DGE), RNA-in-situ hybridisation (RISH), Northern-blot analysis and the like; PCR, RT-PCR, RT-qPCR, end-point PCR, digital PCR or the like; supported oligonucleotide detection, pyrosequencing, polony cyclic sequencing by synthesis, simultaneous bi-directional sequencing, single-molecule sequencing, single molecule real time sequencing, true single molecule sequencing, hybridization-assisted nanopore sequencing, sequencing by synthesis, single-cell RNA sequencing (sc-RNA seq), or the like.

In further examples, any combinations of methods such as discussed herein may be employed.

The cells, such as tumor cells or CTCs specified herein are generally described or characterized with reference to certain marker(s) or combination(s) of markers, such as peptides, polypeptides, proteins, or nucleic acids, expressed or not expressed by the cells, such as in particular CD321-positive tumor cells or CTCs. Accordingly, the present methods for detecting, quantifying or isolating the specified cells may be marker-based, i.e., may involve detection, quantification or isolation of cells expressing or not expressing marker(s) or combination(s) of markers the expression or lack of expression of which is taught herein as typifying or characterizing the specified cells, or may involve detection.

Any existing, available or conventional separation, detection and/or quantification methods may be used to measure the presence or absence (e.g., readout being present vs. absent; or detectable amount vs. undetectable amount) and/or quantity (e.g., readout being an absolute or relative quantity) of the specified cells in, or to isolate the specified cells from, a tested object (e.g., a cell population, tissue, organ, organism, or a biological sample from a subject). Such methods allow to detect, quantify or isolate the specified cells in or from the tested object (e.g., a cell population, tissue, organ, organism, or a biological sample from a subject) substantially to the exclusion of other cells comprised in the tested object. Such methods may allow to detect, quantify or isolate the specified cells with sensitivity of at least 50%, at least 55%, at least 60%, at least 65%, preferably at least 70%, at least 75%, more preferably at least 80%, at least 85%, even more preferably at least 90%, at least 95%, at least 96%, at least 97%, at least 98%, at least 99%, or even 100%, and/or with specificity of at least 50%, at least 55%, at least 60%, at least 65%, preferably at least 70%, at least 75%, more preferably at least 80%, at least 85%, even more preferably at least 90%, at least 95%, at least 96%, at least 97%, at least 98%, at least 99%, or even 100%. By means of example, at least 40% (by number), for example at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of all cells detected, quantified or isolated by such methods may correspond to the specified cells, such as particularly the specified tumor cells or CTCs.

In certain embodiments, methods for detecting, quantifying or isolating the specified cells may comprise treatment(s) or step(s) which diminish or eliminate the viability of the cells. For example, methods which comprise measuring intracellular marker(s) typically necessitate permeabilization of the cell membrane and possibly fixation of the cells; and methods which comprise measuring nucleic acid marker(s) may typically necessitate obtaining nucleic acids (such as particularly RNA, more particularly mRNA) from the cells. In certain other embodiments, methods for detecting, quantifying or isolating the specified cells may substantially preserve the viability of the cells. For example, methods which comprise measuring extracellular or cell surface marker(s) need not disturb the integrity of the cell membrane and may not require fixation/permeabilization of the cells.

In certain embodiments, methods for detecting, quantifying or isolating the specified cells may be single-cell-based, i.e., may allow to discretely detect, quantify or isolate the specified cells as individual cells. In other embodiments, methods for detecting, quantifying or isolating the specified cells may be cell population-based, i.e., may only allow to detect, quantify or isolate the specified cells as a group or collection of cells, without providing information on or allowing to isolate individual cells.

Methods for detecting, quantifying or isolating the specified cells may employ any of the above-described techniques for measuring markers, insofar the separation or the qualitative and/or quantitative measurement of the marker(s) can be correlated with or translated into detection, quantification or isolation of the specified cells. For example, any of the above-described biochemical assay methods, immunological assay methods, mass spectrometry analysis methods, chromatography methods, or nucleic acid analysis method, or combinations thereof for measuring markers, may be employed for detecting, quantifying or isolating the specified cells.

Hence, in certain embodiments, the tumor cells or CTCs are detected, quantified or isolated using a technique selected from the group consisting of flow cytometry, mass cytometry, fluorescence activated cell sorting, fluorescence microscopy, affinity separation, magnetic cell separation, microfluidic separation, and combinations thereof.

Flow cytometry encompasses methods by which individual cells of a cell population are analyzed by their optical properties (e.g., light absorbance, light scattering and fluorescence properties, etc.) as they pass in a narrow stream in single file through a laser beam. Flow cytometry methods include fluorescence activated cell sorting (FACS) methods by which a population of cells having particular optical properties are separated from other cells.

Elemental mass spectrometry-based flow cytometry, or mass cytometry, offers an approach to analyze cells by replacing fluorochrome-labelled binding reagents with mass tagged binding reagents, i.e., tagged with an element or isotope having a defined mass. In these methods, labeled particles are introduced into a mass cytometer, where they are individually atomized and ionized. The individual particles are then subjected to elemental analysis, which identifies and measures the abundance of the mass tags used. The identities and the amounts of the isotopic elements associated with each particle are then stored and analyzed. Due to the resolution of elemental analysis and the number of elemental isotopes that can be used, it is possible to simultaneously measure up to 100 or more parameters on a single particle.

Fluorescence microscopy broadly encompasses methods by which individual cells of a cell population are microscopically analyzed by their fluorescence properties. Fluorescence microscopy approaches may be manual or preferably semi-automated or automated.

Affinity separation also referred to as affinity chromatography broadly encompasses techniques involving specific interactions of cells present in a mobile phase, such as a suitable liquid phase (e.g., cell population in an aqueous suspension) with, and thereby adsorption of the cells to, a stationary phase, such as a suitable solid phase; followed by separation of the stationary phase from the remainder of the mobile phase; and recovery (e.g., elution) of the adsorbed cells from the stationary phase. Affinity separation may be columnar, or alternatively, may entail batch treatment, wherein the stationary phase is collected/separated from the liquid phases by suitable techniques, such as centrifugation or application of magnetic field (e.g., where the stationary phase comprises magnetic substrate, such as magnetic particles or beads). Accordingly, magnetic cell separation is also envisaged herein.

Microfluidic systems allow for accurate and high throughput cell detection, quantification and/or sorting, exploiting a variety of physical principles. Cell sorting on microchips provides numerous advantages by reducing the size of necessary equipment, eliminating potentially biohazardous aerosols, and simplifying the complex protocols commonly associated with cell sorting. The term "microfluidic system" as used throughout this specification broadly refers to systems having one or more fluid microchannels. Microchannels denote fluid channels having cross-sectional dimensions the largest of which are typically less than 1 mm, preferably less than 500 µm, more preferably less than 400 µm, more preferably less than 300 µm, more preferably less than 200 µm, e.g., 100 µm or smaller. Such microfluidic systems can be used for manipulating fluid and/or objects such as droplets, bubbles, capsules, particles, cells and the like. Microfluidic systems may allow for example for fluorescent label-based (e.g., employing fluorophore-conjugated binding agent(s), such as fluorophore-conjugated antibody(ies)), bead-based (e.g., bead-conjugated binding agent(s), such as bead-conjugated antibody(ies)), or label-free cell sorting (reviewed in Shields et al., Lab Chip. 2015, vol. 15: 1230-1249).

In certain embodiments, the aforementioned methods and techniques may employ agent(s) capable of specifically binding to one or more markers, such as peptides, polypeptides, proteins, or nucleic acids, expressed or not expressed by the cells specified herein, such as tumor cells or CTCs.

Hence, in certain embodiments, the techniques employ one or more agents capable of specifically binding to CD321.

In further embodiments, the techniques further employ:
one or more agents capable of specifically binding to the at least one pan-leukocyte marker, such as to at least one marker selected from the group consisting of CD45, LSP1, and CD48, and one or more agents capable of specifically binding to the at least one thrombocyte marker, such as to at least one marker selected from the group consisting of CD36, CD41, CD42a, CD42b, and CD61; or
one or more agents capable of specifically binding to the at least one pan-leukocyte marker, such as to at least one marker selected from the group consisting of CD45, LSP1, and CD48; or
one or more agents capable of specifically binding to the at least one thrombocyte marker, such as to at least one marker selected from the group consisting of CD36, CD41, CD42a, CD42b, and CD61.

Binding agents may be in various forms, e.g., lyophilized, free in solution, or immobilized on a solid phase. They may be, e.g., provided in a multi-well plate or as an array or microarray, or they may be packaged separately, individually, or in combination.

Binding agents as intended throughout this specification may include inter alia antibodies, antibody fragments, antibody-like protein scaffolds, aptamers, spiegelmers (L-aptamers), photoaptamers, proteins, peptides, peptidomimetics, nucleic acids such as oligonucleotides (e.g., hybridization probes or amplification or sequencing primers and primer pairs), small molecules, or combinations thereof.

In certain preferred embodiments, the one or more binding agents are, each independently, one or more antibodies, antibody fragments, antibody-like protein scaffolds, or aptamers.

The term "specifically bind" as used throughout this specification means that an agent (denoted herein also as "binding agent" or "specific-binding agent") binds to one or more desired molecules or analytes (e.g., peptides, polypeptides, proteins, or nucleic acids) substantially to the exclusion of other molecules which are random or unrelated, and optionally substantially to the exclusion of other molecules that are structurally related. The term "specifically bind" does not necessarily require that an agent binds exclusively to its intended target(s). For example, an agent may be said to specifically bind to target(s) of interest if its affinity for such intended target(s) under the conditions of binding is at least about 2-fold greater, preferably at least about 5-fold greater, more preferably at least about 10-fold greater, yet more preferably at least about 25-fold greater, still more preferably at least about 50-fold greater, and even more preferably at least about 100-fold, or at least about 1000-fold, or at least about $10^4$-fold, or at least about $10^5$-fold, or at least about $10^6$-fold or more greater, than its affinity for a non-target molecule, such as for a suitable control molecule (e.g., bovine serum albumin, casein).

Preferably, the specific binding agent may bind to its intended target(s) with affinity constant ($K_A$) of such binding $K_A \geq 1 \times 10^6$ M$^{-1}$, more preferably $K_A \geq 1 \times 10^7$ M$^{-1}$, yet more preferably $K_A \geq 1 \times 10^8$ M$^{-1}$, even more preferably $K_A \geq 1 \times 10^9$ M$^{-1}$, and still more preferably $K_A \geq 1 \times 10^{10}$ M$^{-1}$ or $K_A \geq 1 \times 10^{11}$ M$^{-1}$ or $K_A \geq 1 \times 10^{12}$ M$^{-1}$, wherein $K_A=[SBA\_T]/[SBA][T]$, SBA denotes the specific-binding agent, T denotes the intended target. Determination of $K_A$ can be carried out by methods known in the art, such as for example, using equilibrium dialysis and Scatchard plot analysis.

As used herein, the term "antibody" is used in its broadest sense and generally refers to any immunologic binding agent. The term specifically encompasses intact monoclonal antibodies, polyclonal antibodies, multivalent (e.g., 2-, 3- or more-valent) and/or multi-specific antibodies (e.g., bi- or more-specific antibodies) formed from at least two intact antibodies, and antibody fragments insofar they exhibit the desired biological activity (particularly, ability to specifically bind an antigen of interest, i.e., antigen-binding fragments), as well as multivalent and/or multi-specific composites of such fragments. The term "antibody" is not only inclusive of antibodies generated by methods comprising immunisation, but also includes any polypeptide, e.g., a recombinantly expressed polypeptide, which is made to encompass at least one complementarity-determining region (CDR) capable of specifically binding to an epitope on an antigen of interest. Hence, the term applies to such molecules regardless whether they are produced in vitro or in vivo.

An antibody may be any of IgA, IgD, IgE, IgG and IgM classes, and preferably IgG class antibody. An antibody may be a polyclonal antibody, e.g., an antiserum or immunoglobulins purified there from (e.g., affinity-purified). An antibody may be a monoclonal antibody or a mixture of monoclonal antibodies. Monoclonal antibodies can target a particular antigen or a particular epitope within an antigen with greater selectivity and reproducibility. By means of example and not limitation, monoclonal antibodies may be made by the hybridoma method first described by Kohler et al. 1975 (Nature 256: 495), or may be made by recombinant DNA methods (e.g., as in U.S. Pat. No. 4,816,567). Monoclonal antibodies may also be isolated from phage antibody libraries using techniques as described by Clackson et al. 1991 (Nature 352: 624-628) and Marks et al. 1991 (J Mol Biol 222: 581-597), for example.

Antibody binding agents may be antibody fragments. "Antibody fragments" comprise a portion of an intact antibody, comprising the antigen-binding or variable region thereof. Examples of antibody fragments include Fab, Fab', F(ab')2, Fv and scFv fragments, single domain (sd) Fv, such as VH domains, VL domains and VHH domains; diabodies; linear antibodies; single-chain antibody molecules, in particular heavy-chain antibodies; and multivalent and/or multispecific antibodies formed from antibody fragment(s), e.g., dibodies, tribodies, and multibodies. The above designations Fab, Fab', F(ab')2, Fv, scFv etc. are intended to have their art-established meaning.

The term antibody includes antibodies originating from or comprising one or more portions derived from any animal species, preferably vertebrate species, including, e.g., birds and mammals. Without limitation, the antibodies may be chicken, turkey, goose, duck, guinea fowl, quail or pheasant. Also without limitation, the antibodies may be human, murine (e.g., mouse, rat, etc.), donkey, rabbit, goat, sheep, guinea pig, camel (e.g., *Camelus bactrianus* and *Camelus dromaderius*), llama (e.g., *Lama paccos, Lama glama* or *Lama vicugna*) or horse.

A skilled person will understand that an antibody can include one or more amino acid deletions, additions and/or substitutions (e.g., conservative substitutions), insofar such alterations preserve its binding of the respective antigen. An antibody may also include one or more native or artificial modifications of its constituent amino acid residues (e.g., glycosylation, etc.).

Methods of producing polyclonal and monoclonal antibodies as well as fragments thereof are well known in the art, as are methods to produce recombinant antibodies or fragments thereof (see for example, Harlow and Lane, "Antibodies: A Laboratory Manual", Cold Spring Harbour Laboratory, New York, 1988; Harlow and Lane, "Using Antibodies: A Laboratory Manual", Cold Spring Harbour Laboratory, New York, 1999, ISBN 0879695447; "Monoclonal Antibodies: A Manual of Techniques", by Zola, ed., CRC Press 1987, ISBN 0849364760; "Monoclonal Antibodies: A Practical Approach", by Dean & Shepherd, eds., Oxford University Press 2000, ISBN 0199637229; Methods in Molecular Biology, vol. 248: "Antibody Engineering: Methods and Protocols", Lo, ed., Humana Press 2004, ISBN 1588290921).

In certain embodiments, the agent may be a Nanobody®. The terms "Nanobody®" and "Nanobodies®" are trademarks of Ablynx NV (Belgium). The term "Nanobody" is well-known in the art and as used herein in its broadest sense encompasses an immunological binding agent obtained (1) by isolating the $V_{HH}$ domain of a heavy-chain antibody, preferably a heavy-chain antibody derived from camelids; (2) by expression of a nucleotide sequence encoding a $V_{HH}$ domain; (3) by "humanization" of a naturally occurring $V_{HH}$ domain or by expression of a nucleic acid encoding a such humanized $V_{HH}$ domain; (4) by "camelization" of a $V_H$ domain from any animal species, and in particular from a mammalian species, such as from a human being, or by expression of a nucleic acid encoding such a camelized $V_H$ domain; (5) by "camelization" of a "domain antibody" or "dAb" as described in the art, or by expression of a nucleic acid encoding such a camelized dAb; (6) by using synthetic or semi-synthetic techniques for preparing proteins, polypeptides or other amino acid sequences known per se; (7) by preparing a nucleic acid encoding a Nanobody using techniques for nucleic acid synthesis known per se, followed by expression of the nucleic acid thus obtained; and/or (8) by any combination of one or more of the foregoing. "Camelids" as used herein comprise old world camelids (*Camelus bactrianus* and *Camelus dromaderius*) and new world camelids (for example *Lama paccos, Lama glama* and *Lama vicugna*).

Examples of antibodies capable of binding to human CD321 include without limitation those available from the following vendors ("#" stands for catalogue number): Merck Millipore (#04-593, rabbit monoclonal, clone EP1042Y); R&D Systems (#MAB1103, mouse monoclonal, clone 654806); OriGene Antibodies (#TA506034, mouse monoclonal, clone OTI6E11; #TA506017, mouse monoclonal, clone OTI3H3); Novus Biologicals (#H00050848-M01, mouse monoclonal, clone 2E3-1C8); Abcam (#ab17261, mouse monoclonal, clone M.Ab.F11; #ab201562, mouse monoclonal, clone MM0785-60M31); Invitrogen (#14-9321-82, mouse monoclonal, clone WK9; #MA1-34731, mouse monoclonal, clone M.Ab.F11); and Santa Cruz (#sc-135956, mouse monoclonal, clone 43; sc-53624, mouse monoclonal, clone 1H2A9; #sc-53623, mouse monoclonal, clone J10.4; #sc-53622, mouse monoclonal, clone J3F.1; #sc-52690, mouse monoclonal, clone M.Ab.F11). Information about the suitability of a given antibody for a given antigen detection technique or method is readily available from the vendor of the antibody.

Numerous antibodies binding to other markers, peptides, polypeptides and proteins described herein, such as antibodies to pan-leukocyte markers, such as CD45, LSP1, or CD48, or antibodies to thrombocyte markers, such as CD36, CD41, CD42a, CD42b, or CD61, are also commercially available from a variety of vendors. This information can be obtained from the respective vendors, and is also conveniently catalogued and can be queried in publically available databases, such as the GeneCards® database maintained by the Weizmann Institute (www.genecards.org), field "Antibody products".

The term "antibody-like protein scaffolds" or "engineered protein scaffolds" broadly encompasses proteinaceous non-immunoglobulin specific-binding agents, typically obtained by combinatorial engineering (such as site-directed random mutagenesis in combination with phage display or other molecular selection techniques). Usually, such scaffolds are derived from robust and small soluble monomeric proteins (such as Kunitz inhibitors or lipocalins) or from a stably folded extra-membrane domain of a cell surface receptor (such as protein A, fibronectin or the ankyrin repeat).

Such scaffolds have been extensively reviewed in Binz et al., Gebauer and Skerra, Gill and Damle, Skerra 2000, and Skerra 2007, and include without limitation affibodies, based on the Z-domain of staphylococcal protein A, a three-helix bundle of 58 residues providing an interface on two of its alpha-helices (Nygren); engineered Kunitz domains based on a small (ca. 58 residues) and robust, disulphide-cross-linked serine protease inhibitor, typically of human origin (e.g. LACI-D1), which can be engineered for different protease specificities (Nixon and Wood); monobodies or adnectins based on the 10th extracellular domain of human fibronectin III (10Fn3), which adopts an Ig-like beta-sandwich fold (94 residues) with 2-3 exposed loops, but lacks the central disulphide bridge (Koide and Koide); anticalins derived from the lipocalins, a diverse family of eight-stranded beta-barrel proteins (ca. 180 residues) that naturally form binding sites for small ligands by means of four structurally variable loops at the open end, which are abundant in humans, insects, and many other organisms (Skerra 2008); DARPins, designed ankyrin repeat domains (166 residues), which provide a rigid interface arising from typically three repeated beta-turns (Stumpp et al.); avimers (multimerized LDLR-A module) (Silverman et al.); and cysteine-rich knottin peptides (Kolmar).

The term "aptamer" refers to single-stranded or double-stranded oligo-DNA, oligo-RNA or oligo-DNA/RNA or any analogue thereof that specifically binds to a target molecule such as a peptide. Advantageously, aptamers display fairly high specificity and affinity (e.g., $K_A$ in the order $1\times10^9$ $M^{-1}$) for their targets. Aptamer production is described inter alia in U.S. Pat. No. 5,270,163; Ellington & Szostak 1990 (Nature 346: 818-822); Tuerk & Gold 1990 (Science 249: 505-510); or "The Aptamer Handbook: Functional Oligonucleotides and Their Applications", by Klussmann, ed., Wiley-VCH 2006, ISBN 3527310592, incorporated by reference herein. The term "photoaptamer" refers to an aptamer that contains one or more photoreactive functional groups that can covalently bind to or crosslink with a target molecule. The term "spiegelmer" refers to an aptamer which includes L-DNA, L-RNA, or other left-handed nucleotide derivatives or nucleotide-like molecules. Aptamers containing left-handed nucleotides are resistant to degradation by naturally occurring enzymes, which normally act on substrates containing right-handed nucleotides. The term "peptidomimetic" refers to a non-peptide agent that is a topological analogue of a corresponding peptide. Methods of rationally designing peptidomimetics of peptides are known in the art. For example, the rational design of three peptidomimetics based on the sulphated 8-mer peptide CCK26-33, and of two peptidomimetics based on the 11-mer peptide Substance P, and related peptidomimetic design principles, are described in Horwell 1995 (Trends Biotechnol 13: 132-134).

The term "oligonucleotide" as used throughout this specification refers to a nucleic acid (including nucleic acid analogues and mimetics) oligomer or polymer as defined herein. Preferably, an oligonucleotide, such as more particularly an antisense oligonucleotide, is (substantially) single-stranded. Oligonucleotides as intended herein may be preferably between about 10 and about 100 nucleoside units (i.e., nucleotides or nucleotide analogues) in length, preferably between about 15 and about 50, more preferably between about 20 and about 40, also preferably between about 20 and about 30. Oligonucleotides as intended herein may comprise one or more or all non-naturally occurring heterocyclic bases and/or one or more or all non-naturally occurring sugar groups and/or one or more or all non-naturally occurring inter-nucleoside linkages, the inclusion of which may improve properties such as, for example, increased stability in the presence of nucleases and increased hybridization affinity, increased tolerance for mismatches, etc.

Nucleic acid binding agents, such as oligonucleotide binding agents, are typically at least partly antisense to a target nucleic acid of interest. The term "antisense" generally refers to an agent (e.g., an oligonucleotide) configured to specifically anneal with (hybridize to) a given sequence in a target nucleic acid, such as for example in a target DNA, hnRNA, pre-mRNA or mRNA, and typically comprises, consist essentially of or consist of a nucleic acid sequence that is complementary or substantially complementary to said target nucleic acid sequence. Antisense agents suitable for use herein, such as hybridization probes or amplification or sequencing primers and primer pairs) may typically be capable of annealing with (hybridizing to) the respective target nucleic acid sequences at high stringency conditions, and capable of hybridizing specifically to the target under physiological conditions. The terms "complementary" or "complementarity" as used throughout this specification with reference to nucleic acids, refer to the normal binding of single-stranded nucleic acids under permissive salt (ionic strength) and temperature conditions by base pairing, preferably Watson-Crick base pairing. By means of example, complementary Watson-Crick base pairing occurs between the bases A and T, A and U or G and C. For example, the sequence 5'-A-G-U-3' is complementary to sequence 5'-A-C-U-3'.

The reference to oligonucleotides may in particular but without limitation include hybridization probes and/or amplification primers and/or sequencing primers, etc., as commonly used in nucleic acid detection technologies.

The term "small molecule" refers to compounds, preferably organic compounds, with a size comparable to those organic molecules generally used in pharmaceuticals. The term excludes biological macromolecules (e.g., proteins, peptides, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da.

Binding agents as discussed herein may suitably comprise a detectable label. The term "label" refers to any atom, molecule, moiety or biomolecule that may be used to provide a detectable and preferably quantifiable read-out or property, and that may be attached to or made part of an entity of interest, such as a binding agent. Labels may be suitably detectable by for example mass spectrometric, spectroscopic, optical, colorimetric, magnetic, photochemical, biochemical, immunochemical or chemical means. Labels include without limitation dyes; radiolabels such as $^{32}P$, $^{33}P$, $^{35}S$, $^{125}I$, $^{131}I$; electron-dense reagents; enzymes (e.g., horse-radish peroxidase or alkaline phosphatase as commonly used in immunoassays); binding moieties such as biotin-streptavidin; haptens such as digoxigenin; luminogenic, phosphorescent or fluorogenic moieties; mass tags; and fluorescent dyes alone or in combination with moieties that may suppress or shift emission spectra by fluorescence resonance energy transfer (FRET).

In some embodiments, binding agents may be provided with a tag that permits detection with another agent (e.g., with a probe binding partner). Such tags may be, for example, biotin, streptavidin, his-tag, myc tag, maltose, maltose binding protein or any other kind of tag known in the art that has a binding partner. Example of associations which may be utilised in the probe:binding partner arrangement may be any, and includes, for example biotin:streptavidin, his-tag:metal ion (e.g., $Ni^{2+}$), maltose:maltose binding protein, etc.

The marker-binding agent conjugate may be associated with or attached to a detection agent to facilitate detection. Examples of detection agents include, but are not limited to, luminescent labels; colorimetric labels, such as dyes; fluorescent labels; or chemical labels, such as electroactive agents (e.g., ferrocyanide); enzymes; radioactive labels; or radiofrequency labels. The detection agent may be a particle. Examples of such particles include, but are not limited to, colloidal gold particles; colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles, such as polystyrene latex beads. Preferable particles may be colloidal gold particles.

As already mentioned, certain aspects employ the uses and methods for detecting, quantifying or isolating tumor cells or CTCs as taught herein in applications relating to diagnosis, prognosis or monitoring of neoplastic diseases.

The terms "diagnosis" and "monitoring" are commonplace and well-understood in medical practice. By means of further explanation and without limitation the term "diagnosis" generally refers to the process or act of recognizing, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition).

The term "monitoring" generally refers to the follow-up of a disease or a condition in a subject for any changes which may occur over time.

The term "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such.

The terms also encompass prediction of a disease. The terms "predicting" or "prediction" generally refer to an advance declaration, indication or foretelling of a disease or condition in a subject not (yet) having said disease or condition. For example, a prediction of a disease or condition in a subject may indicate a probability, chance or risk that the subject will develop said disease or condition, for example within a certain time period or by a certain age. Said probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a 'negative' prediction of such, i.e., that the subject's risk of having such is not significantly increased vis-à-vis a control subject or subject population.

The present methods for the diagnosis, prediction, prognosis and/or monitoring of the proliferative disease may be adequately qualified as in vitro methods in that they apply one or more in vitro processing and/or analysis steps to a sample removed from the subject. The term "in vitro" generally denotes outside, or external to, a body, e.g., an animal or human body.

By means of an example, the presence of tumor cells or CTCs in a biological sample from a subject can provide an indication that the subject has a neoplastic disease, i.e., can provide or contribute to the diagnosis of the neoplastic disease in the subject; the presence of tumor cells or CTCs in a biological sample from a subject can provide an indication that a subject known to have a neoplastic disease in remission has relapsed; the presence of CTCs in a biological sample from a subject can provide an indication that the subject has a neoplastic disease having a metastatic potential (the term "metastatic potential" broadly refers to the ability of a tumor, such as a primary tumor, to give rise to metastases, and may also specifically encompass the potential for the recurrence of metastatic disease, the potential for a metastatic cancer to progress rapidly, and/or the potential for metastatic cancer to display resistance to a therapy, e.g., chemotherapy and/or immunotherapy); a comparatively higher quantity of CTCs in a biological sample from a subject can provide an indication that the subject has a neoplastic disease having a comparatively higher metastatic potential; a comparatively lower quantity of CTCs in a biological sample from a subject can provide an indication that the subject has a neoplastic disease having a comparatively lower metastatic potential; a comparatively higher quantity of tumor cells or CTCs in a biological sample from a subject can provide an indication that the subject has a comparatively poorer prognosis of a neoplastic disease; a comparatively lower quantity of tumor cells or CTCs in a biological sample from a subject can provide an indication that the subject has a comparatively better prognosis of a neoplastic disease; an increase in the quantity of tumor cells or CTCs in a biological sample from a subject obtained at second, later time point vs. a biological sample obtained from the same subject at a first, earlier time point can provide an indication that the neoplastic disease in the subject has progressed or worsened between said first and second time points; a decrease in the quantity of tumor cells or CTCs in a biological sample from a subject obtained at second, later time point vs. a biological sample obtained from the same subject at a first, earlier time point can provide an indication that the neoplastic disease in the subject has regressed between said first and second time points, for example spontaneously and/or in response to therapy.

In certain embodiments, the methods may rely on comparing the quantity of tumor cells or CTCs measured in samples from patients with reference values, wherein said reference values represent known predictions, diagnoses and/or prognoses of neoplastic diseases.

For example, distinct reference values may represent the prediction of a risk (e.g., an abnormally elevated risk) of having a neoplastic disease vs. the prediction of no or normal risk of having said neoplastic disease. In another example, distinct reference values may represent predictions of differing degrees of risk of having such neoplastic disease.

In a further example, distinct reference values can represent the diagnosis of a given neoplastic disease vs. the diagnosis of no such neoplastic disease (such as, e.g., the diagnosis of healthy, or recovered from said neoplastic disease, etc.). In another example, distinct reference values may represent the diagnosis of such neoplastic disease of varying severity.

In yet another example, distinct reference values may represent a good prognosis for a given neoplastic disease as taught herein vs. a poor prognosis for said neoplastic disease. In a further example, distinct reference values may represent varyingly favorable or unfavorable prognoses for such neoplastic disease.

Such comparison may generally include any means to determine the presence or absence of at least one difference or deviation and optionally of the size of such difference or deviation between values being compared. A comparison may include a visual inspection, an arithmetical or statistical comparison of measurements. Such statistical comparisons include, but are not limited to, applying a rule.

Reference values may be established according to known procedures previously employed for other cell populations and biomarkers. For example, a reference value may be established in an individual or a population of individuals characterized by a particular diagnosis, prediction and/or prognosis of said neoplastic disease (i.e., for whom said diagnosis, prediction and/or prognosis of the neoplastic disease holds true). Such population may comprise without limitation 2 or more, 10 or more, 100 or more, or even several hundred or more individuals.

A "deviation" of a first value from a second value may generally encompass any direction (e.g., increase: first value>second value; or decrease: first value<second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., ±1×SD or ±2×SD or ±3×SD, or ±1×SE or ±2×SE or ±3×SE). Deviation may also refer to a value falling outside of a reference range defined by values in a given population (for example, outside of a range which comprises ≥40%, ≥50%, ≥60%, ≥70%, ≥75% or ≥80% or ≥85% or ≥90% or ≥95% or even ≥100% of values in said population).

In a further embodiment, a deviation may be concluded if an observed alteration is beyond a given threshold or cut-off. Such threshold or cut-off may be selected as generally known in the art to provide for a chosen sensitivity and/or specificity of the prediction methods, e.g., sensitivity and/or specificity of at least 50%, or at least 60%, or at least 70%, or at least 80%, or at least 85%, or at least 90%, or at least 95%.

For example, receiver-operating characteristic (ROC) curve analysis can be used to select an optimal cut-off value of the quantity of tumor cells or CTCs or of a biomarker, for clinical use of the present diagnostic tests, based on acceptable sensitivity and specificity, or related performance measures which are well-known per se, such as positive predictive value (PPV), negative predictive value (NPV), positive likelihood ratio (LR+), negative likelihood ratio (LR−), Youden index, or similar.

By means of an example and without limitation, detection of at least 1 CTC in a 7.5 mL sample of peripheral blood can provide an indication that the subject has a neoplastic disease, more particularly a neoplastic disease having a metastatic potential. Detection of a comparatively higher quantity of CTCs in a subject (e.g., ≥0.5, ≥1, ≥2, or ≥3 CTCs per mL of peripheral blood) can provide an indication that the subject has a comparatively poorer prognosis of a neoplastic disease than a subject with a comparatively lower quantity of CTCs (e.g., <0.5, <1, <2, or <3 CTCs per mL of peripheral blood, respectively).

As used throughout this specification, the terms "therapy" or "treatment" refer to the alleviation or measurable lessening of one or more symptoms or measurable markers of a pathological condition such as a disease or disorder. The terms encompass primary treatments as well as neo-adjuvant treatments, adjuvant treatments and adjunctive therapies. The terms "anti-cancer therapy" or "anti-cancer treatment" broadly refer to the alleviation or measurable lessening of one or more symptoms or measurable markers of a neoplastic disease. Measurable lessening includes any statistically significant decline in a measurable marker or symptom. Generally, the terms encompass both curative treatments and treatments directed to reduce symptoms and/or slow progression of the disease. The terms encompass both the therapeutic treatment of an already developed pathological condition, as well as prophylactic or preventative measures, wherein the aim is to prevent or lessen the chances of incidence of a pathological condition. In certain embodiments, the terms may relate to therapeutic treatments. In certain other embodiments, the terms may relate to preventative treatments. Treatment of a chronic pathological condition during the period of remission may also be deemed to constitute a therapeutic treatment. The term may encompass ex vivo or in vivo treatments as appropriate in the context of the present invention.

Non-limiting examples of anti-cancer therapies include surgery, radiotherapy, chemotherapy, biological therapy, and combinations thereof.

The term "surgery" as used throughout this specification broadly denotes treatments comprising surgical removal of neoplastic tissue or cells from a subject. Cancer surgery may remove an entire tumor, debulk a tumor, or remove a tumor or a portion thereof causing pain or pressure. Cancer surgery includes inter alia conventional open surgery, laparoscopic surgery, cryosurgery, laser surgery, thermal ablation such as hyperthermic laser ablation or radiofrequency ablation, photodynamic therapy, and combinations thereof.

The term "radiotherapy" as used throughout this specification broadly denotes treatments comprising the exposure of neoplastic tissue to ionizing radiation, such as radiation from x-rays, gamma rays, neutrons, protons, or other sources. The source of the radiation may be an external apparatus (external-beam radiation therapy), or the radioactive material may be placed in the body near the neoplastic tissue (internal radiation therapy or brachytherapy), or radioactive material may be delivered systemically by injection, infusion or ingestion (systemic radioisotope therapy) and may concentrate in the neoplastic tissue spontaneously or by means of a targeting moiety, such as a cancer-targeting antibody.

The term "chemotherapy" as used herein is conceived broadly and generally encompasses treatments using chemical substances or compositions. Chemotherapeutic agents may typically display cytotoxic or cytostatic effects.

In certain embodiments, a chemotherapeutic agent may be an alkylating agent, a cytotoxic compound, an anti-metabolite, a plant alkaloid, a terpenoid, a topoisomerase inhibitor, or a combination thereof.

The term "alkylating agent" generally refers to an agent capable of alkylating nucleophilic functional groups under physiological conditions. Examples of alkylating agents include but are not limited to cyclophosphamide, carmustine, cisplatin, carboplatin, oxaliplatin, mechlorethamine, melphalan (hydrochloride), chlorambucil, ifosfamide, lomustine, mitomycin C, ThioTEPA, busulfan, and combinations thereof.

The term "cytotoxic compound" generally refers to an agent toxic to a cell. Examples of cytotoxic compounds include but are not limited to actinomycin (also known as dactinomycin); anthracyclines such as doxorubicin, daunorubicin, valrubicin, idarubicin, and epirubicin; bleomycin; plicamycin; mitoxantrone; mitomycin; and combinations thereof.

The term "anti-metabolite" generally refers to an agent capable to inhibit the use of a metabolite such as purines or pyrimidines. Anti-metabolites prevent purines and pyrimidines from becoming incorporated into DNA during the S phase of the cell cycle and thereby stop normal development and division. Examples of anti-metabolites include but are not limited to azathioprine, capecitabine, cytarabine, 5-fluorouracil, mercaptopurine, methotrexate, nelarabine, pemetrexed, and combinations thereof.

Plant alkaloids and terpenoids are derived from plants and block cell division by preventing microtubule function. Non-limiting examples include vinca alkaloids and taxanes, and combinations thereof. Examples of vinca alkaloids include but are not limited to vincristine, vinblastine, vinorelbine, vindesine, and combinations thereof. Examples of taxanes include but are not limited to paclitaxel, docetaxel, and combinations thereof.

The term "topoisomerase inhibitor" generally refers to enzymes that maintain the topology of DNA. Non-limiting examples include type I and type II topoisomerase inhibitors. Examples of type I topoisomerase inhibitors include but are not limited to camptothecins such as irinotecan, topotecan, and combinations thereof. Examples of type II topoisomerase inhibitors include but are not limited to amsacrine, doxorubicin, daunorubicin, etoposide, etoposide phosphate, mitoxantrone, teniposide, and combinations thereof.

In certain embodiments, a chemotherapeutic agent may be selected from the group consisting of cyclophosphamide, doxorubicin, idarubicin, mitoxantrone, oxaliplatin, bortezomib, digoxin, digitoxin, hypericin, shikonin, wogonin, sorafenib, everolimus, imatinib, geldanamycin, panobinostat, carmustine, cisplatin, carboplatin, mechlorethamine, melphalan (hydrochloride), chlorambucil, ifosfamide, busulfan, actinomycin, daunorubicin, valrubicin, epirubicin, bleomycin, plicamycin, mitoxantrone, mitomycin, azathioprine, mercaptopurine, fluorouracil, methotrexate, nelarabine, pemetrexed, vincristine, vinblastine, vinorelbine, vindesine, paclitaxel, docetaxel, irinotecan, topotecan, amsacrine, etoposide, etoposide phosphate, teniposide, anastrozole, exemestane, bosutinib, irinotecan, vandetanib, bicalutamide, lomustine, clofarabine, cabozantinib, cytarabine, cytoxan, decitabine, dexamethasone, hydroxyurea, decarbazine, leuprolide, epirubicin, asparaginase, estramustine, vismodegib, amifostine, flutamide, toremifene, fulvestrant, letrozole, degarelix, fludarabine, pralatrexate, floxuridine, gemcitabine, carmustine wafer, eribulin, altretamine, topotecan, axitinib, gefitinib, romidepsin, ixabepilone, ruxolitinib, cabazitaxel, carfilzomib, chlorambucil, sargramostim, cladribine, leuprolide, mitotane, procarbazine, megestrol, mesna, strontium-89 chloride, mitomycin, filgrastim, pegfilgrastim, sorafenib, nilutamide, pentostatin, tamoxifen, pegaspargase, denileukin diftitox, alitretinoin, carboplatin, prednisone, mercaptopurine, zoledronic acid, lenalidomide, octreotide, dasatinib, regorafenib, histrelin, sunitinib, omacetaxine, thioguanine, erlotinib, bexarotene, decarbazine, temozolomide, thiotepa, thalidomide, BCG, temsirolimus, bendamustine hydrochloride, triptorelin, arsenic trioxide, lapatinib, valrubicin intravesical, tretinoin, azacitidine, pazopanib, teniposide, leucovorin, crizotinib, capecitabine, enzalutamide, ziv-aflibercept, streptozocin, vemurafenib, goserelin, vorinostat, zoledronic acid, abiraterone, and combinations thereof.

The term "biological therapy" as used herein is conceived broadly and generally encompasses treatments using biological substances or compositions, such as biomolecules, or biological agents, such as viruses or cells. In certain embodiments, the biological substances or compositions may exert the pharmacological actions or effects underlying the therapeutic benefit. In certain other embodiments, the biological substances or compositions may be used to deliver or target chemotherapeutic agents or radioisotopes to the neoplastic tissues or cells, for example the biological substances or compositions may be conjugated with the chemotherapeutic agents or radioisotopes (by means of an example and without limitation, a conjugate of a cancer-targeting monoclonal antibody and a cytotoxic chemical compound).

In certain embodiments, a biomolecule may be a peptide, polypeptide, protein, nucleic acid, or a small molecule (such as primary metabolite, secondary metabolite, or natural product), or a combination thereof. Examples of suitable biomolecules include without limitation interleukins, cytokines, anti-cytokines, tumor necrosis factor (TNF), cytokine receptors, vaccines, interferons, enzymes, therapeutic antibodies, antibody fragments, antibody-like protein scaffolds, or combinations thereof.

Examples of suitable biomolecules include but are not limited to aldesleukine, alemtuzumab, atezolizumab, bevacizumab, blinatumomab, brentuximab vedotine, catumaxomab, cetuximab, daratumumab, denileukin diftitox, denosumab, dinutuximab, elotuzumab, gemtuzumab ozogamicin, $^{90}$Y-ibritumomab tiuxetan, idarucizumab, interferon A, ipilimumab, necitumumab, nivolumab, obinutuzumab, ofatumumab, olaratumab, panitumumab, pembrolizumab, ramucirumab, rituximab, tasonermin, $^{131}$I-tositumomab, trastuzumab, Ado-trastuzumab emtansine, and combinations thereof.

Examples of suitable oncolytic viruses include but are not limited to talimogene laherparepvec.

Further categories of anti-cancer therapy include inter alia hormone therapy (endocrine therapy), immunotherapy, and stem cell therapy, which are commonly considered as subsumed within biological therapies.

Hormone therapy or endocrine therapy encompasses treatments in which hormones or anti-hormone drugs are administered for the treatment of hormone-dependent or hormone-sensitive cancers, such as inter alia hormone-dependent or hormone-sensitive breast cancer, prostate cancer, ovarian cancer, testicular cancer, endometrial cancer, or kidney cancer.

Examples of suitable hormone therapies include but are not limited to tamoxifen; aromatase inhibitors, such as atanastrozole, exemestane, letrozole, and combinations thereof; luteinizing hormone blockers such as goserelin, leuprorelin, triptorelin, and combinations thereof; anti-androgens, such as bicalutamide, cyproterone acetate, flutamide, and combinations thereof; gonadotrophin releasing hormone blockers, such as degarelix; progesterone treatments, such as medroxyprogesterone acetate, megestrol, and combinations thereof; and combinations thereof.

The term "immunotherapy" broadly encompasses any treatment that modulates a subject's immune system. In particular, the term comprises any treatment that modulates an immune response, such as a humoral immune response, a cell-mediated immune response, or both. An immune response may typically involve a response by a cell of the immune system, such as a B cell, cytotoxic T cell (CTL), T helper (Th) cell, regulatory T (Treg) cell, antigen-presenting cell (APC), dendritic cell, monocyte, macrophage, natural killer T (NKT) cell, natural killer (NK) cell, basophil, eosinophil, or neutrophil, to a stimulus. In the context of anti-cancer treatments, immunotherapy may preferably elicit, induce or enhance an immune response, such as in particular an immune response specifically against tumor tissues or cells, such as to achieve tumor cell death Immunotherapy may modulate, such increase or enhance, the abundance, function, and/or activity of any component of the immune system, such as any immune cell, such as without limitation T cells (e.g., CTLs or Th cells), dendritic cells, and/or NK cells.

Immunotherapy comprises cell-based immunotherapy in which immune cells, such as T cells and/or dendritic cells, are transferred into the patient. The term also comprises an administration of substances or compositions, such as chemical compounds and/or biomolecules (e.g., antibodies, antigens, interleukins, cytokines, or combinations thereof), that modulate a subject's immune system.

Examples of cancer immunotherapy include without limitation treatments employing monoclonal antibodies, for example Fc-engineered monoclonal antibodies against proteins expressed by tumor cells, immune checkpoint inhibitors, prophylactic or therapeutic cancer vaccines, adoptive cell therapy, and combinations thereof.

By means of further guidance, Fc-optimized monoclonal antibodies are configured to specifically bind a protein expressed by tumor cells, such as a tumor antigen, and comprise an engineered Fc portion mediating effector functions, such as antibody-dependent cellular cytotoxicity, complement-dependent cytotoxicity, and/or antibody-dependent cell-mediated phagocytosis.

The term "tumor antigen" as used throughout this specification refers to an antigen that is uniquely or differentially expressed by a tumor cell, whether intracellular or on the tumor cell surface (preferably on the tumor cell surface), compared to a normal or non-neoplastic cell. By means of example, a tumor antigen may be present in or on a tumor cell and not typically in or on normal cells or non-neoplastic cells (e.g., only expressed by a restricted number of normal tissues, such as testis and/or placenta), or a tumor antigen may be present in or on a tumor cell in greater amounts than in or on normal or non-neoplastic cells, or a tumor antigen may be present in or on tumor cells in a different form than that found in or on normal or non-neoplastic cells. The term thus includes tumor-specific antigens (TSA), including tumor-specific membrane antigens, tumor-associated antigens (TAA), including tumor-associated membrane antigens, embryonic antigens on tumors, growth factor receptors, growth factor ligands, etc. The term further includes cancer/testis (CT) antigens. Examples of tumor antigens include, without limitation, β-human chorionic gonadotropin (βHCG), glycoprotein 100 (gp100/Pme117), carcinoembryonic antigen (CEA), tyrosinase, tyrosinase-related protein 1 (gp75/TRP1), tyrosinase-related protein 2 (TRP-2), NY-BR-1, NY-CO-58, NY-ESO-1, MN/gp250, idiotypes, telomerase, synovial sarcoma X breakpoint 2 (SSX2), mucin 1 (MUC-1), antigens of the melanoma-associated antigen (MAGE) family, high molecular weight-melanoma associated antigen (HMW-MAA), melanoma antigen recognized by T cells 1 (MART1), Wilms' tumor gene 1 (WT1), HER2/neu, mesothelin (MSLN), alphafetoprotein (AFP), cancer antigen 125 (CA-125), and abnormal forms of ras or p53. Further targets in neoplastic diseases include without limitation CD37 (chronic lymphocytic leukemia), CD123 (acute myeloid leukemia), CD30 (Hodgkin/large cell lymphoma), MET (NSCLC, gastroesophageal cancer), IL-6 (NSCLC), and GITR (malignant melanoma).

Immune checkpoints are inhibitory pathways that slow down or stop immune reactions and prevent excessive tissue damage from uncontrolled activity of immune cells. Inhibition of immune checkpoint targets can stimulate immune responses by immune cells, such as CTLs, against tumor cells.

Examples of immune checkpoint targets for inhibition include without limitation PD-1 (examples of PD-1 inhibitors include without limitation pembrolizumab, nivolumab, and combinations thereof), CTLA-4 (examples of CTLA-4 inhibitors include without limitation ipilimumab, tremelimumab, and combinations thereof), PD-L1 (examples of PD-L1 inhibitors include without limitation atezolizumab), LAG3, B7-H3 (CD276), B7-H4, TIM-3, BTLA, A2aR, killer cell immunoglobulin-like receptors (KIRs), IDO, and combinations thereof.

The term "vaccine" generally refers to a therapeutic or prophylactic pharmaceutical composition for in vivo administration to a subject, comprising a component to which a vaccinated subject is induced to raise an immune response, preferably a protective immune response, or immune tolerance (tolerising vaccines).

Optionally, the vaccine may further comprise one or more adjuvants for enhancing the immune response. Suitable adjuvants include, for example, but without limitation, saponin, mineral gels such as aluminium hydroxide, surface active substances such as lysolecithin, pluronic polyols, polyanions, peptides, oil or hydrocarbon emulsions, bacilli Calmette-Guerin (BCG), keyhole limpet hemocyanin (KLH), monophosphoryl lipid A (MPL), *Corynebacterium parvum*, oligodeoxynucleotides containing unmethylated CpG motif, and QS-21.

Optionally, the vaccine may further comprise one or more immunostimulatory molecules, or one or more molecules promoting immune tolerance. Non-limiting examples of such molecules include various cytokines, lymphokines and chemokines. By means of example, non-limiting examples of molecules with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc.

Tumor vaccines include vaccines that either a) prevent infections with cancer-causing viruses, b) treat existing cancer (therapeutic cancer vaccines) or c) prevent the development of cancer, or ameliorate its effects (prophylactic cancer vaccines).

One approach to produce tumor vaccines of type b) or c), also known as therapeutic or immunotherapeutic tumor vaccines, is to isolate tumor cells from a cancer patient, prepare an immunogenic composition from said tumor cells, for example, by rendering said tumor cells non-viable, preparing a lysate of said tumor cells, or isolating proteins from said tumor cells, and immunize a subject (e.g., the same cancer patient or another subject) with a vaccine comprising said immunogenic composition. The immunogenic composition contains tumor antigen(s) expressed by said tumor cells, whereby the vaccination can elicit or stimulate an immune response (e.g., B-cell or CTL response) against the tumor antigen(s) and the tumor cells expressing the tumor antigen(s).

Another approach to therapeutic anti-cancer vaccination is to generate the immune response in situ in a patient. This enhances the anti-tumor immune response to tumor antigens released following lytic virus replication providing an in situ, patient specific anti-tumor vaccine as a result (examples of suitable oncolytic viruses include but are not limited to talimogene laherparepvec). Yet another approach is to immunize a patient with a compound that play a physiological role in cancer genesis, so that the human body eliminates said compound. In such case, the compound is a self-antigen or a self-hapten, i.e., it does not provoke a strong immune response when administered to the patient, but can elicit an adequate immune response when conjugated to a carrier.

Another approach to therapeutic anti-cancer vaccination includes dendritic cell vaccines. The term broadly encompasses vaccines comprising dendritic cells which are loaded with antigen(s) against which an immune reaction is desired.

The term "dendritic cell" (DC) may refer to any member of a diverse population of morphologically similar cell types found in lymphoid or non-lymphoid tissues. DC may include, for example, "professional" antigen presenting cells, and have a high capacity for sensitising MHC-restricted T cells. DCs may be recognised, for example, by function, by phenotype and/or by gene expression pattern, particularly by cell surface phenotype. These cells can be characterised by their distinctive morphology, high levels of surface MHC-class II expression and ability to present antigen to CD4+ and/or CD8+ T cells, particularly to naive T cells. Functionally, DCs may be identified by any suitable assay, known to one of skilled in the art, for determination of antigen presentation. Such assays may include, for example, testing the ability to stimulate antigen-primed and/or naive T cells by presentation of a test antigen, followed by determination of T cell proliferation, release of cytokines such as IL-2, and the like. Dendritic cells can be isolated or generated from a biological sample by methods well known in the art. Suitable biological samples for isolation or generation of DC include without limitation a peripheral blood sample, bone marrow sample, umbilical cord blood sample or the like. By means of an example but without limitation, DC present in a biological sample may be isolated by immunofluorescent or immunomagnetic labelling of select surface markers known to be expressed or not expressed by DC, coupled with a corresponding fluorescence activated cell sorting (FACS) gating strategy or immunomagnetic separation, respectively. Alternatively, DC can be generated from CD14+ monocytes by incubating them with suitable cytokines (Zhou & Tedder, Proc Natl Acad Sci USA. 1996, vol. 93, 2588-92).

The term "antigen loading" as used throughout this specification refers to a method or process of delivering one or more antigens to immune cells, such as particularly to antigen-presenting cells, such as more particularly to dendritic cells, such that the antigenic epitopes of the antigen(s) are presented on MHC, whether intracellular or on the immune cell surface. Typically, immune cells may be loaded with antigen(s) by a process comprising contacting or incubating the immune cells in vitro/ex vivo with a composition comprising the antigen(s) or a composition comprising nucleic acid(s) encoding the antigen(s) under conditions that permit the immune cells to contact, express (if needed), process and present the antigen(s) on MHC. The skilled person will know the incubation temperature and time periods sufficient to allow for effective loading of antigens. For example, incubation steps may be typically from between about 1 to about 2 or about 4 hours, at temperatures of between about 25° C. to about 37° C. and/or may be overnight at about 4° C., and the like. By means of an example, the immune cells may be contacted with a composition comprising an isolated antigen, for example, an antigen isolated from a naturally-occurring source of the antigen, or an antigen produced recombinantly by a suitable host or host cell expression system and isolated therefrom (e.g., a suitable bacterial, yeast, fungal, plant or animal host or host cell expression system), or produced recombinantly by cell-free transcription or translation, or non-biological nucleic acid or peptide synthesis. By means of another example, the immune cells may be contacted with a composition comprising a naturally-occurring source of the antigen, i.e., substantially without isolating the antigen from said naturally-occurring source. For instance, the immune cells may be contacted with a composition comprising cells which naturally express the antigen or cell debris of such cells, e.g., tumor cells expressing tumor antigen(s). Suitably, such cells may be rendered non-viable and preferably lysed, for example, killed and preferably lysed by a mechanical, chemical or physical treatment, such as heat killed, apoptotic, necrotic or otherwise processed. By means of a further example, the immune cells may be contacted with cells of a suitable host or host cell expression system which recombinantly produce the antigen, i.e., substantially without isolating the antigen from said cells. Suitably, such cells may be rendered non-viable and preferably lysed, for example, killed and preferably lysed by a mechanical, chemical or physical treatment, such as heat killed or otherwise processed Immune cells may also be loaded with an antigen by introducing into the immune cells a nucleic acid, commonly a recombinant nucleic acid, encoding the antigen, whereby the immune cells express the antigen.

Adoptive cell therapy (ACT) can refer to the transfer of cells, most commonly immune-derived cells, such as in particular cytotoxic T cells (CTLs), back into the same patient or into a new recipient host with the goal of transferring the immunologic functionality and characteristics into the new host. If possible, use of autologous cells helps the recipient by minimizing tissue rejection and graft vs. host disease issues.

The adoptive transfer of autologous tumor infiltrating lymphocytes (TILs) or genetically re-directed peripheral blood mononuclear cells has been used to successfully treat patients with advanced solid tumors, including melanoma and colorectal carcinoma, as well as patients with CD19-expressing hematologic malignancies. Adoptive transfer of immune system cells, such as T cells, specific for selected antigens, such as tumor associated antigens is particularly envisaged.

Various strategies may for example be employed to genetically modify T cells by altering the specificity of the T cell receptor (TCR) for example by introducing new TCR α and β chains with selected peptide specificity. Alternatively, chimeric antigen receptors (CARs) may be used in order to generate immunoresponsive cells, such as T cells, specific for selected targets, such as malignant cells, with a wide variety of receptor chimera constructs having been described.

Examples of CAR constructs include without limitation 1) CARs consisting of a single-chain variable fragment of an antibody specific for an antigen, for example comprising a $V_L$ linked to a $V_H$ of a specific antibody, linked by a flexible linker, for example by a CD8α hinge domain and a CD8α transmembrane domain, to the transmembrane and intracellular signaling domains of either CD3ζ or FcRγ; and 2) CARs further incorporating the intracellular domains of one or more costimulatory molecules, such as CD28, OX40 (CD134), or 4-1BB (CD137) within the endodomain, or even including combinations of such costimulatory endodomains.

Stem cell therapies in cancer commonly aim to replace bone marrow stem cells destroyed by radiation therapy and/or chemotherapy, and include without limitation autologous, syngeneic, or allogeneic stem cell transplantation. The stem cells, in particular hematopoietic stem cells, are typically obtained from bone marrow, peripheral blood or umbilical cord blood.

Details of administration routes, doses, and treatment regimens of anti-cancer agents are known in the art, for example as described in "Cancer Clinical Pharmacology" (2005) ed. By Jan H. M. Schellens, Howard L. McLeod and David R. Newell, Oxford University Press.

The tumor cells or CTCs isolated by the methods as taught herein can be used in a variety of applications.

By means of an example but not limitation, such tumor cells or CTCs, advantageously rendered non-viable, or lysates thereof, or one or more tumor antigens thereof (e.g., as isolated proteins or comprised in a protein composition isolated from the tumor cells or CTCs) can be formulated into tumor vaccines, as taught elsewhere in this specification. Optionally, such tumor vaccines can further comprise dendritic cells, as explained elsewhere in this specification.

By means of another example but not limitation, such tumor cells or CTCs may be subjected to further analysis to reveal or characterize properties of the cells. For example, the cells may be subjected to biochemical analysis, mutation analysis, transcriptomic analysis and/or proteomic analysis. Such analysis can reveal biochemical properties, genomic and/or mitochondrial mutations, gene expression profiles and signatures and protein expression profiles and signatures of the cells, which may for example be causative or associated with the neoplastic disease and/or with the circulating phenotype of the cells.

A further aspect of the invention relates to a method for in situ imaging of tumor in a subject comprising administering to the subject an agent capable of specifically binding to CD321, said agent comprising a label detectable by an imaging modality, allowing said agent to specifically bind to CD321 expressed by the cells of the tumor, and visualizing the tumor in the subject using said imaging modality.

The term "imaging" broadly encompasses any medical imaging technique or process for creating visual representations of the interior of a body and/or visual representation of the function of organs or tissues. Imaging modalities or technologies as envisaged herein may include but are not limited to X-ray radiography, X-ray computed tomography (CT), magnetic resonance imaging (MRI), positron emission tomography (PET), PET-CT, and single-photon emission computed tomography (SPECT). Preferably, the imaging modality may be PET-based, such as PET, PET-CT, or SPECT, more preferably PET.

In the present imaging methods, a CD321 specific-binding agent is labeled such as to be detectable, i.e., to allow detection and visualization by the appropriate imaging modality. By means of example but not limitation, labels suitable for PET-based imaging techniques include radionuclides such as $^{11}C$, $^{13}N$, $^{15}O$, $^{18}F$, $^{68}Ga$, $^{89}Zr$, or $^{82}Rb$.

Further aspects relate to kits of parts or articles of manufacture useful for practicing the uses and methods as described throughout this specification.

Hence, an aspect relates to a kit of parts or an article of manufacture comprising one or more agents capable of specifically binding to CD321, and one or more agents capable of specifically binding to at least one pan-leukocyte marker.

Another aspect relates to a kit of parts or an article of manufacture comprising one or more agents capable of specifically binding to CD321, and one or more agents capable of specifically binding to at least one thrombocyte marker.

A yet further aspect relates to a kit of parts or an article of manufacture comprising one or more agents capable of specifically binding to CD321, one or more agents capable of specifically binding to at least one pan-leukocyte marker, and one or more agents capable of specifically binding to at least one thrombocyte marker.

The terms "kit of parts" and "kit" as used throughout this specification refer to a product containing components necessary for carrying out the specified methods, packed so as to allow their transport and storage. Materials suitable for packing the components comprised in a kit include crystal, plastic (e.g., polyethylene, polypropylene, polycarbonate), bottles, flasks, vials, ampules, paper, envelopes, or other types of containers, carriers or supports. Where a kit comprises a plurality of components, at least a subset of the components (e.g., two or more of the plurality of components) or all of the components may be physically separated, e.g., comprised in or on separate containers, carriers or supports. The components comprised in a kit may be sufficient or may not be sufficient for carrying out the specified methods, such that external reagents or substances may not be necessary or may be necessary for performing the methods, respectively. Typically, kits are employed in conjunction with standard laboratory equipment, such as liquid handling equipment, environment (e.g., temperature) controlling equipment, analytical instruments, etc. In addition to the recited binding agents(s) as taught herein, such as for example, antibodies, hybridization probes, amplification and/or sequencing primers, optionally provided on arrays or microarrays, the present kits may also include some or all of solvents, buffers (such as for example but without limitation histidine-buffers, citrate-buffers, succinate-buffers, acetate-buffers, phosphate-buffers, formate buffers, benzoate buffers, TRIS (Tris(hydroxymethyl)-aminomethan) buffers or maleate buffers, or mixtures thereof), enzymes (such as for example but without limitation thermostable DNA polymerase), detectable labels, detection reagents, and control formulations (positive and/or negative), useful in the specified methods. Typically, the kits may also include instructions for use thereof, such as on a printed insert or on a computer readable medium. The terms may be used interchangeably with the term "article of manufacture", which broadly encompasses any man-made tangible structural product, when used in the present context.

In certain embodiments of the kits of parts or articles of manufacture as taught herein, the pan-leukocyte marker is selected from the group consisting of CD45, LSP1, CD48, and combinations thereof.

In certain embodiments of the kits of parts or articles of manufacture as taught herein, the thrombocyte marker is selected from the group consisting of CD36, CD41, CD42a, CD42b, CD61, and combinations thereof.

In certain embodiments of the kits of parts or articles of manufacture as taught herein, the pan-leukocyte marker is selected from the group consisting of CD45, LSP1, CD48, and combinations thereof, and the thrombocyte marker is selected from the group consisting of CD36, CD41, CD42a, CD42b, CD61, and combinations thereof;

In certain preferred embodiments of the kits of parts or articles of manufacture as taught herein, the pan-leukocyte marker is CD45.

In certain preferred embodiments of the kits of parts or articles of manufacture as taught herein, the thrombocyte marker is CD42a.

In certain preferred embodiments of the kits of parts or articles of manufacture as taught herein, the pan-leukocyte marker is CD45 and the thrombocyte marker is CD42a.

Agents capable of specifically binding to markers, such as peptides, polypeptides, proteins, or nucleic acids, such as to CD321, CD45, LSP1, CD48, CD36, CD41, CD42a, CD42b, or CD61, have been described elsewhere in this specification.

In certain embodiments of the kits of parts or articles of manufacture as taught herein, the one or more agents are configured for use in a technique selected from the group consisting of flow cytometry, mass cytometry, fluorescence activated cell sorting, fluorescence microscopy, affinity separation, magnetic cell separation, microfluidic separation, and combinations thereof, as explained elsewhere in this specification.

In certain embodiments of the kits of parts or articles of manufacture as taught herein, the one or more agents are, each independently, one or more antibodies, antibody fragments, antibody-like protein scaffolds, or aptamers, as explained elsewhere in this specification.

Examples of a kit as disclosed herein are without limitation as follows:
 a kit comprising a container comprising a mixture of A), B1) and C1);
 a kit comprising a container comprising a mixture of A), B2) and C2);
 a kit comprising a container comprising a mixture of A), B3) and C3);

a kit comprising a container comprising a mixture of A) and B1);

a kit comprising a container comprising a mixture of A) and B2);

a kit comprising a container comprising a mixture of A) and C3);

a kit comprising a container comprising a mixture of A) and C1);

a kit comprising a container comprising a mixture of A) and C2);

a kit comprising a container comprising a mixture of A) and C3);

a kit comprising a container comprising A), and a separate container comprising a mixture of B1) and C1);

a kit comprising a container comprising A), and a separate container comprising a mixture of B2) and C2);

a kit comprising a container comprising A), and a separate container comprising a mixture of B3) and C3);

a kit comprising a container comprising A), a separate container comprising B1), and a separate container comprising C1);

a kit comprising a container comprising A), a separate container comprising B2), and a separate container comprising C2); or a kit comprising a container comprising A), a separate container comprising B3), and a separate container comprising C3);

wherein "A)" stands for an anti-human CD321 antibody; "B1)" strands for an anti-human pan leukocyte marker antibody; "C1)" stands for an anti-human thrombocyte marker antibody; "B2)" stands for an antibody selected from the group consisting of anti-human CD45 antibody, anti-human LSP1 antibody, and anti-human CD48 antibody; "C2)" stands for an antibody selected from the group consisting of anti-human CD36 antibody, anti-human CD41 antibody, anti-human CD42a antibody, anti-human CD42b antibody, and anti-human CD61 antibody; "B3)" stands for an anti-human CD45 antibody; "C3)" stands for an anti-human CD42a antibody.

The present application thus provides particularly preferred aspects and embodiments as set forth in the following Statements 1-28:

Statement 1. A method for detecting or quantifying circulating tumor cells (CTCs) in a biological sample from a subject, and optionally for isolating said CTCs from the biological sample, comprising detecting the expression of CD321 by circulating non-hematopoietic cells in the biological sample, wherein the expression of CD321 by a circulating non-hematopoietic cell identifies said cell as a circulating tumor cell, and optionally isolating the CD321 expressing CTCs from the biological sample.

Statement 2. The method according to Statement 1, wherein the biological sample comprises circulating cells from blood, urine, feces, lymph or another exudate or secretory fluid of the subject, preferably from peripheral blood of the subject.

Statement 3. The method according to Statement 1 or 2, wherein a circulating CD321 positive tumor cell is identified as non-hematopoietic by the absence of expression of at least one pan-leukocyte marker and of at least one thrombocyte marker by said cell.

Statement 4. The method according to any one of Statements 1 to 3 comprising:
a) providing a biological sample from the subject, said biological sample comprising circulating cells from the subject, preferably circulating cells from blood, urine, feces, lymph or another exudate or secretory fluid of the subject, more preferably from peripheral blood of the subject;
b) detecting in said biological sample non-hematopoietic cells negative for at least one pan-leukocyte marker and negative for at least one thrombocyte marker;
c) detecting the expression of CD321 by the cells as detected in b), wherein the expression of CD321 by a cell as detected in b) identifies said cell as a circulating tumor cell.

Statement 5. The method according to Statement 3 or 4, wherein:
a) said pan-leukocyte marker is selected from the group consisting of CD45, LSP1, CD48, and combinations thereof;
b) said thrombocyte marker is selected from the group consisting of CD36, CD41, CD42a, CD42b, CD61, and combinations thereof;
c) said pan-leukocyte marker is selected from the group consisting of CD45, LSP1, CD48, and combinations thereof, and said thrombocyte marker is selected from the group consisting of CD36, CD41, CD42a, CD42b, CD61, and combinations thereof;
d) said pan-leukocyte marker is CD45;
e) said thrombocyte marker is CD42a; or
f) said pan-leukocyte marker is CD45 and said thrombocyte marker is CD42a.

Statement 6. The method according to any one of Statements 1 to 5, wherein the tumor is a solid tumor.

Statement 7. The method according to any one of Statements 1 to 6, wherein the tumor is of epithelial, mesenchymal or melanocyte origin.

Statement 8. The method according to any one of Statements 1 to 7, wherein the subject is human.

Statement 9. The method according to any one of Statements 1 to 8, wherein detecting the expression of CD321 comprises detecting CD321 protein or CD321 mRNA or both.

Statement 10. The method according to any one of Statements 1 to 9, wherein the CTCs are detected, quantified or isolated using a technique selected from the group consisting of flow cytometry, mass cytometry, fluorescence activated cell sorting, fluorescence microscopy, affinity separation, magnetic cell separation, microfluidic separation, and combinations thereof.

Statement 11. The method according to Statements 10, wherein the technique employs one or more agents capable of specifically binding to CD321.

Statement 12. The method according to Statement 10 or 11, wherein the technique further employs one or more agents capable of specifically binding to the at least one pan-leukocyte marker and one or more agents capable of specifically binding to the at least one thrombocyte marker.

Statement 13. The method according to Statement 11 or 12, wherein the one or more agents are, each independently, one or more antibodies, antibody fragments, antibody-like protein scaffolds, or aptamers.

Statement 14. The method according to any one of Statements 1 to 9, wherein the CTCs are detected, quantified or isolated using a technique which employs one or more agents capable of specifically binding to CD321.

Statement 15. The method according to Statement 14, wherein the technique further employs one or more agents capable of specifically binding to the at least one pan-leukocyte marker and one or more agents capable of specifically binding to the at least one thrombocyte marker.

Statement 16. The method according to Statement 14 or 15, wherein the one or more agents are, each independently, one or more antibodies, antibody fragments, antibody-like protein scaffolds, or aptamers.

Statement 17. The method according to any one of Statements 14 to 16, wherein the CTCs are detected, quantified or isolated using a technique selected from the group consisting of flow cytometry, mass cytometry, fluorescence activated cell sorting, fluorescence microscopy, affinity separation, magnetic cell separation, microfluidic separation, and combinations thereof.

Statement 18. The method according to any one of Statements 1 to 17, further comprising formulating the isolated CTCs, lysate thereof or one or more tumor antigens thereof into a tumor vaccine, optionally wherein the tumor vaccine further comprises dendritic cells.

Statement 19. The method according to any one of Statements 1 to 17, further comprising subjecting the isolated CTCs to biochemical analysis, mutation analysis, transcriptomic analysis and/or proteomic analysis.

Statement 20. A method for the diagnosis, prognosis or monitoring of a neoplastic disease in a subject, comprising detecting or quantifying CTCs in the subject by the method as defined in any one of Statements 1 to 17.

Statement 21. A method for determining the metastatic potential of a neoplastic disease in a subject comprising detecting or quantifying CTCs in the subject by the method as defined in any one of Statements 1 to 17, wherein the presence of CTCs in the subject identifies the neoplastic disease as having metastatic potential.

Statement 22. A method for determining the relapse of a neoplastic disease in a subject comprising detecting or quantifying CTCs in the subject by the method as defined in any one of Statements 1 to 17, wherein the presence of CTCs in the subject identifies that the neoplastic disease has relapsed.

Statement 23. A method for determining whether a subject is in need of an anti-cancer therapy, comprising detecting or quantifying CTCs in the subject by the method as defined in any one of Statements 1 to 17, wherein the presence of CTCs in the subject identifies the subject as being in need of an anti-cancer therapy.

Statement 24. A method for determining the efficacy of an anti-cancer therapy in a subject having a neoplastic disease, comprising detecting or quantifying CTCs in the subject by the method as defined in any one of Statements 1 to 17 before and during or subsequent to the therapy, wherein reduced quantity of CTCs in the subject during or subsequent to the therapy compared to before the therapy identifies said therapy as efficacious.

Statement 25. A kit of parts or an article of manufacture selected from the group consisting of:
a) a kit of parts or an article of manufacture comprising:
  one or more agents capable of specifically binding to CD321; and
  one or more agents capable of specifically binding to at least one pan-leukocyte marker;
b) a kit of parts or an article of manufacture comprising:
  one or more agents capable of specifically binding to CD321; and
  one or more agents capable of specifically binding to at least one thrombocyte marker; or
c) a kit of parts or an article of manufacture comprising:
  one or more agents capable of specifically binding to CD321;
  one or more agents capable of specifically binding to at least one pan-leukocyte marker; and
  one or more agents capable of specifically binding to at least one thrombocyte marker.

Statement 26. The kit of parts or article of manufacture according to Statement 25, wherein:
a) said pan-leukocyte marker is selected from the group consisting of CD45, LSP1, CD48, and combinations thereof;
b) said thrombocyte marker is selected from the group consisting of CD36, CD41, CD42a, CD42b, CD61, and combinations thereof;
c) said pan-leukocyte marker is selected from the group consisting of CD45, LSP1, CD48, and combinations thereof, and said thrombocyte marker is selected from the group consisting of CD36, CD41, CD42a, CD42b, CD61, and combinations thereof;
d) said pan-leukocyte marker is CD45;
e) said thrombocyte marker is CD42a; or
f) said pan-leukocyte marker is CD45 and said thrombocyte marker is CD42a.

Statement 27. The kit of parts or article of manufacture according to Statement 25 or 26, wherein the one or more agents are configured for use in a technique selected from the group consisting of flow cytometry, mass cytometry, fluorescence activated cell sorting, fluorescence microscopy, affinity separation, magnetic cell separation, microfluidic separation, and combinations thereof.

Statement 28. The kit of parts or article of manufacture according to any one of Statements 25 to 27, wherein the one or more agents are, each independently, one or more antibodies, antibody fragments, antibody-like protein scaffolds, or aptamers.

Further markers set forth in the table in Example 1 are also postulated as useful in applications corresponding to those described in this specification for CD321. These markers include, in particular, CD40, CD49e, CD146, Beta2 microglobulin, and combinations thereof.

Hence, the present application also provides aspects and embodiments as set forth in the following Statements 1'-31':

Statement 1'. A method for detecting or quantifying tumor cells in a biological sample from a subject, and optionally for isolating the tumor cells from the biological sample, the method comprising detecting the expression of a marker selected from the group consisting of CD321, CD40, CD49e, CD146, Beta2, and combinations thereof by tumor cells in the biological sample, and optionally isolating tumor cells expressing said marker from the biological sample.

Statement 2'. The method according to Statement 1', wherein the biological sample is tumor biopsy or fine-needle aspirate, or resected tumor tissue.

Statement 3'. The method according to Statement 1', for detecting or quantifying circulating tumor cells (CTCs) in a biological sample from a subject, and optionally for isolating said CTCs from the biological sample, comprising detecting the expression of a marker selected from the group consisting of CD321, CD40, CD49e, CD146, Beta2, and combinations thereof by circulating non-hematopoietic cells in the biological sample, wherein the expression of said marker by a circulating non-hematopoietic cell identifies said cell as a circulating tumor cell, and optionally isolating the CTCs expressing said marker from the biological sample.

Statement 4'. The method according to Statement 3', wherein the biological sample comprises circulating cells from blood, urine, feces, lymph or another exudate or secretory fluid of the subject, preferably from peripheral blood of the subject.

Statement 5'. The method according to Statements 3' or 4', wherein a circulating tumor cell positive for said marker is identified as non-hematopoietic by the absence of expression of at least one pan-leukocyte marker and of at least one thrombocyte marker by said cell.

Statement 6'. The method according to any one of Statements 3' to 5' comprising:
a) providing a biological sample from the subject, said biological sample comprising circulating cells from the subject, preferably circulating cells from blood, urine, feces, lymph or another exudate or secretory fluid of the subject, more preferably from peripheral blood of the subject;
b) detecting in said biological sample non-hematopoietic cells negative for at least one pan-leukocyte marker and negative for at least one thrombocyte marker;
c) detecting the expression of the marker selected from the group consisting of CD321, CD40, CD49e, CD146, Beta2, and combinations thereof by the cells as detected in b), wherein the expression of said marker by a cell as detected in b) identifies said cell as a circulating tumor cell.

Statement 7'. The method according to Statement 5' or 6', wherein:
a) said pan-leukocyte marker is selected from the group consisting of CD45, LSP1, CD48, and combinations thereof;
b) said thrombocyte marker is selected from the group consisting of CD36, CD41, CD42a, CD42b, CD61, and combinations thereof;
c) said pan-leukocyte marker is selected from the group consisting of CD45, LSP1, CD48, and combinations thereof, and said thrombocyte marker is selected from the group consisting of CD36, CD41, CD42a, CD42b, CD61, and combinations thereof;
d) said pan-leukocyte marker is CD45;
e) said thrombocyte marker is CD42a; or
f) said pan-leukocyte marker is CD45 and said thrombocyte marker is CD42a.

Statement 8'. The method according to any one of Statements 1' to 7', wherein the tumor is a solid tumor.

Statement 9'. The method according to any one of Statements 1' to 8', wherein the tumor is of epithelial, mesenchymal or melanocyte origin.

Statement 10'. The method according to any one of Statements 1' to 9', wherein the subject is human.

Statement 11'. The method according to any one of Statements 1' to 10', wherein detecting the expression of said marker comprises detecting the marker protein or the marker mRNA or both.

Statement 12'. The method according to any one of Statements 1' to 11', wherein the tumor cells or CTCs are detected, quantified or isolated using a technique selected from the group consisting of flow cytometry, mass cytometry, fluorescence activated cell sorting, fluorescence microscopy, affinity separation, magnetic cell separation, microfluidic separation, and combinations thereof.

Statement 13'. The method according to Statement 12', wherein the technique employs one or more agents capable of specifically binding to the marker selected from the group consisting of CD321, CD40, CD49e, CD146, Beta2, and combinations thereof.

Statement 14'. The method according to Statement 12' or 13', wherein the technique further employs one or more agents capable of specifically binding to the at least one pan-leukocyte marker and one or more agents capable of specifically binding to the at least one thrombocyte marker.

Statement 15'. The method according to Statement 13' or 14', wherein the one or more agents are, each independently, one or more antibodies, antibody fragments, antibody-like protein scaffolds, or aptamers.

Statement 16'. The method according to any one of Statements 1 to 11', wherein the tumor cells or CTCs are detected, quantified or isolated using a technique which employs one or more agents capable of specifically binding to the marker selected from the group consisting of CD321, CD40, CD49e, CD146, Beta2, and combinations thereof.

Statement 17'. The method according to Statement 16', wherein the technique further employs one or more agents capable of specifically binding to the at least one pan-leukocyte marker and one or more agents capable of specifically binding to the at least one thrombocyte marker.

Statement 18'. The method according to Statement 16' or 17', wherein the one or more agents are, each independently, one or more antibodies, antibody fragments, antibody-like protein scaffolds, or aptamers.

Statement 19'. The method according to any one of Statements 16' to 18', wherein the tumor cells or CTCs are detected, quantified or isolated using a technique selected from the group consisting of flow cytometry, mass cytometry, fluorescence activated cell sorting, fluorescence microscopy, affinity separation, magnetic cell separation, microfluidic separation, and combinations thereof.

Statement 20'. The method according to any one of Statements 1' to 19', further comprising formulating the isolated tumor cells or CTCs, lysate thereof or one or more tumor antigens thereof into a tumor vaccine, optionally wherein the tumor vaccine further comprises dendritic cells.

Statement 21'. The method according to any one of Statements 1' to 19', further comprising subjecting the isolated tumor cells or CTCs to biochemical analysis, mutation analysis, transcriptomic analysis and/or proteomic analysis.

Statement 22'. A method for the diagnosis, prognosis or monitoring of a neoplastic disease in a subject, comprising detecting or quantifying tumor cells or CTCs in the subject by the method as defined in any one of Statements 1' to 19'.

Statement 23'. A method for determining the metastatic potential of a neoplastic disease in a subject comprising detecting or quantifying tumor cells or CTCs in the subject by the method as defined in any one of Statements 1' to 19', wherein the presence of tumor cells or CTCs in the subject identifies the neoplastic disease as having metastatic potential.

Statement 24'. A method for determining the relapse of a neoplastic disease in a subject comprising detecting or quantifying tumor cells or CTCs in the subject by the method as defined in any one of Statements 1' to 19', wherein the presence of tumor cells or CTCs in the subject identifies that the neoplastic disease has relapsed.

Statement 25'. A method for determining whether a subject is in need of an anti-cancer therapy, comprising detecting or quantifying tumor cells or CTCs in the subject by the method as defined in any one of Statements 1' to 19', wherein the presence of tumor cells or CTCs in the subject identifies the subject as being in need of an anti-cancer therapy.

Statement 26'. A method for determining the efficacy of an anti-cancer therapy in a subject having a neoplastic disease, comprising detecting or quantifying tumor cells or CTCs in the subject by the method as defined in any one of Statements 1' to 19' before and during or subsequent to the therapy, wherein reduced quantity of tumor cells or CTCs in the subject during or subsequent to the therapy compared to before the therapy identifies said therapy as efficacious.

Statement 27'. A method for in situ imaging of tumor in a subject comprising administering to the subject an agent capable of specifically binding to a marker selected from the group consisting of CD321, CD40, CD49e, CD146, Beta2, and combinations thereof, said agent comprising a label detectable by an imaging modality, allowing said agent to specifically bind to said marker expressed by the cells of the tumor, and visualizing the tumor in the subject using said imaging modality.

Statement 28'. A kit of parts or an article of manufacture selected from the group consisting of:
a) a kit of parts or an article of manufacture comprising:
  one or more agents capable of specifically binding to a marker selected from the group consisting of CD321, CD40, CD49e, CD146, Beta2, and combinations thereof; and
  one or more agents capable of specifically binding to at least one pan-leukocyte marker;
b) a kit of parts or an article of manufacture comprising:
  one or more agents capable of specifically binding to a marker selected from the group consisting of CD321, CD40, CD49e, CD146, Beta2, and combinations thereof; and
  one or more agents capable of specifically binding to at least one thrombocyte marker; or
c) a kit of parts or an article of manufacture comprising:
  one or more agents capable of specifically binding to a marker selected from the group consisting of CD321, CD40, CD49e, CD146, Beta2, and combinations thereof;
  one or more agents capable of specifically binding to at least one pan-leukocyte marker; and
  one or more agents capable of specifically binding to at least one thrombocyte marker.

Statement 29'. The kit of parts or article of manufacture according to Statement 28', wherein:
a) said pan-leukocyte marker is selected from the group consisting of CD45, LSP1, CD48, and combinations thereof;
b) said thrombocyte marker is selected from the group consisting of CD36, CD41, CD42a, CD42b, CD61, and combinations thereof;
c) said pan-leukocyte marker is selected from the group consisting of CD45, LSP1, CD48, and combinations thereof, and said thrombocyte marker is selected from the group consisting of CD36, CD41, CD42a, CD42b, CD61, and combinations thereof;
d) said pan-leukocyte marker is CD45;
e) said thrombocyte marker is CD42a; or
f) said pan-leukocyte marker is CD45 and said thrombocyte marker is CD42a.

Statement 30'. The kit of parts or article of manufacture according to Statement 28' or 29', wherein the one or more agents are configured for use in a technique selected from the group consisting of flow cytometry, mass cytometry, fluorescence activated cell sorting, fluorescence microscopy, affinity separation, magnetic cell separation, microfluidic separation, and combinations thereof.

Statement 31'. The kit of parts or article of manufacture according to any one of Statements 28' to 30', wherein the one or more agents are, each independently, one or more antibodies, antibody fragments, antibody-like protein scaffolds, or aptamers.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as follows in the spirit and broad scope of the appended claims.

The herein disclosed aspects and embodiments of the invention are further supported by the following non-limiting examples.

EXAMPLES

Example 1—CD321 is Consistently Expressed in Cell Lines, Patient-Derived Xenografts (PDX) and Primary Tumors The expression of 251 cell surface markers was evaluated in cells from a representative collection of cancer cell lines (SKMES squamous lung carcinoma cell line, A431 epidermoid carcinoma cell line), patient-derived xenografts (head & neck cancer PDX at third passage) and primary tumors (primary skin squamous cell carcinoma), compared to adult dermal fibroblasts. The following Table provides a semi-quantitative representation of the expression of said markers.

| Antigen | SKMES Lung | A431 skin | H&N PDX P3 | Primary skin SCC | Adult dermal fibroblasts |
|---|---|---|---|---|---|
| CD8b | — | B | — | NA | — |
| CD9 | xx | xx | xx | — | xx |
| CD10 | x | — | — | NA | xx |
| CD13 | xx | — | — | NA | xx |
| CD15 | — | — | x | NA | x? |
| CD24 | B | xx | — | — | — |
| CD29 | x | x | x | — | xx |
| CD30 | x | — | — | NA | — |
| CD36 | x | — | — | NA | — |
| CD39 | x | — | — | NA | — |
| CD40 | xx | xx | — | — | — |
| CD44 | B | xx | B | x | xx |
| CD46 | xx | xx | xx | — | xx |
| CD47 | xx | xx | xx | xx | xx |
| CD49a | — | x | — | NA | x |
| CD49b | — | xx | x | — | xx |
| CS49c | — | xx | xx | — | xx |
| CD49d | — | B | — | NA | xx |
| CD49e | xx | xx | — | — | — |
| CD49f | — | xx | x | — | — |
| CD51/61 | xx | — | x | — | x |
| CD54 | — | xx | — | NA | x |
| CD55 | — | xx | xx | x | xx |
| CD56 | — | xx | — | NA | xx |
| CD58 | — | — | xx | NA | xx |
| CD59 | xx | xx | xx | xx | x |
| CD61 | x | — | B | — | — |
| CD63 | xx | xx | xx | — | xx |
| CD66 | — | B | x | — | — |
| CD69 | x | — | — | NA | x |
| CD71 | xx | xx | xx | — | x |
| CD73 | xx | xx | NA | — | xx |
| CD77 | — | B | — | NA | B |
| CD81 | xx | xx | x | — | xx |
| CD91 | — | ? | — | NA | xx |
| CD95 | — | xx | xx | — | xx |
| CD98 | — | xx | xx | — | xx |
| CD99 | xx | x | — | — | xx |
| CD104 | xx | x | ? | — | — |
| CD107a | — | x | xx | — | xx |
| CD108 | — | x | — | NA | x |
| CD109 | — | x | — | NA | — |
| CD117 | — | — | B | NA | — |
| CD119 | — | x | — | NA | xx |
| CD127 | xx | — | — | NA | — |
| CD128 | xx | — | — | NA | — |
| CD130 | — | x | — | NA | xx |
| CD141 | — | xx | — | NA | xx |
| CD142 | — | xx | — | NA | xx |

| Antigen | SKMES Lung | A431 skin | H&N PDX P3 | Primary skin SCC | Adult dermal fibroblasts |
|---|---|---|---|---|---|
| CD146 | xx | B | xx | — | — |
| CD147 | xx | xx | xx | xx | xx |
| CD151 | x | B | xx | — | xx |
| CD164 | x | xx | xx | — | xx |
| CD165 | B | — | — | — | xx |
| CD166 | xx | xx | xx | — | xx |
| CD171 | x | ? | — | — | — |
| CD201 | — | xx | — | NA | xx |
| CD205 | — | x | — | NA | — |
| CD220 | — | — | xx | NA | — |
| CD221 | — | xx | xx | — | xx |
| CD227 | — | B | x | — | x |
| CD271 | — | x | — | NA | — |
| CD274 | xx | xx | — | — | — |
| CD321 | xx | xx | xx | x | — |
| CD326 | x | xx | xx | — | — |
| CD338 | — | x | — | NA | — |
| CD340 | x | xx | xx | — | x |
| B2M | xx | xx | xx | NA | — |
| CLA | — | x | — | NA | — |
| EGFR | xx | xx | — | — | xx |
| Dis-GD2 | B | — | — | NA | B |
| fMLP-R | x | — | — | NA | — |
| SSEA4 | B | xx | — | x | B |
| TRA-1-60 | B | — | — | NA | — |
| TRA-1-81 | B | — | — | NA | — |

'B' denotes 'bimodal expression', wherein the marker expression is heterogeneous, with some cells positive and others not.

CD321 was uncovered as reliably expressed by all tested cancer tissues but not expressed by adult dermal fibroblasts.

Figure 6:
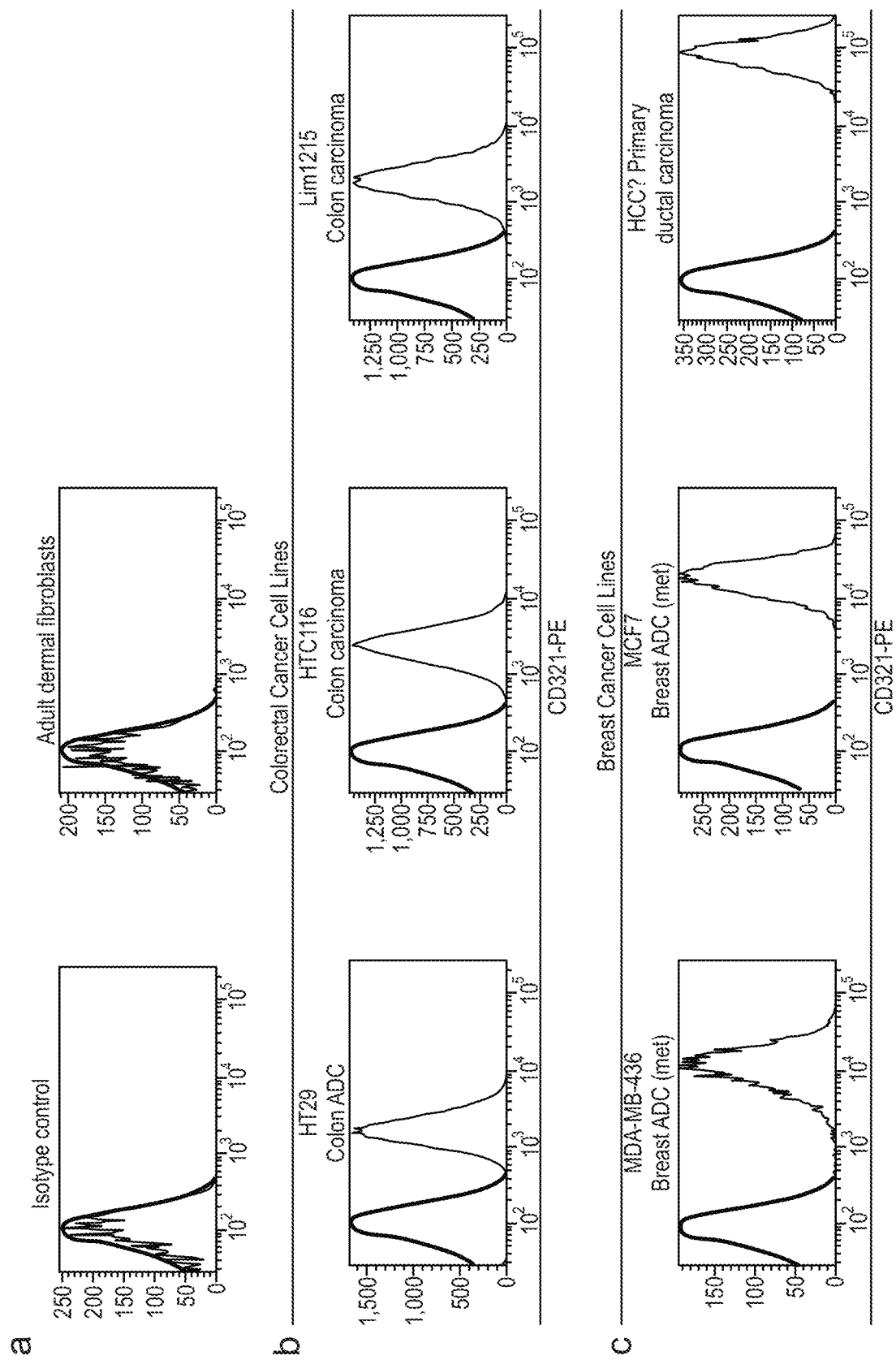
FIG. 6 illustrates that CD321 is homogeneously expressed in cell lines, patient-derived xenografts (PDX) and primary tumors. a, Isotype control and adult dermal fibroblasts show negative staining for CD321. b-d, Colorectal cancer cell lines (b), breast cancer cell lines (c) and lung cancer cell lines (d) homogeneously express high levels of CD321 (filled histograms). e, f, Melanoma cell lines homogeneously express CD321 at low levels. g, Endometrial, esophagus, vulvar and skin carcinoma cell lines homogeneously express high levels of CD321. The FACS plots are gated in single living cells. h, Patient Derived Xenografts at the first passage from different types of cancer homogeneously express CD321 (filled histograms). The FACS plots are gated in living cells, after exclusion of immune and endothelial cells of mouse and human origin. i, Primary lung and esophagus carcinomas express high levels of CD321 (filled histograms). The FACS plots are gated in single living cells, after exclusion of immune and endothelial cells and the majority of cancer associated fibroblasts. The empty histograms indicate the staining with isotype control.
Figure 6:
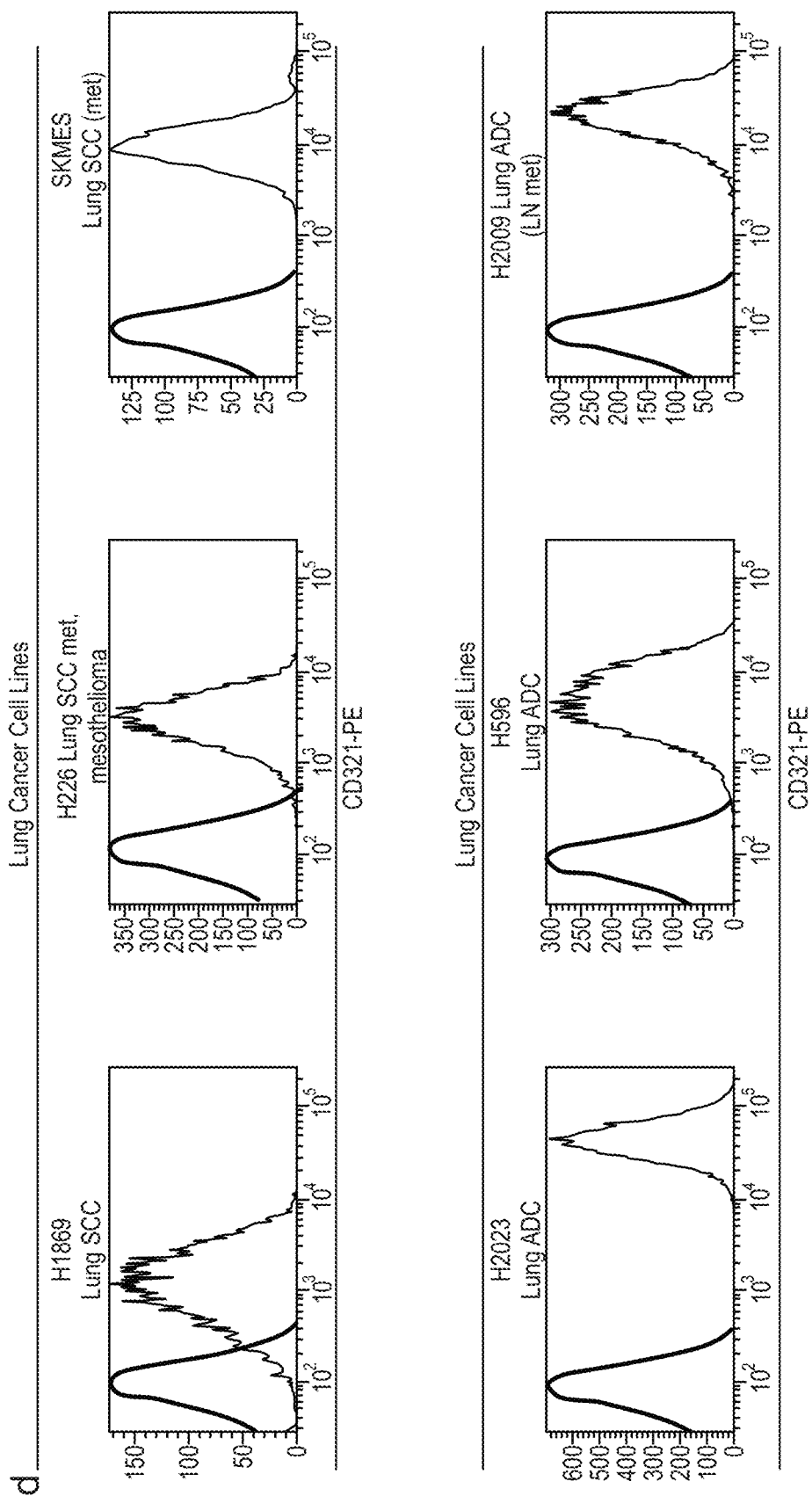
Figure 6:
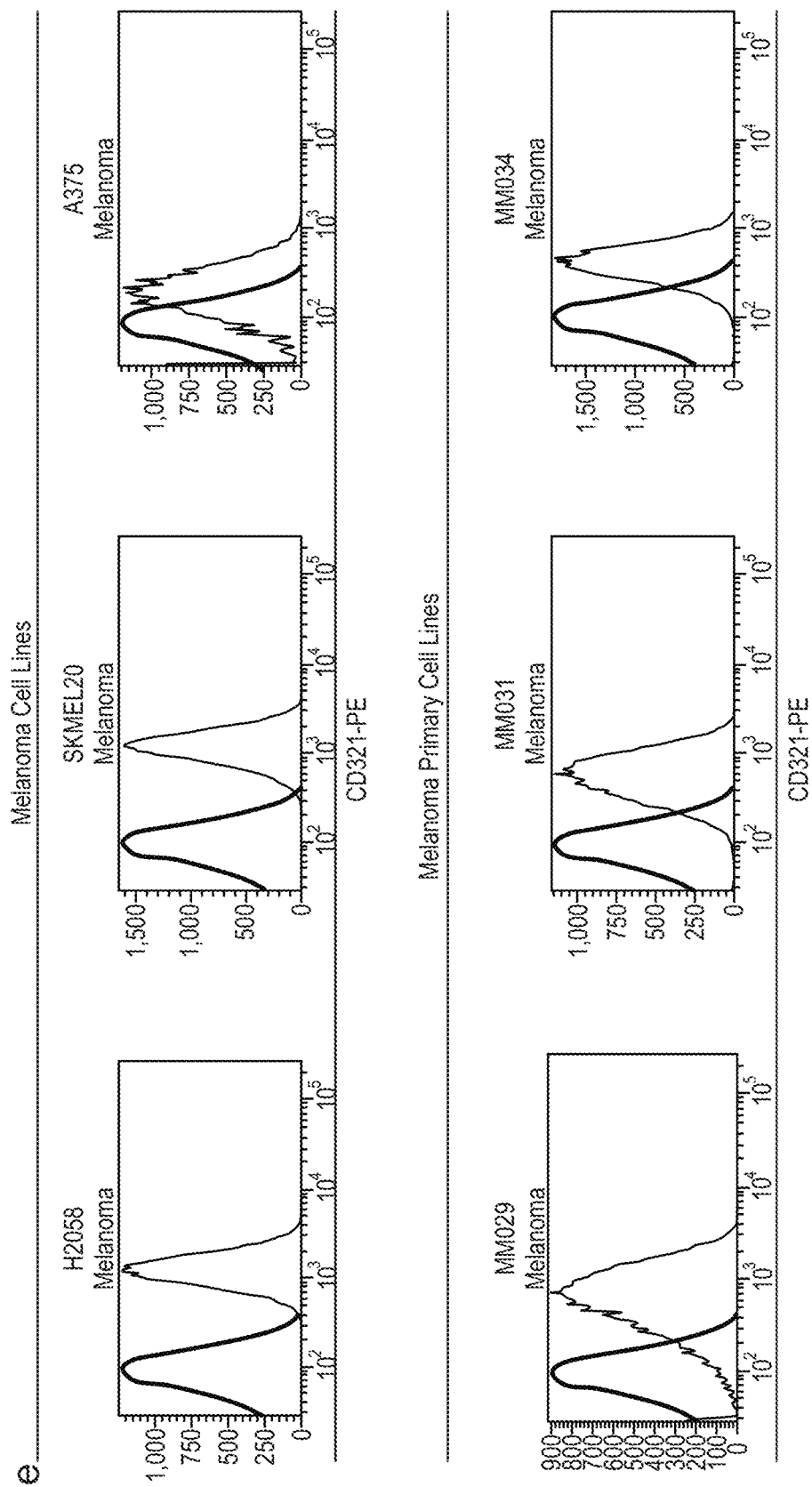
Figure 6:
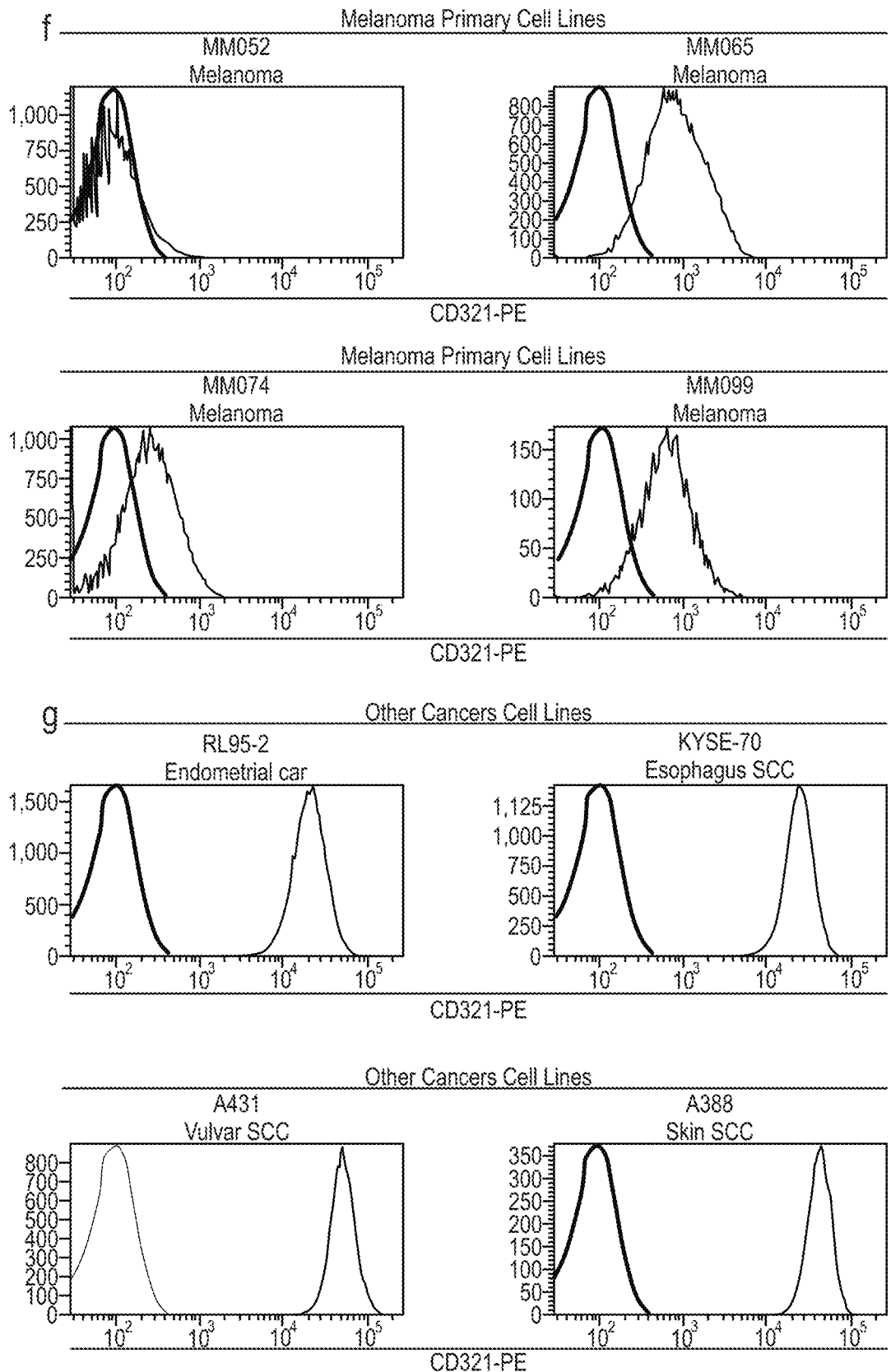
Figure 6:
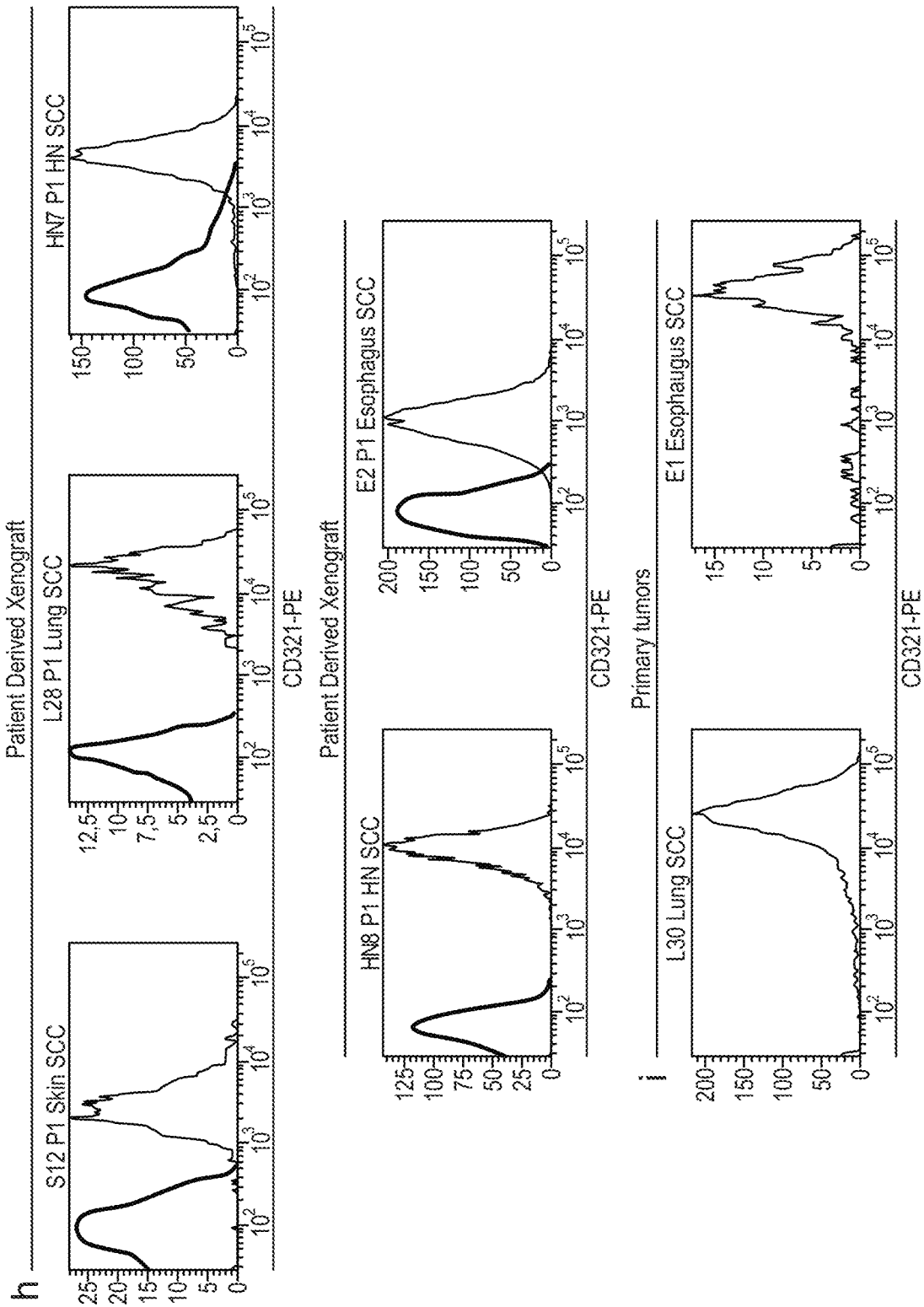

Additional extensive validation confirmed that CD321 was consistently expressed by cancer cell lines, patient-derived xenografts (PDX) and primary tumors (FIGS. 1 and 6).

Further markers set forth in the above table are also postulated as useful in applications corresponding to those described in this specification for CD321. These markers include, in particular, CD40, CD49e, CD146, Beta2 microglobulin (B2M), and combinations thereof.

Figure 2:
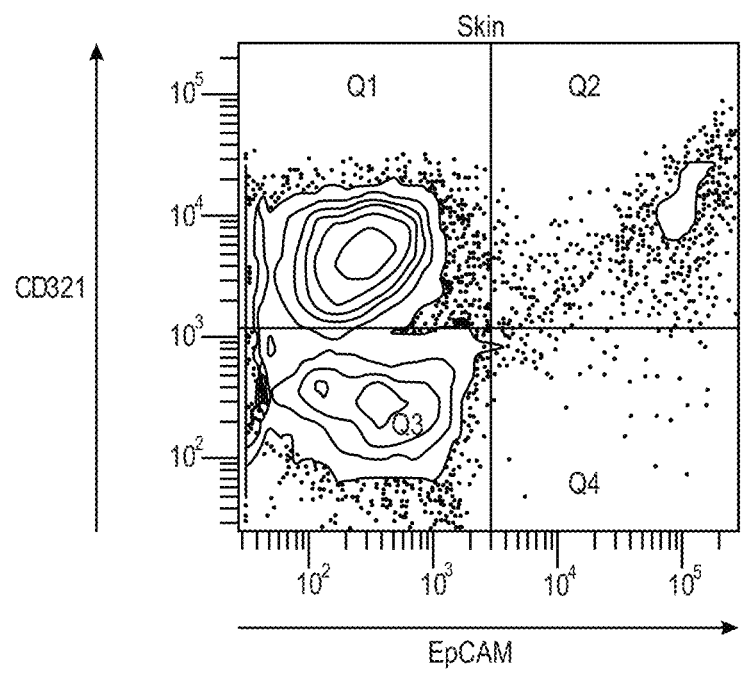
FIG. 2 illustrates that CD321 labels tumor cells with higher sensitivity compared to the classical epithelial marker EpCAM. Representative FACS plots (upper panels) and the respective quantification (lower panels) of CD321+EpCAM+ and CD321+EpCAM− tumor cells from primary tumors of skin (A), lung (B) and head & neck (C) cancer. The classical epithelial marker EpCAM, commonly used to identify cancer cells, always co-localized with CD321, while CD321 in all cases labeled a much higher number of cells, demonstrating that CD321 is able to detect tumor cells with higher sensitivity than the classical epithelial cell marker EpCAM. Plots are gated in single living cells after exclusion of immune and endothelial cells and the majority of cancer associated fibroblasts.
Figure 2:
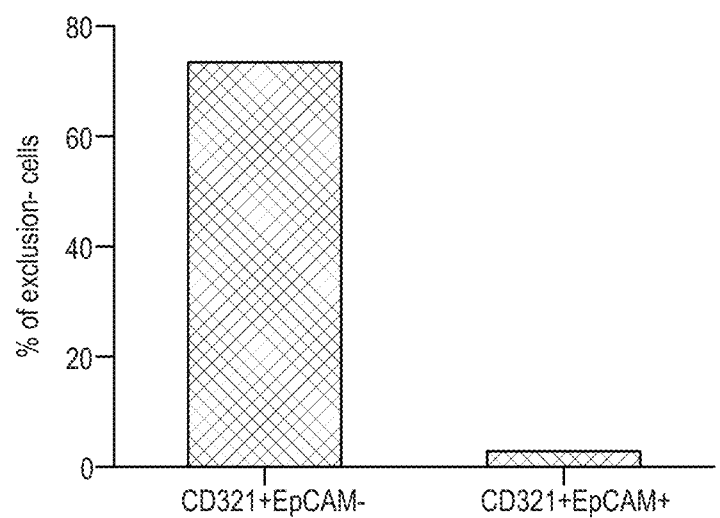
Figure 2:
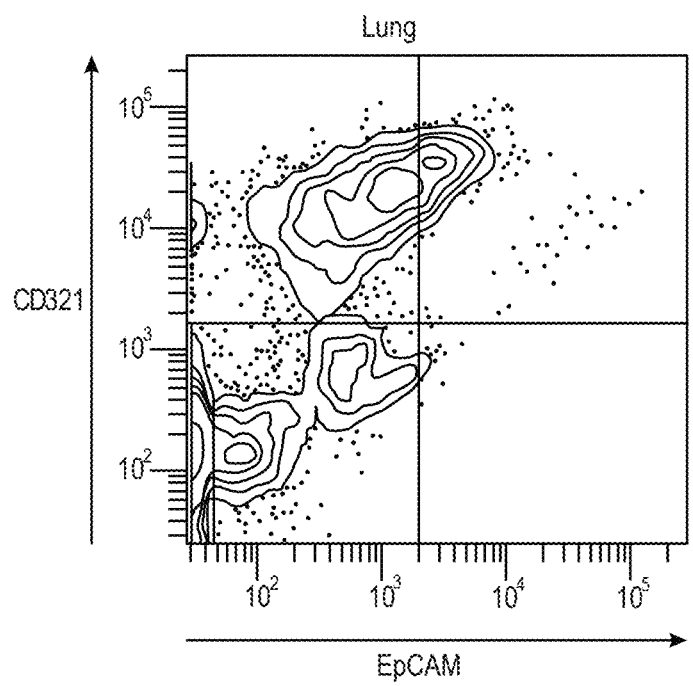
Figure 2:
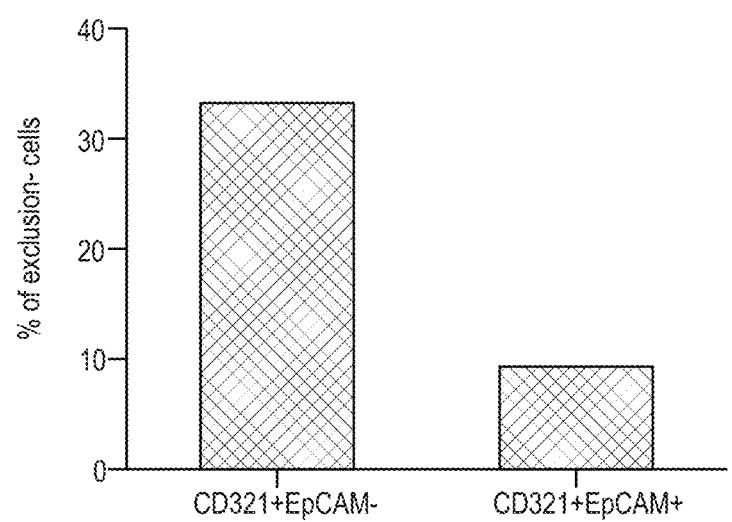
Figure 2:
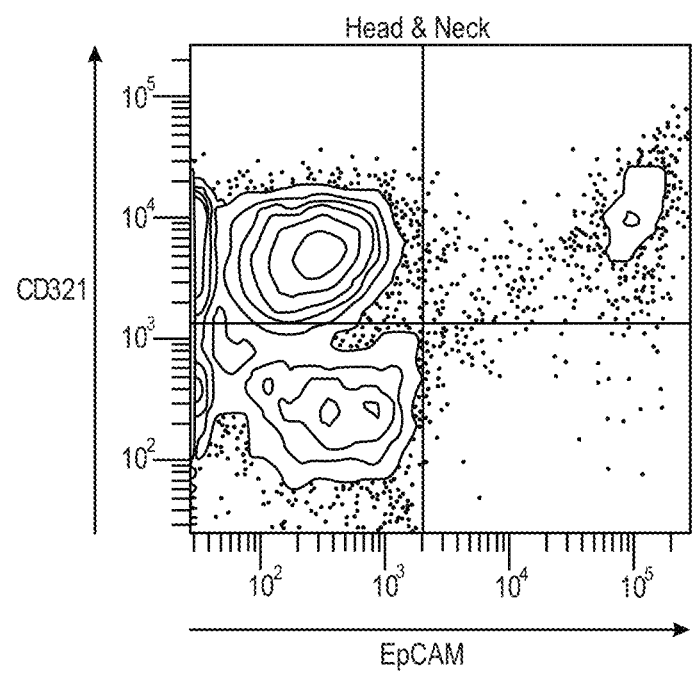
Figure 2:
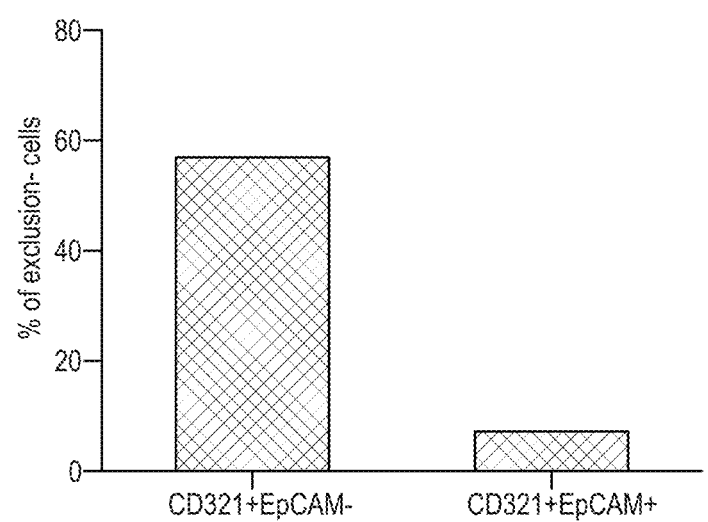
Figure 7:
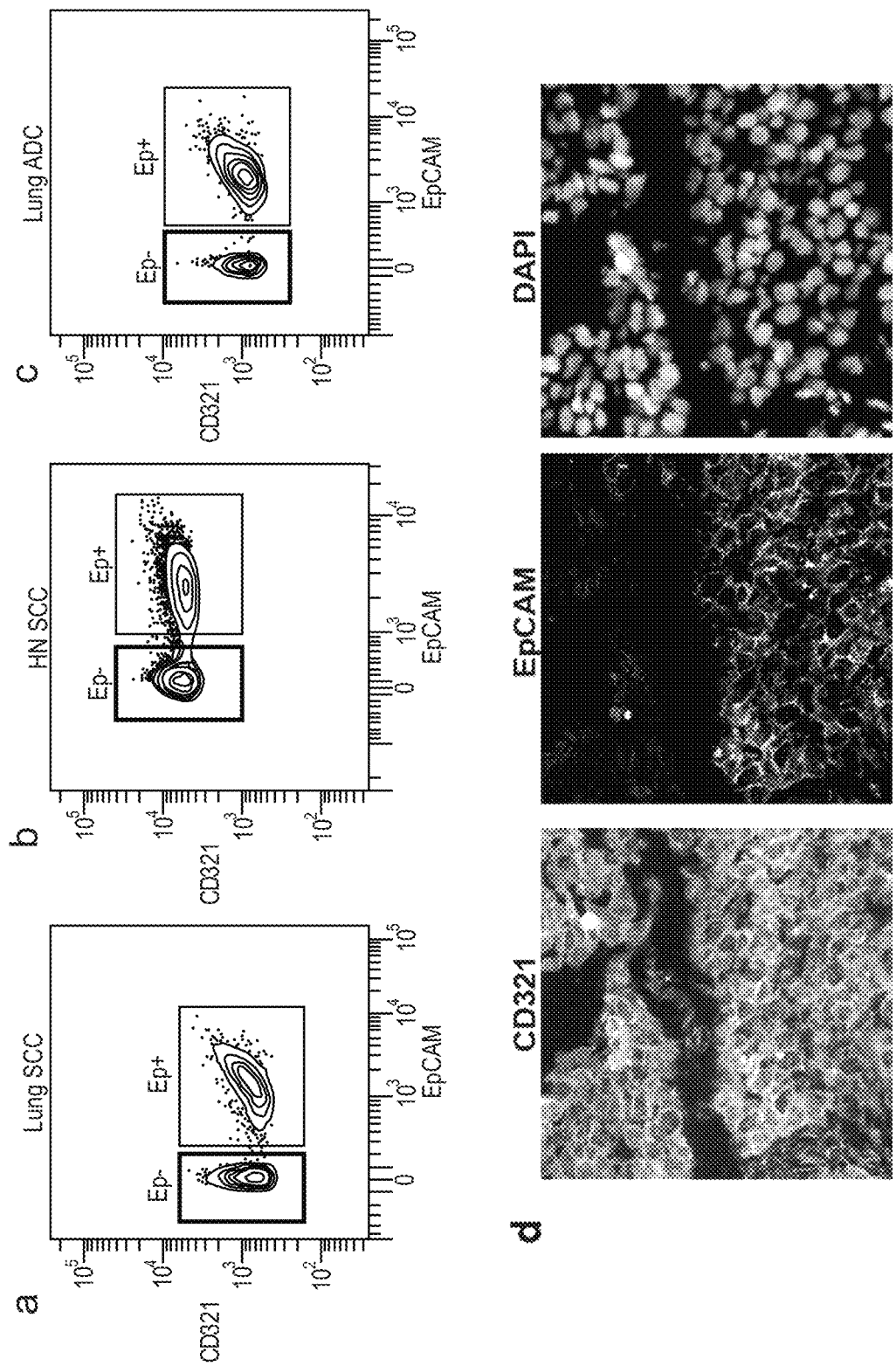
FIG. 7 illustrates that CD321 labels tumor cells with higher sensitivity compared to the classical epithelial marker EpCAM. a-c, Representative FACS plots of lung and head and neck carcinomas, showing the existence of CD321+EpCAM+ and CD321+EpCAM− tumor cells. This demonstrates that CD321 is able to detect tumor cells with higher sensitivity than the classical epithelial cell marker EpCAM. Plots are gated in single living cells after exclusion of immune and endothelial cells and the majority of cancer associated fibroblasts. d, Representative immunofluorescent images of lung cancer patient derived xenograft, showing the existence of CD321+EpCAM+ tumor cells and CD321+EpCAM− tumor cells.

Example 2—Comparison of CD321 Expression by Tumor Cells to Expression of Conventional Epithelial Markers The classical marker EpCAM is conventionally used to identify cancer cells. The expression of CD321 and EpCAM was compared in tumor cells from primary tumors of skin, lung and head & neck cancer. EpCAM always co-localized with CD321, while CD321 in all cases labeled a much higher number of cells, demonstrating that CD321 detected tumor cells with higher sensitivity than EpCAM (FIGS. 2 and 7).

Figure 3:
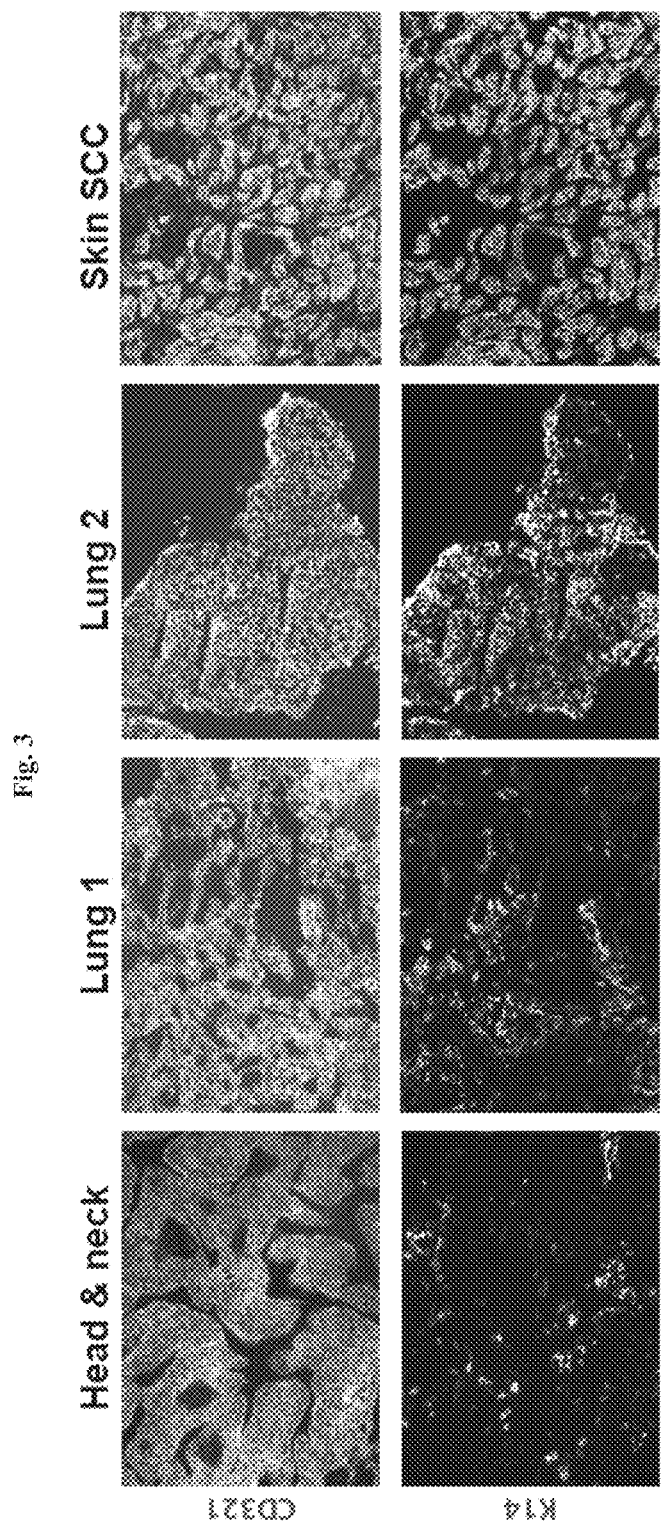
FIG. 3 illustrates that CD321 allows more sensitive identification of tumor cells than the classical epithelial marker Keratin-14. Representative immunofluorescent images of CD321 and Keratin-14 on sections of head & neck, lung and skin tumors. Note that Keratin-14 always co-localized with CD321, while CD321 was expressed in a greater proportion of cancer cells.

Furthermore, the expression of CD321 and the classical epithelial marker Keratin-14 was compared in tissue sections of head & neck, lung and skin tumors. Keratin-14 always co-localized with CD321, while CD321 was expressed in a greater proportion of cancer cells, demonstrating that CD321 detected tumor cells with higher sensitivity than Keratin-14 (FIG. 3).

Epithelial markers, such as EpCAM and cytokeratins, are lost during epithelial to mesenchymal transition (EMT), a process believed to be required for the extravasation and characteristic of tumor initiating cells.

Figure 4:
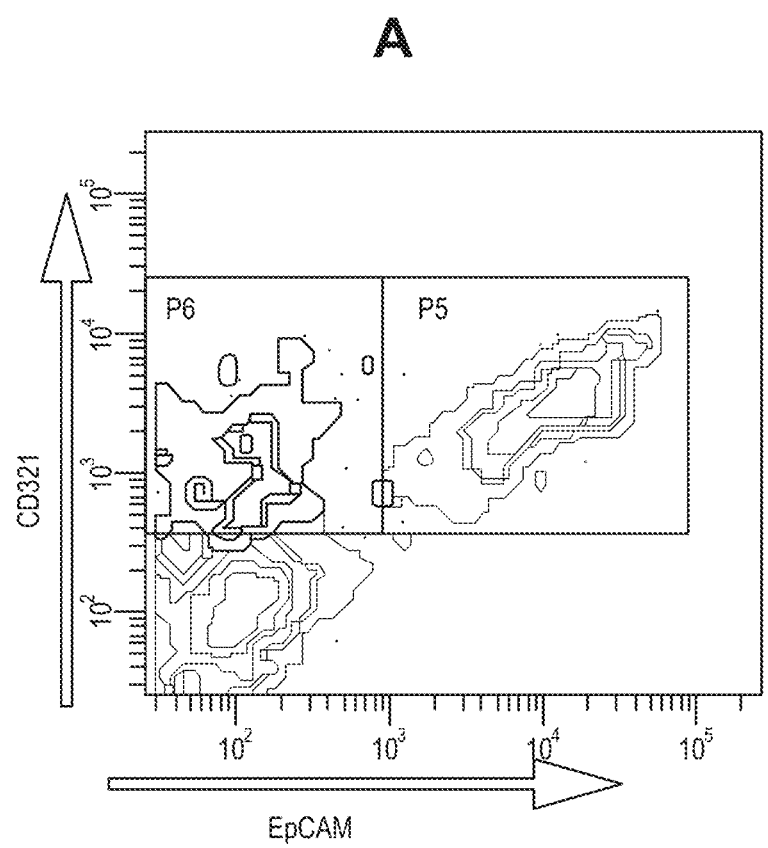
FIG. 4 illustrates that CD321 allows identification of tumor cells independently of their epithelial-mesenchymal transition (EMT) status. A. FACS strategy used for isolation of tumor epithelial cells (CD321+EpCAM+, gate P5) and tumor mesenchymal cells (CD321+EpCAM−, gate P6) from a primary lung SCC. Note that tumor cells were selected after exclusion of immune and endothelial cells, and most of the cancer associated fibroblasts. B, C. Relative expression of genes expressed in CD321+EpCAM− and CD321p+ EpCAM+ tumor cells, FACS-sorted as described in (A) (FACS strategy to isolate these subpopulations was to gate on single living cells, after exclusion of immune endothelial cells and the majority of cancer associated fibroblasts), estimated by RNA sequencing of the respective populations.
Figure 4:
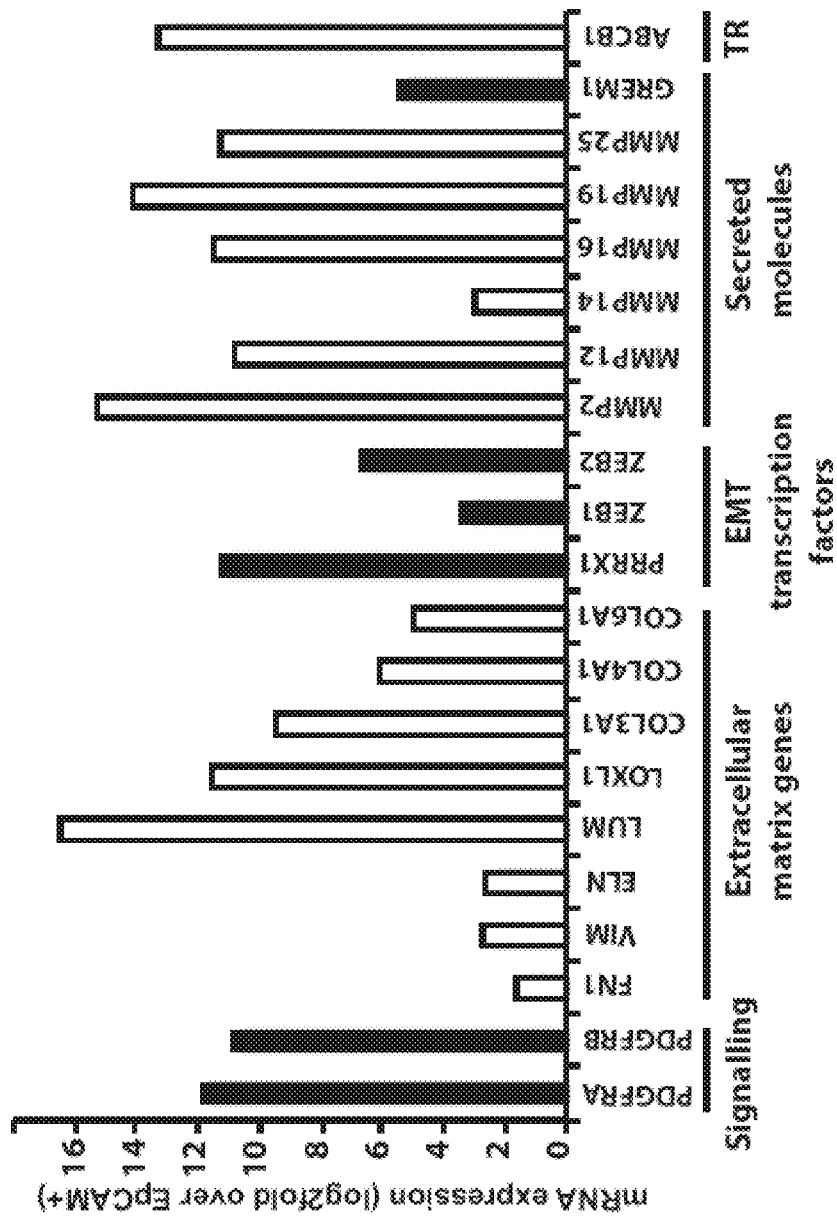
Figure 4:
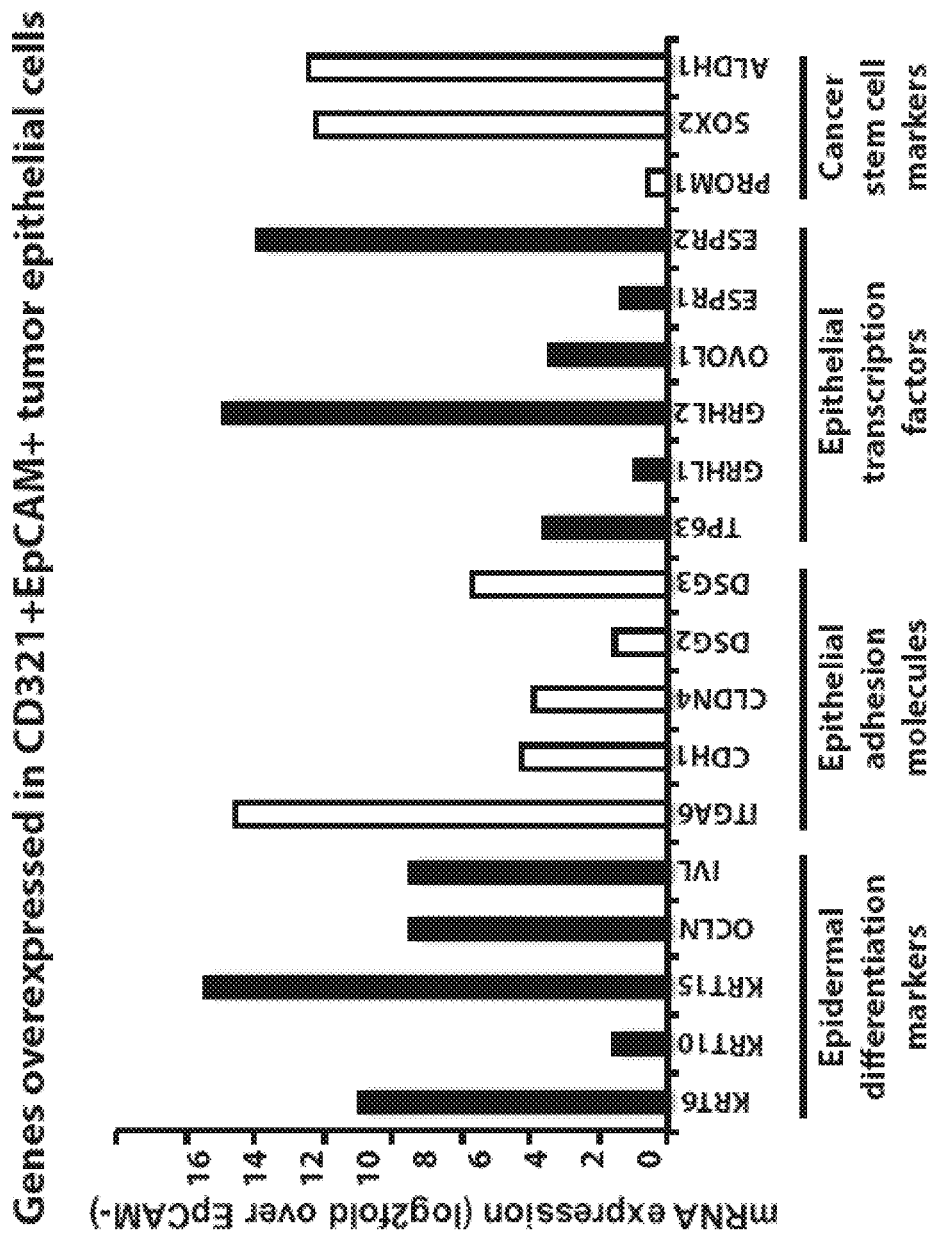

On the other hand, CD321 allowed identification of tumor cells independently of their EMT status (FIG. 4).

Example 3—CD321 Expression Allows Sensitive Identification of Circulating Tumor Cells (CTCs)

Figure 5:
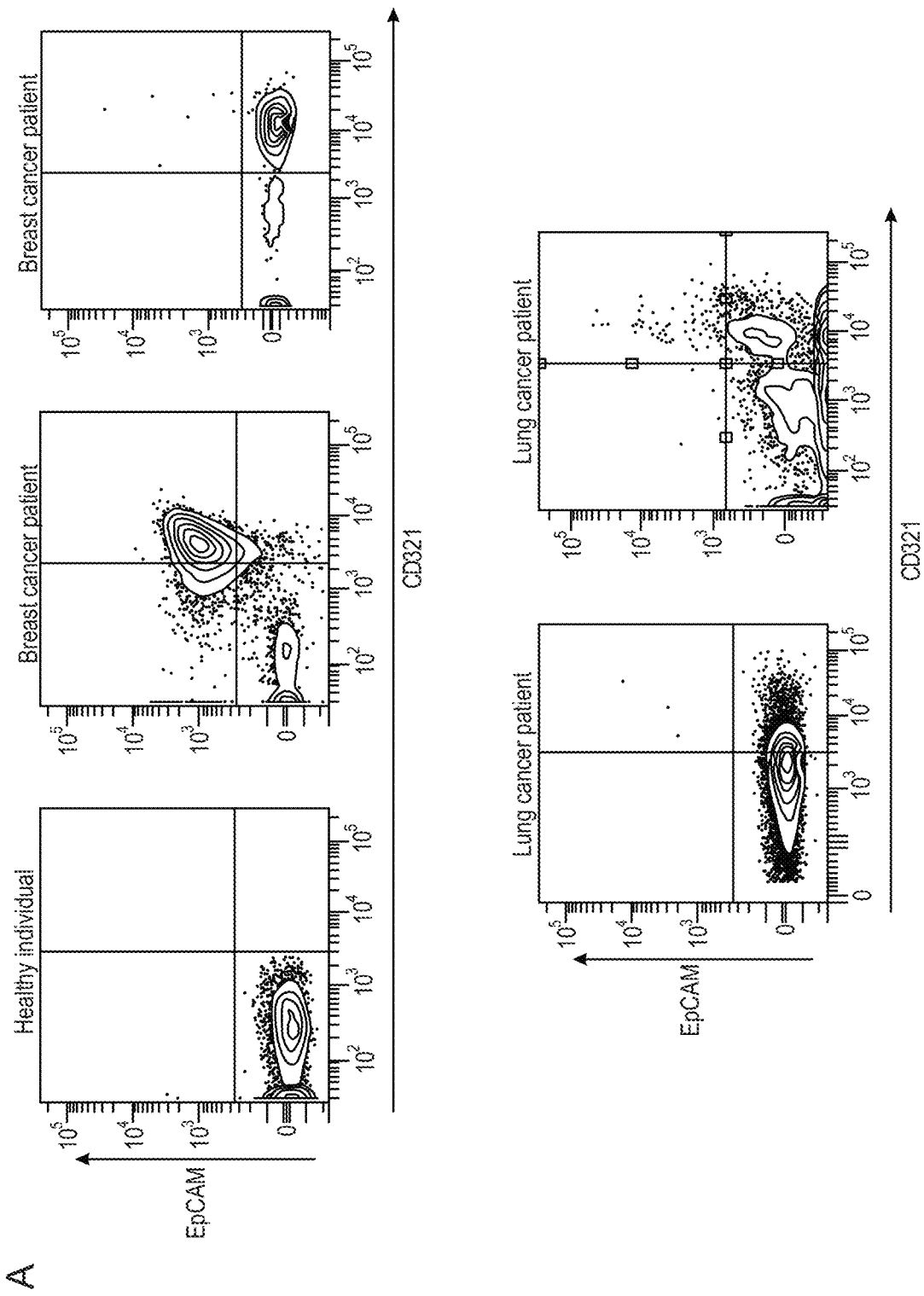
FIG. 5 illustrates that CD321 allows more sensitive identification of circulating tumor cells (CTCs) than EpCAM. A. Representative FACS plots of CD321 and EpCAM staining of the peripheral blood of normal donors and patients with breast or lung cancer. Plots were gated in single living cells after the exclusion of immune cells and platelets. Note that EpCAM+ cells were always CD321+, while CD321 also labeled additional cells, not marked by EpCAM. B. Histograms illustrating the presence of tumor cells in the peripheral blood and the lung tissue of a mouse grafted with human lung pleomorphic carcinoma (black columns) or non-transplanted (white columns), stained with human CD321 (that does not recognize mouse cells). Note the ability of the CD321 immunostaining to detect both cancer circulating cells of human origin and metastasis in the lung.
Figure 5:
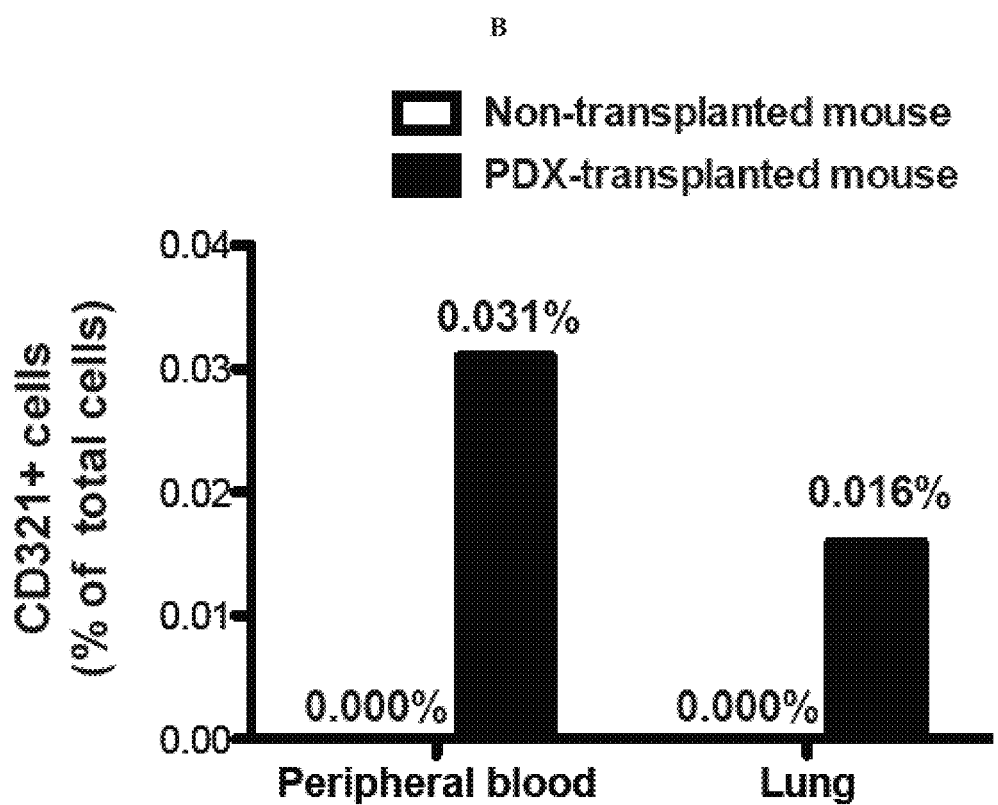

Cells from the peripheral blood of normal donors and patients with breast or lung cancer were stained for CD321 and EpCAM after exclusion of immune cells and platelets. EpCAM+ cells were always CD321+, while CD321 also labeled additional cells, not marked by EpCAM (FIG. 5A).

Cells from the peripheral blood and the lung tissue of a mouse grafted with human lung pleomorphic carcinoma were stained for human CD321. Human CD321+ cells were reliably detected both in circulation and in metastases in the lung (FIG. 5B).

CD321 allows sensitive identification of circulating tumor cells (CTCs) in human cancer patients subjects (FIG. 8a). CTC detection correlates with different stages of the cancer (FIG. 8b) and response to anti-cancer therapy (FIG. 8c).

Example 4—A Method for Detecting, Quantifying or Isolating Circulating Tumor Cells (CTCs)

One example of a method for detecting, quantifying or isolating circulating tumor cells (CTCs) embodying the principles of the present invention may include the following steps or operations.

A sample of peripheral blood (e.g., between 1 mL and 20 mL, e.g., 5 mL, 7.5 mL or 10 mL) from a human subject having or suspected of having cancer is provided. The blood sample is typically collected and stored in an anti-coagulant-containing (for example EDTA-containing) container or tube.

Red blood cells (RBCs) are excluded from the analysis by any one or a combination of the following procedures:
the peripheral blood sample is treated, prior to or following antibody staining (see below), in conventional ways to lyse RBCs, for example using commercially available RBC lysis buffers, such as 1× ACK (Ammonium Chloride Potassium) buffer (155 mM NH$_4$Cl, 10 mM KHCO$_3$, 0.1 mM EDTA, pH 7.3), or preferably using classical hypotonic shock to lyse red blood cells (adding a suitable volume of 0.2% w/v NaCl solution in water, allowing about 10-20 seconds until the red blood cells are lysed, and restoring isotonicity by adding the same volume of 1.6% w/v NaCl solution in water), or also preferably using a commercially available BD FACS™ Lysing solution (cat. no 349202); and/or
the peripheral blood sample is separated into the plasma, buffy coat and RBC fractions by centrifugation, and the buffy coat fraction containing leukocytes, thrombocytes and CTCs is used for downstream analysis.

Prior to antibody staining, dead cells may be excluded from the analysis, for example by contacting the sample with an adequate quantity of a dye which selectively labels dead vs. live cells. For example, when contacting intact (non-permeabilised) cell sample with Hoechst 33342, living cells will not incorporate the dye in their nuclei, whereas dead or dying cells will incorporate the dye in their nucleic. Afterwards, Hoechst-positive cells can be selected against, such as gated out in FACS, to allow the analysis to only be performed on living cells and not be confounded by non-specific antibody-binding by dead or dying cells.

Prior to antibody staining, the cells may but need not be collected and washed with a suitable buffer, such as 1× phosphate buffered saline (PBS) optionally with 0.5% w/v bovine serum albumin (BSA). Hence, antibody staining in whole blood samples or in buffy coat fractions without preceding washing is possible.

The cells are incubated with 1) a fluorescently labeled anti-human CD321 antibody, 2) a fluorescently labeled anti-human pan-leukocyte marker antibody and 3) a fluorescently labeled anti-human thrombocyte marker antibody in conditions conducive to antigen-antibody binding, for example in a suitable buffer such as 1× PBS with 2-3% w/v BSA or with 5-10% w/v fetal bovine serum (FBS) and with 1% w/v sodium azide, for at least 30 min at about 4° C. For example, the sample is incubated with 1) a fluorescently labeled anti-human CD321 antibody, 2) a fluorescently labeled anti-human CD45 antibody and 3) a fluorescently labeled anti-human CD42a antibody. A non-CD321 isotype antibody is used as a negative control. The antibodies are preferably monoclonal antibodies. Fluorophore under 1) is distinguishable from each of fluorophores under 2) and 3) by flow cytometry or fluorescence microscopy. Fluorophores under 2) and 3) may but need not be distinguishable from one another by flow cytometry or fluorescence microscopy. For example, fluorophore under 1) is allophycocyanin (APC) and fluorophores under 2) and 3) are R-Phycoerythrin (PE) or vice versa.

Typically, following incubation with the antibody, the cells are washed one to three times in a suitable buffer, such as 1× PBS with 0.5% w/v BSA and 1% w/v sodium azide to ensure specificity of antibody binding.

The so-treated cells are analyzed by conventional flow cytometry or manual or (semi-)automated fluorescence microscopy, and cells positive for fluorophore 1) and negative for fluorophores 2) and 3), which constitute CD321-positive CTCs, are detected and counted. The flow cytometry or fluorescence microscopy data is suitably represented for example in a tabular form or as a monovariate or bivariate histogram. The CTC load can be suitably represented, e.g., as CTC count per sample or per 1 mL blood.

Optionally, fluorescence activated cell sorting (FACS) may be employed to sort and isolate the CTCs.

Example 5—A Method for Detecting, Quantifying or Isolating Circulating Tumor Cells (CTCs)

Another example of a method for detecting, quantifying or isolating circulating tumor cells (CTCs) embodying the principles of the present invention may include the following steps or operations.

A sample of peripheral blood (e.g., between 1 mL and 20 mL, e.g., 5 mL, 7.5 mL or 10 mL) from a human subject having or suspected of having cancer is provided. The blood sample is typically collected and stored in an anti-coagulant-containing (for example EDTA-containing) container or tube.

The sample is incubated with ferrofluid particles conjugated with a first anti-human CD321 antibody in conditions conducive to antigen-antibody binding. Cells bound by the first anti-human CD321 antibody are immunomagnetically enriched. The CD321-ferrofluid-labeled cells are incubated with 1) a second anti-human CD321 antibody, which is fluorescently labeled and wherein the first and second anti-human CD321 antibodies bind non-competitively to CD321, 2) a fluorescently labeled anti-human pan-leukocyte marker antibody, for example a fluorescently labeled anti-human CD45 antibody, and 3) a suitable cell-permeant nuclear counterstain, such as a DNA-binding dye, for example 4',6-diamidino-2-phenylindole (DAPI) or Hoechst 33342. The antibodies are preferably monoclonal antibodies. Fluorophore under 1) is distinguishable from fluorophore under 2) by flow cytometry or fluorescence microscopy. For example, fluorophore under 1) is allophycocyanin (APC) and fluorophore under 2) is R-Phycoerythrin (PE) or vice versa.

Following any washing and magnetic separation of the fluorescently-labeled cells, the cells are analyzed by semi-automated fluorescent microscopy, such as using CellTracks Analyzer II® (Janssen Diagnostics, LLC). CTCs are defined as nucleated cells staining positively for CD321 and negatively for CD45 and are enumerated per set volume of the whole blood sample (e.g., per 1 mL or per 7.5 mL of blood).

Example 6—A Method for Detecting, Quantifying or Isolating Circulating Tumor Cells (CTCs)

Figure 8:
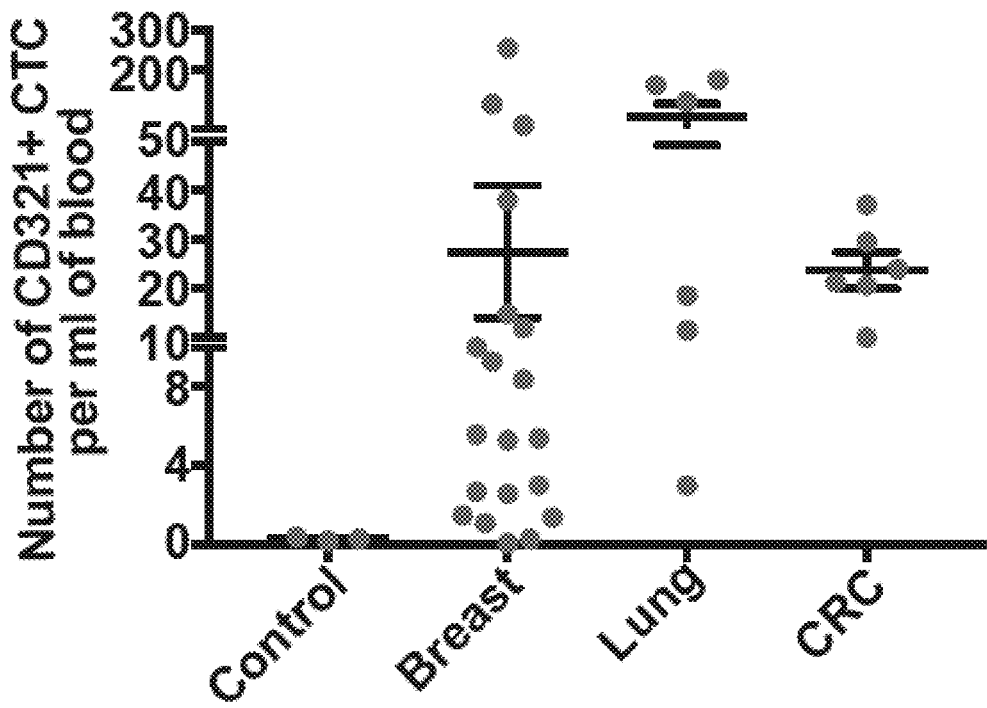
FIG. 8 illustrates that CD321 allows sensitive identification of circulating tumor cells (CTCs) in human subjects. a, Dot plot showing the number of CD321+ circulating tumor cells in healthy human donor, and human patients with breast, lung and colorectal cancers. Mean±SEM. The CD321+ circulating tumor cells were enumerated gating on single living cells, after lysis of red blood cells and exclusion of immune cells and platelets. b, Dot plot showing the number of CD321+ circulating tumor cells in healthy donor and human patients with lung cancer in different stages of the disease, showing a strong correlation between the number of circulating CD321+ cells and the stage. Mean±SEM. The CD321+ circulating tumor cells were enumerated gating on single living cells, after lysis of red blood cells and exclusion of immune cells and platelets. c, Dot plot showing the number of CD321+ circulating tumor cells in human patients with advanced breast cancer before and after anti-cancer therapy, showing correlation between the number of CD321+ circulating tumor cells and response to therapy. The CD321+ circulating tumor cells were enumerated gating on single living cells, after lysis of red blood cells and exclusion of immune cells and platelets.
Figure 8:
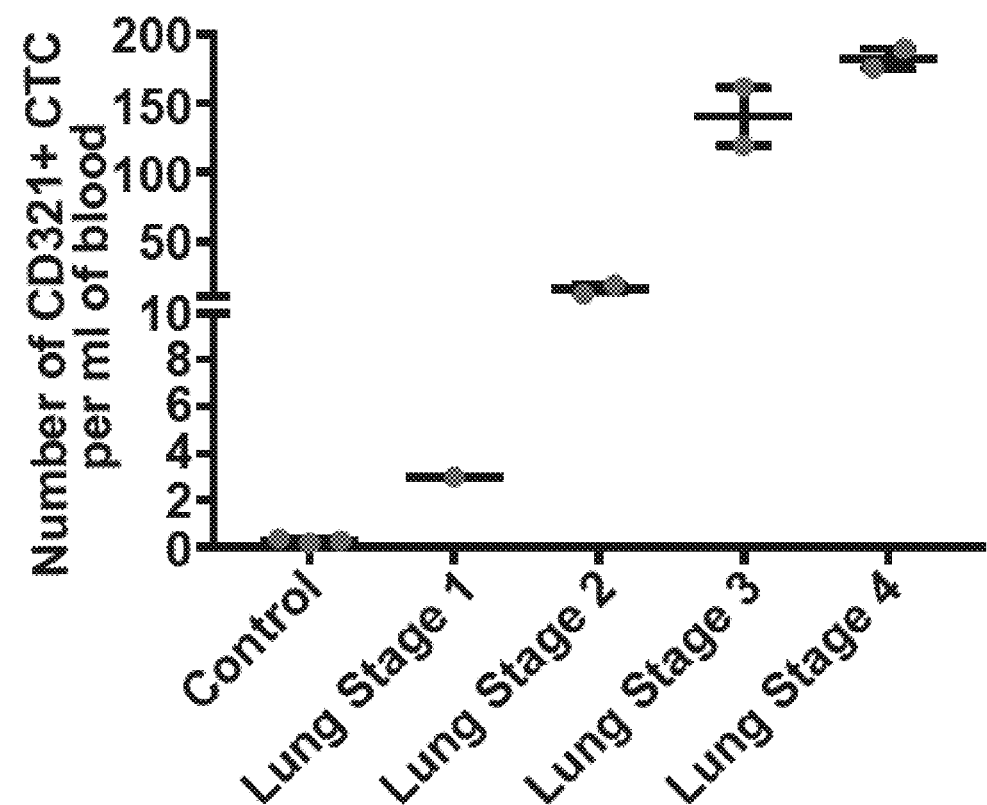
Figure 8:
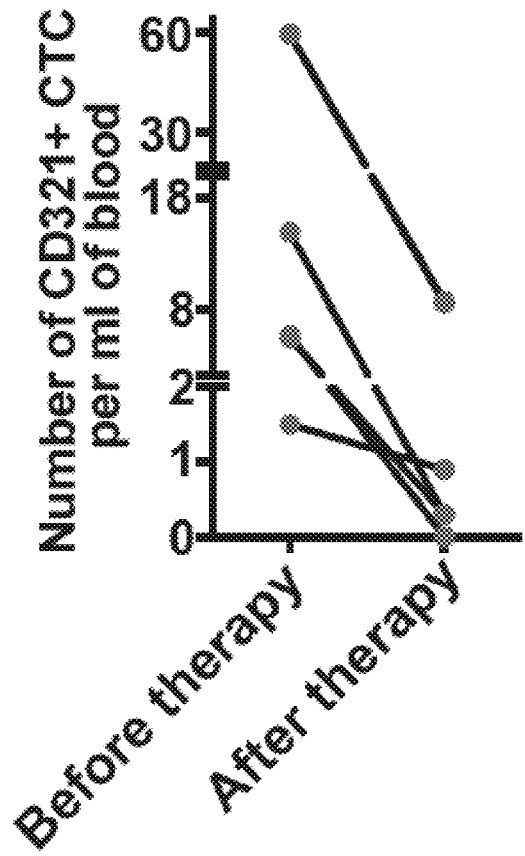

Further examples of methods for detecting, quantifying or isolating circulating tumor cells (CTCs) embodying the principles of the present invention, in particular used to collect the data on CTCs in human blood samples in the previous examples, such as those of FIG. 8, included the following steps or operations.

Method Using BD Lysis Buffer

Samples of 7.5 ml to 10 ml of blood were processed and analyzed using the following protocol instructions:
 Transfer the blood to 50 ml Falcon tube and add FACS buffer (PBS+2% v/v FBS)
 Centrifuge at 350 g for 10 min
 Carefully discard the supernatant to not disturb the cell pellet
 Repeat the wash with FACS buffer 1 more time
 Perform lysis of red blood cells with 1× BD FACS™ Lysing solution (cat. no 349202) at room temperature for 10 minutes (BD lysis buffer contains PFA so the cells are fixed and permeabilized)
 Centrifuge at 350 g for 10 min
 Discard supernatant
 Re-suspend the cell pellet in appropriate volume of FACS buffer (depending on the number of cells, usually 300-400 µl)
 Add antibodies: anti-human CD321-PE (BD cat #552556) (dilution 1:50), anti-human Epcam-APC (BD cat #347200)(dilution 1:50), anti-human CD45-BV421 (BD cat #563879)(dilution 1:100), anti-human CD42a-FITC (BD cat #558818)(dilution 1:50)
 Incubate on ice at 4 degrees and in dark for 30 min
 Wash with FACS buffer
 Re-suspend in 300-400 µl of FACS buffer and analyze by FACS Method Using Hypotonic RBC Lysis Samples of 7.5 ml to 10 ml of blood were processed and analyzed using the following protocol instructions:
 Add 25 ml of NaCl 0.2% w/v per 1 ml of blood
 Wait 10 seconds
 Add 25 ml of NaCl 1.6% w/v per 1 ml of blood
 Centrifuge at 350 g for 10 min
 Discard supernatant
 Proceed with the staining and FACS analysis as described above in the BD lysis buffer protocol In this protocol, after the last wash of the cells and before the analysis Hoechst 33342 dye 1:2000 is added to exclude dead cells.

CITATION LIST

Binz et al.: Engineering novel binding proteins from nonimmunoglobulin domains. Nat Biotechnol 2005, 23:1257-1268.

Gebauer and Skerra: Engineered protein scaffolds as next-generation antibody therapeutics. Curr Opin Chem Biol. 2009, 13:245-55.

Gill and Damle: Biopharmaceutical drug discovery using novel protein scaffolds. Curr Opin Biotechnol 2006, 17:653-658.

Koide and Koide: Monobodies: antibody mimics based on the scaffold of the fibronectin type III domain. Methods Mol Biol 2007, 352:95-109.

Kolmar: Alternative binding proteins: biological activity and therapeutic potential of cystine-knot miniproteins. FEBS J 2008, 275:2684-2690.

Nixon and Wood: Engineered protein inhibitors of proteases. Curr Opin Drug Discov Dev 2006, 9:261-268.

Nygren: Alternative binding proteins: Affibody binding proteins developed from a small three-helix bundle scaffold. FEBS J 2008, 275:2668-2676.

Silverman et al.: Multivalent avimer proteins evolved by exon shuffling of a family of human receptor domains. Nat Biotechnol 2005, 23:1556-1561.

Skerra: Engineered protein scaffolds for molecular recognition. J Mol Recognit 2000, 13:167-187.

Skerra: Alternative non-antibody scaffolds for molecular recognition. Curr Opin Biotechnol 2007, 18:295-304.

Skerra: Alternative binding proteins: Anticalins—harnessing the structural plasticity of the lipocalin ligand pocket to engineer novel binding activities. FEBS J 2008, 275:2677-2683.

Stumpp et al.: DARPins: a new generation of protein therapeutics. Drug Discov Today 2008, 13:695-701.

The invention claimed is:

1. A method of treatment, comprising: identifying circulating non-hematopoietic cells that express CD321 in a subject, wherein the circulating non-hematopoietic cells are cancer cells; and
administering a cancer treatment to the subject, wherein the cancer treatment is a tumor vaccine, chemotherapy, radiotherapy, cell based immunotherapy, immune checkpoint inhibition or hormone therapy.

2. The method according to claim 1, wherein the circulating non-hematopoietic cells that express CD321 are identified in circulating cells from peripheral blood, urine, feces, lymph or another exudate or secretory fluid of the subject.

3. The method according to claim 1, wherein a circulating non-hematopoietic cell that expresses CD321 is identified as non-hematopoietic by the absence of expression of at least one pan-leukocyte marker and of at least one thrombocyte marker by said cell.

4. The method according to claim 1, wherein the circulating non-hematopoietic cells that express CD321 are identified by a method comprising:
a) obtaining a biological sample from the subject, said biological sample comprising circulating cells from the subject;
b) detecting in said biological sample non-hematopoietic cells negative for at least one pan-leukocyte marker and negative for at least one thrombocyte marker;
c) detecting the expression of CD321 by the cells as detected in b).

5. The method according to claim 3, wherein:
a) said pan-leukocyte marker is selected from the group consisting of CD45, LSP1, CD48, and combinations thereof;
b) said thrombocyte marker is selected from the group consisting of CD36, CD41, CD42a, CD42b, CD61, and combinations thereof;
c) said pan-leukocyte marker is selected from the group consisting of CD45, LSP1, CD48, and combinations thereof, and said thrombocyte marker is selected from the group consisting of CD36, CD41, CD42a, CD42b, CD61, and combinations thereof;
d) said pan-leukocyte marker is CD45;
e) said thrombocyte marker is CD42a; or
f) said pan-leukocyte marker is CD45 and said thrombocyte marker is CD42a.

6. The method according to claim 1, wherein the circulating non-hematopoietic cells that express CD321 are from solid tumor.

7. The method according to claim 1, wherein the circulating non-hematopoietic cells that express CD321 are of epithelial, mesenchymal or melanocyte origin.

8. The method according to claim 1, wherein the subject is human.

9. The method according to claim 1, wherein the circulating non-hematopoietic cells that express CD321 express CD321 protein or CD321 mRNA or both.

10. The method according to claim 1, wherein the circulating non-hematopoietic cells that express CD321 are detected, quantified or isolated using a technique which employs one or more agents capable of specifically binding to CD321.

11. The method according to claim 10, wherein the technique further employs one or more agents capable of specifically binding to the at least one pan-leukocyte marker and one or more agents capable of specifically binding to the at least one thrombocyte marker.

12. The method according to claim 10, wherein the one or more agents are, each independently, one or more antibodies or antibody antigen binding fragments.

13. The method according to claim 1, wherein the circulating non-hematopoietic cells that express CD321 are detected, quantified or isolated using a technique selected from the group consisting of flow cytometry, mass cytometry, fluorescence activated cell sorting, fluorescence microscopy, affinity separation, magnetic cell separation, microfluidic separation, and combinations thereof.

14. The method according to claim 1, further comprising subjecting the circulating non-hematopoietic cells that express CD321 to biochemical analysis, mutation analysis, transcriptomic analysis and/or proteomic analysis.

15. The method of claim 1, further comprising monitoring of a neoplastic disease in the subject after the cancer treatment, wherein the monitoring comprises detecting circulating non-hematopoietic cells that express CD321 in a sample from the subject after the cancer treatment.

16. The method of claim 4, wherein the biological sample is blood, urine, feces, lymph or another exudate or secretory fluid.

17. The method of claim 4, wherein the biological sample is peripheral blood.

\* \* \* \* \*

SEQUENCE LISTING

```
<160> NUMBER OF SEQ ID NOS: 3

<210> SEQ ID NO 1
<211> LENGTH: 900
<212> TYPE: DNA
<213> ORGANISM: Homo sapiens

<400> SEQUENCE: 1
atggggacaa aggcgcaagt cgagaggaaa ctgttgtgcc tcttcatatt ggcgatcctg      60
ttgtgctccc tggcattggg cagtgttaca gtgcactctt ctgaacctga agtcagaatt     120
cctgagaata atcctgtgaa gttgtcctgt gcctactcgg gcttttcttc tccccgtgtg     180
gagtggaagt tgaccaagg agacaccacc agactcgttt gctataataa caagatcaca     240
gcttcctatg aggaccgggt gaccttcttg ccaactggta tcaccttcaa gtccgtgaca     300
cgggaagaca ctgggacata cacttgtatg gtctctgagg aaggcggcaa cagctatggg     360
gaggtcaagg tcaagctcat cgtgcttgtg cctccatcca gcctacagt taacatcccc      420 tcctctgcca ccattgggaa ccgggcagtg ctgacatgct cagaacaaga tggttcccca     480
ccttctgaat acacctggtt caaagatggg atagtgatgc tacgaatcc caaaagcacc      540 cgtgccttca gcaactcttc ctatgtcctg aatcccacaa caggagagct ggtctttgat     600
cccctgtcag cctctgatac tggagaatac agctgtgagg cacggaatgg gtatgggaca     660
cccatgactt caaatgctgt gcgcatggaa gctgtggagc ggaatgtggg ggtcatcgtg     720
gcagccgtcc ttgtaaccct gattctcctg ggaatcttgg tttttggcat ctggtttgcc     780
tatagccgag gccactttga cagaacaaag aaagggactt cgagtaagaa ggtgatttac     840
agccagccta gtgcccgaag tgaaggagaa ttcaaacaga cctcgtcatt cctggtgtga     900

<210> SEQ ID NO 2
<211> LENGTH: 299
<212> TYPE: PRT
<213> ORGANISM: Homo sapiens

<400> SEQUENCE: 2

Met Gly Thr Lys Ala Gln Val Glu Arg Lys Leu Leu Cys Leu Phe Ile
1               5                   10                  15

Leu Ala Ile Leu Leu Cys Ser Leu Ala Leu Gly Ser Val Thr Val His
                20                  25                  30

Ser Ser Glu Pro Glu Val Arg Ile Pro Glu Asn Asn Pro Val Lys Leu
            35                  40                  45

Ser Cys Ala Tyr Ser Gly Phe Ser Ser Pro Arg Val Glu Trp Lys Phe
        50                  55                  60
```

```
Asp Gln Gly Asp Thr Thr Arg Leu Val Cys Tyr Asn Asn Lys Ile Thr
 65                  70                  75                  80

Ala Ser Tyr Glu Asp Arg Val Thr Phe Leu Pro Thr Gly Ile Thr Phe
                 85                  90                  95

Lys Ser Val Thr Arg Glu Asp Thr Gly Thr Tyr Thr Cys Met Val Ser
                100                 105                 110

Glu Glu Gly Gly Asn Ser Tyr Gly Glu Val Lys Val Lys Leu Ile Val
            115                 120                 125

Leu Val Pro Pro Ser Lys Pro Thr Val Asn Ile Pro Ser Ser Ala Thr
        130                 135                 140

Ile Gly Asn Arg Ala Val Leu Thr Cys Ser Glu Gln Asp Gly Ser Pro
145                 150                 155                 160

Pro Ser Glu Tyr Thr Trp Phe Lys Asp Gly Ile Val Met Pro Thr Asn
                165                 170                 175

Pro Lys Ser Thr Arg Ala Phe Ser Asn Ser Ser Tyr Val Leu Asn Pro
                180                 185                 190

Thr Thr Gly Glu Leu Val Phe Asp Pro Leu Ser Ala Ser Asp Thr Gly
            195                 200                 205

Glu Tyr Ser Cys Glu Ala Arg Asn Gly Tyr Gly Thr Pro Met Thr Ser
        210                 215                 220

Asn Ala Val Arg Met Glu Ala Val Glu Arg Asn Val Gly Val Ile Val
225                 230                 235                 240

Ala Ala Val Leu Val Thr Leu Ile Leu Leu Gly Ile Leu Val Phe Gly
                245                 250                 255

Ile Trp Phe Ala Tyr Ser Arg Gly His Phe Asp Arg Thr Lys Lys Gly
                260                 265                 270

Thr Ser Ser Lys Lys Val Ile Tyr Ser Gln Pro Ser Ala Arg Ser Glu
                275                 280                 285

Gly Glu Phe Lys Gln Thr Ser Ser Phe Leu Val
        290                 295

<210> SEQ ID NO 3
<211> LENGTH: 250
<212> TYPE: PRT
<213> ORGANISM: Homo sapiens

<400> SEQUENCE: 3

Met Gly Thr Lys Ala Gln Val Glu Arg Lys Leu Leu Cys Leu Phe Ile
 1               5                  10                  15

Leu Ala Ile Leu Leu Cys Ser Leu Ala Leu Gly Ser Val Thr Val His
                 20                  25                  30

Ser Ser Glu Pro Glu Val Arg Ile Pro Glu Asn Asn Pro Val Lys Leu
             35                  40                  45

Ser Cys Ala Tyr Ser Gly Phe Ser Ser Pro Arg Val Glu Trp Lys Phe
         50                  55                  60

Asp Gln Gly Asp Thr Thr Arg Leu Val Cys Tyr Asn Asn Lys Ile Thr
 65                  70                  75                  80

Val Pro Pro Ser Lys Pro Thr Val Asn Ile Pro Ser Ser Ala Thr Ile
                 85                  90                  95

Gly Asn Arg Ala Val Leu Thr Cys Ser Glu Gln Asp Gly Ser Pro Pro
                100                 105                 110

Ser Glu Tyr Thr Trp Phe Lys Asp Gly Ile Val Met Pro Thr Asn Pro
                115                 120                 125

Lys Ser Thr Arg Ala Phe Ser Asn Ser Ser Tyr Val Leu Asn Pro Thr
```

-continued

```
            130                 135                 140
Thr Gly Glu Leu Val Phe Asp Pro Leu Ser Ala Ser Asp Thr Gly Glu
145                 150                 155                 160

Tyr Ser Cys Glu Ala Arg Asn Gly Tyr Gly Thr Pro Met Thr Ser Asn
                165                 170                 175

Ala Val Arg Met Glu Ala Val Glu Arg Asn Val Gly Val Ile Val Ala
                180                 185                 190

Ala Val Leu Val Thr Leu Ile Leu Leu Gly Ile Leu Val Phe Gly Ile
            195                 200                 205

Trp Phe Ala Tyr Ser Arg Gly His Phe Asp Arg Thr Lys Lys Gly Thr
        210                 215                 220

Ser Ser Lys Lys Val Ile Tyr Ser Gln Pro Ser Ala Arg Ser Glu Gly
225                 230                 235                 240

Glu Phe Lys Gln Thr Ser Ser Phe Leu Val
                245                 250
```